(12) United States Patent
Jakobsen et al.

(10) Patent No.: US 8,519,100 B2
(45) Date of Patent: Aug. 27, 2013

(54) NON-NATURALLY OCCURRING T CELL RECEPTORS

(75) Inventors: Bent Karsten Jakobsen, Oxfordshire (GB); Naomi Harwood, Oxfordshire (GB); Nathanial Ross Liddy, Abingdon (GB)

(73) Assignee: Immunocore Ltd. (GB)

( * ) Notice: Subject to any disclaimer, the term of this patent is extended or adjusted under 35 U.S.C. 154(b) by 0 days.

(21) Appl. No.: 13/342,579

(22) Filed: Jan. 3, 2012

(65) Prior Publication Data

US 2012/0225481 A1 Sep. 6, 2012

Related U.S. Application Data

(63) Continuation-in-part of application No. PCT/GB2010/001277, filed on Jul. 1, 2010.

(30) Foreign Application Priority Data

Jul. 3, 2009 (GB) .................................... 0911566.8

(51) Int. Cl.
*C07K 1/00* (2006.01)
*C07K 14/00* (2006.01)
*C07K 17/00* (2006.01)

(52) U.S. Cl.
USPC ......................................................... 530/350

(58) Field of Classification Search
None
See application file for complete search history.

(56) References Cited

U.S. PATENT DOCUMENTS

2002/0058253 A1 5/2002 Kranz et al.

FOREIGN PATENT DOCUMENTS

| EP | 1 795 599 | 6/2007 |
|---|---|---|
| WO | WO 99/60120 | 11/1999 |
| WO | WO 03/020763 | 3/2003 |
| WO | WO 2004/048410 | 6/2004 |
| WO | WO 2005/114215 | 12/2005 |
| WO | WO 2006/054096 | 5/2006 |
| WO | WO 2006/129085 | 12/2006 |
| WO | WO 2007/131092 | 11/2007 |
| WO | WO 2008/089053 | 7/2008 |

OTHER PUBLICATIONS

Paul, WE., Fundamental Immunology, 3rd Edition, Raven Press, New York, Chapt. 8, pp. 292-295, 1993.*
Rudikoff S. et. al. Proc. Natl. Acad. Sci. USA, 79(6):1979-1983, Mar. 1982.*
MacCallum et. al. J. Mol. Biol., 262, 732-745, 1996.*
Casset et al (Biochemical and Biophysical Research Communications, 307:198-205, 2003.*
Lukasz K. Chlewicki, et al., High-Affinity, Peptide-Specific T Cell Receptors Can Be Generated by Mutations in CDRI, CDR2 or CDR3, J. Mol. Biol. (2005) vol. 346, p. 223-239.
Cristina Maccalli, et al., TCR β-Chain Variable Region-Driven Selection and Massive Expansion of HLA-Class 1-Restricted Antitumor CTL Lines From HLA-A 0201+Melanoma Patients[1], J. Of Immunology (1997) vol. 158. p. 5902-5913.
Richard A. Morgan, et al., High Efficiency TCR Gene Transfer Into Primary Human Lymphocytes Affords Avid Recognition of Melanoma Tumor Antigen Glycoprotein 100 and Does Not Alter the Recognition of Autologous Melanoma Antigens, J. of Immunology (2003) vol. 171, p. 3287-3295.
Niels Schaft, et al., Peptide Fine Specificity of Anti-Glycoprotein 100 CTL is Preserved Following Transfer of Engineered TCRαβ Genes Into Primary Human T Lymphocytes[1], Journal of Immunology (2003) vol. 170. p. 2186-2194.
Ching Y. Voss, et al., Increased Effector-Target Cell Conjugate Formation Due to HLA Restricted Specific Antigen Recognition, Immunol. Res (2009) vol. 45, p. 13-24.

* cited by examiner

*Primary Examiner* — Robert Landsman
(74) *Attorney, Agent, or Firm* — Vedder Price P.C.; Thomas J. Kowalski; Smitha B. Uthaman

(57) ABSTRACT

A T cell receptor (TCR) having the property of binding to the gp100 YLEPGPVTA peptide-HLA-A2 complex and comprising a TCR alpha variable domain and/or a TCR beta variable domain, characterized in that the domains are mutated relative to a TCR having the extracellular alpha and beta chain sequences SEQ ID NOs: 2 and that the TCR has a binding affinity for, and/or a binding half-life for, the YLEPG-PVTA-HLA-A2 complex at least double that of a reference TCR. Embodiments of the invention such as the use of such TCRs in adoptive therapy, and fusions of such TCRs with therapeutic agents are also described.

34 Claims, 20 Drawing Sheets

Figure 1A. Wild Type gp100-specific TCR TRAV17/TRAJ29/TRAC alpha chain amino acid sequence, but with K113 substituted for N113 (i.e. N4 of the TRAC constant region) (SEQ ID No: 2)

```
          10           20           30
          *            *            *
S Q Q G E E D P Q A L S I Q E G E N A T M N C S Y K T S I N N L Q W Y R Q N S
 40           50           60           70           80
 *            *            *            *            *
G R G L V H L I L I R S N E R E K H S G R L R V T L D T S K K S S S L L I T A S R
          90          100          110          120
          *            *            *            *
A A D T A S Y F C A T D G D T P L V F G K G T R L S V I A N I Q K P D P A V Y Q
         130          140          150          160
          *            *            *            *
L R D S K S S D K S V C L F T D F D S Q T N V S Q S K D S D V Y I T D K T V L D
         170          180          190          200
          *            *            *            *
M R S M D F K S N S A V A W S N K S D F A C A N A F N N S I I P E D T F F P S P

E S S
```

Figure 1B. Reference TCR alpha chain (see Figure 1C) DNA sequence (SEQ ID No: 4) (introduced cysteine is shaded):

```
cat atg agt caa caa gga gaa gaa gat cct cag gcc ttg agc
atc cag gag ggt gaa aat gcc acc atg aac tgc agt tac aaa
act agt ata aac aat tta cag tgg tat aga caa aat tca ggt
aga ggc ctt gtc cac cta att tta ata cgt tca aat gaa aga
gag aaa cac agt gga aga tta aga gtc acg ctt gac act tcc
aag aaa agc agt tcc ttg ttg atc acg gct tcc cgg gca gca
gac act gct tct tac ttc tgt gct acg gac gga gac aca cct
ctt gtc ttt gga aag ggc aca aga ctt tct gtg att gca aat
atc cag aag cct gac cct gcc gtg tac cag ctg aga gac tct
aag tcg agt gac aag tct gtc tgc cta ttc acc gat ttt gat
tct caa aca aat gtg tca caa agt aag gat tct gat gtg tat
atc aca gac aaa tgt gtg cta gac atg agg tct atg gac ttc
aag agc aac agt gct gtg gcc tgg agc aac aaa tct gac ttt
gca tgt gca aac gcc ttc aac aac agc att att cca gaa gac
acc ttc ttc ccc agc cca gaa agt tcc taa gct t
```

Figure 1C. Reference TCR alpha chain - Wild Type gp100-specific TCR
TRAV17/TRAJ29/TRAC alpha chain amino acid sequence, but with cysteine
(bold and underlined) substituted for T157 (i.e. T48 of the TRAC constant region)
(SEQ ID No: 45), and with K113 substituted for N113.

```
          10           20           30
           *            *            *
S Q Q G E E D P Q A L S I Q E G E N A T M N C S Y K T S I N N L Q W Y R Q N S
 40           50           60           70           80
  *            *            *            *            *
G R G L V H L I L I R S N E R E K H S G R L R V T L D T S K K S S S L L I T A S R
          90          100          110          120
           *            *            *            *
A A D T A S Y F C A T D G D T P L V F G K G T R L S V I A N I Q K P D P A V Y Q
         130          140          150          160
           *            *            *            *
L R D S K S S D K S V C L F T D F D S Q T N V S Q S K D S D V Y I T D K C V L D
         170          180          190          200
           *            *            *            *
M R S M D F K S N S A V A W S N K S D F A C A N A F N N S I I P E D T F F P S P

E S S
```

Figure 2A. Wild Type gp100-specific TCR TRBV19*01/TRBD1/TRBJ2-7*01/TRBC2 beta chain amino acid sequence, (SEQ ID No: 3)

```
            10          20          30
            *           *           *
D G G I T Q S P K Y L F R K E G Q N V T L S C E Q N L N H D A M Y W Y R Q D P
40          50          60          70
*           *           *           *
G Q G L R L I Y Y S Q I V N D F Q K G D I A E G Y S V S R E K K E S F P L T V T
80          90          100         110
*           *           *           *
S A Q K N P T A F Y L C A S S I G G P Y E Q Y F G P G T R L T V T E D L K N V F
120         130         140         150
*           *           *           *
P P E V A V F E P S E A E I S H T Q K A T L V C L A T G F Y P D H V E L S W W V
160         170         180         190
*           *           *           *
N G K E V H S G V S T D P Q P L K E Q P A L N D S R Y C L S S R L R V S A T F
 200         210         220         230
 *           *           *           *
W Q N P R N H F R C Q V Q F Y G L S E N D E W T Q D R A K P V T Q I V S A E A
   240
   *
W G R A D
```

Figure 2B. gp100-specific TCR beta chain wild type DNA sequence (SEQ ID No: 5) (introduced cysteine is shaded):

```
cat atg gat ggt gga att act caa tcc cca aag tac ctg ttc
aga aag gaa gga cag aat gtg acc ctg agt tgt gaa cag aat
ttg aac cac gat gcc atg tac tgg tac cgacag gac cca ggg
caa ggg ctg aga ttg atc tac tac tca cag ata gta aat gac
ttt cag aaa gga gat ata gct gaa ggg tac agc gtc tct cgg
gag aag aag gaa tcc ttt cct ctc act gtg aca tcg gcc caa
aag aac ccg aca gct ttc tat ctc tgt gcc agt agt ata ggg
ggc ccc tac gag cag tac ttc ggg ccg ggc acc agg ctc acg
gtc aca gag gac ctg aaa aac gtg ttc cca ccc gag gtc gct
gtg ttt gag cca tca gaa gca gag atc tcc cac acc caa aag
gcc aca ctg gtg tgc ctg gcc acc ggt ttc tac ccc gac cac
gtg gag ctg agc tgg tgg gtg aat ggg aag gag gtg cac agt
ggg gtc tgc aca gac ccg cag ccc ctc aag gag cag ccc gcc
ctc aat gac tcc aga tac gct ctg agc agc cgc ctg agg gtc
tcg gcc acc ttc tgg cag gac ccc cgc aac cac ttc cgc tgt
caa gtc cag ttc tac ggg ctc tcg gag aat gac gag tgg acc
cag gat agg gcc aaa ccc gtc acc cag atc gtc agc gcc gag
gcc tgg ggt aga gca gac taa gct t
```

**Figure 2C. Reference TCR beta chain - Wild Type gp100-specific TCR TRBV19*01/TRBD1/TRBJ2-7*01/TRBC2 beta chain amino acid sequence, but with cysteine (bold and underlined) substituted for S169 (i.e. S57 of the TRBC2 constant region) and with A187 substituted for C187 and D201 substituted for N201 (SEQ ID No: 46)**

```
                  10            20            30
                   *             *             *
D G G I T Q S P K Y L F R K E G Q N V T L S C E Q N L H D A M Y W Y R Q D P
         40            50            60            70
          *             *             *             *
G Q G L R L I Y Y S Q I V N D F Q K G D I A E G Y S V S R E K K E S F P L T V T
         80            90           100           110
          *             *             *             *
S A Q K N P T A F Y L C A S S I G G P Y E Q Y F G P G T R L T V T E D L K N V F
        120           130           140           150
          *             *             *             *
P P E V A V F E P S E A E I S H T Q K A T L V C L A T G F Y P D H V E L S W W V
        160           170           180           190
          *             *             *             *
N G K E V H S G V C T D P Q P L K E Q P A L N D S R Y A L S S R L R V S A T F
        200           210           220           230
          *             *             *             *
W Q D P R N H F R C Q V Q F Y G L S E N D E W T Q D R A K P V T Q I V S A E A
           240
            *
W G R A D
```

Figure 3A
High Affinity gp100-specific TCR alpha chain variable domain amino acid sequence (SEQ ID No: 7):
SQQGEEDPQALSIQEGENATMNCSYKTSINNLQWYRQNSGRGLVHLILIRSNEREKH
SGRLRVTLDTSKKSSSLLITASRAADTASYFCATDG<u>S</u>TPL<u>M</u>FGKGTRLSVIA

Figure 3B
High Affinity gp100-specific TCR alpha chain variable domain amino acid sequence (SEQ ID No: 8):
XQQGEEDPQALSIQEGENATMNCSYKTSINNLQWYRQNSGRGLVHLILIRSNEREKH
SGRLRVTLDTSKKSSSLLITASRAADTASYFCATDG<u>S</u>TP<u>MQ</u>FGKGTRLSVIA
(X = S or A or G)

Figure 3C
High Affinity gp100-specific TCR alpha chain variable domain amino acid sequence (SEQ ID No: 9):
SQQGEEDPQALSIQEGENATMNCSYKTSINNLQWYRQNSGRGLVHLILIRSNEREKH
SGRLRVTLDTSKKSSSLLITASRAADTASYFCATDG<u>TT</u>PL<u>G</u>FGK<u>D</u>TRLSVIA

Figure 4A
High Affinity gp100-specific TCR beta chain variable domain amino acid sequence (SEQ ID No: 10):
DGGITQSPKYLFRKEGQNVTLSCEQNLNHDAMYWYRQDPGQGLRLIYYS<u>WAQG</u>DF
QKGDIAEGYSVSREKKESFPLTVTSAQKNPTAFYLCASSIGGPYEQYFGPGTRLTVT

Figure 4B
High Affinity gp100-specific TCR beta chain variable domain amino acid sequence (SEQ ID No: 11):
DGGITQSPKYLFRKEGQNVTLSCEQNLNHDAMYWYRQDPGQGLRLIYYS<u>WAQG</u>DF
QKGDI<u>T</u>EGYSVSREKKESFPLTVTSAQKNPTAFYLCASSIGGPYEQYFGPGTRLTVT

Figure 4C

High Affinity gp100-specific TCR beta chain variable domain amino acid sequence (SEQ ID No: 12):

DGGITQSPKYLFRKEGQNVTLSCEQNLNHDAMYWYRQDPGQGLRLIYYS<u>WAQGNF</u>
QKGDIAEGYSVSREKKESFPLTVTSAQKNPTAFYLCASSIGGPYEQYFGPGTRLTVT

Figure 4D

High Affinity gp100-specific TCR beta chain variable domain amino acid sequence (SEQ ID No: 13):

DGGITQSPKYLFRKEGQNVTLSCEQNLNHDAMYWYRQDPGQGLRLIYYS<u>WGVGDF</u>
QKGDI<u>T</u>EGYSVSREKKESFPLTVTSAQKNPTAFYLCASSIGGPYEQYFGPGTRLTVT

Figure 4E

High Affinity gp100-specific TCR beta chain variable domain amino acid sequence (SEQ ID No: 14):

DGGITQSPKYLFRKEGQNVTLSCEQNLNHDAMYWYRQDPGQGLRLIYYS<u>WAQGHF</u>
QKGDIAEGYSVSREKKESFPLTVTSAQKNPTAFYLCASSIGGPYEQYFGPGTRLTVT

Figure 4F

High Affinity gp100-specific TCR beta chain variable domain amino acid sequence (SEQ ID No: 15):

DGGITQSPKYLFRKEGQNVTLSCEQNLNHDAMYWYRQDPGQGLRLIYYS<u>WAQGNF</u>
QKGDIAEGYSVSREKKESFPLTVTSAQKNPTAFYLCASSIGGPYEQYFGPGTRLTVT

Figure 4G

High Affinity gp100-specific TCR beta chain variable domain amino acid sequence (SEQ ID No: 16):

DGGITQSPKYLFRKEGQNVTLSCEQNLNHDAMYWYRQDPGQGLRLIYYS<u>WAYGHF</u>
QKGDIAEGYSVSREKKESFPLTVTSAQKNPTAFYLCASSIGGPYEQYFGPGTRLTVT

Figure 4H

High Affinity gp100-specific TCR beta chain variable domain amino acid sequence (SEQ ID No: 17):

DGGITQSPKYLFRKEGQNVTLSCEQNLNHDAMYWYRQDPGQGLRLIYYS<u>WAVGNF</u>QKGDIAEGYSVSREKKESFPLTVTSAQKNPTAFYLCASSIGGPYEQYFGPGTRLTVT

Figure 4I

High Affinity gp100-specific TCR beta chain variable domain amino acid sequence (SEQ ID No: 18):

DGGITQSPKYLFRKEGQNVTLSCEQNLNHDAMYWYRQDPGQGLRLIYYSQIVNDFQKGDIAEGYSVSREKKESFPLTVTSAQKNPTAFYLCAS<u>LYCEG</u>YEQYFGPGTRLTVT

Figure 4J

High Affinity gp100-specific TCR beta chain variable domain amino acid sequence (SEQ ID No: 19):

DGGITQSPKYLFRKEGQNVTLSCEQNLNHDAMYWYRQDPGQGLRLIYYS<u>WAQF</u>DFQKGDIAEGYSVSREKKESFPLTVTSAQKNPTAFYLCASSIGGPYEQYFGPGTRLTVT

Figure 4K

High Affinity gp100-specific TCR beta chain variable domain amino acid sequence (SEQ ID No: 20):

DGGITQSPKYLFRKEGQNVTLSCEQNLNHDAMYWYRQDPGQGLRLIYYS<u>WGTG</u>DFQKGDIAEGYSVSREKKESFPLTVTSAQKNPTAFYLCASSIGGPYEQYFGPGTRLTVT

Figure 4L

High Affinity gp100-specific TCR beta chain variable domain amino acid sequence (SEQ ID No: 21):

DGGITQSPKYLFRKEGQNVTLSCEQN<u>IFQKK</u>MYWYRQDPGQGLRLIYYSQIVNDFQKGDIAEGYSVSREKKESFPLTVTSAQKNPTAFYLCASSIGGPYEQYFGPGTRLTVT

Figure 4M

High Affinity gp100-specific TCR beta chain variable domain amino acid sequence (SEQ ID No: 22):

DGGITQSPKYLFRKEGQNVTLSCEQNLNHDAMYWYRQDPGQGLRLIYYS<u>WGTG</u>DF
QKGDIAEGYSVSREKKESFPLTVTSAQKNPTAFYLCASSIG<u>A</u>PY<u>P</u>QYFGPGTRLTVT

Figure 4N

High Affinity gp100-specific TCR beta chain variable domain amino acid sequence (SEQ ID No: 23):

DGGITQSPKYLFRKEGQNVTLSCEQNLNHDAMYWYRQDPGQGLRLIYYS<u>WGTG</u>DF
QKGDIAEGYSVSREKKESFPLTVTSAQKNPTAFYLCASS<u>H</u>G<u>A</u>PYEQYFGPGTRLTVT

Figure 4O

High Affinity gp100-specific TCR beta chain variable domain amino acid sequence (SEQ ID No: 24):

DGGITQSPKYLFRKEGQNVTLSCEQNLNHDAMYWYRQDPGQGLRLIYYS<u>WGTG</u>DF
QKGDIAEGYSVSREKKESFPLTVTSAQKNPTAFYLCASS<u>W</u>G<u>A</u>PYEQYFGPGTRLTVT

Figure 4P

High Affinity gp100-specific TCR beta chain variable domain amino acid sequence (SEQ ID No: 25):

DGGITQSPKYLFRKEGQNVTLSCEQNLNHDAMYWYRQDPGQGLRLIYYS<u>WAQG</u>DF
QKGDIAEGYSVSREKKESFPLTVTSAQKNPTAFYLCASSIG<u>A</u>PY<u>P</u>QYFGPGTRLTVT

Figure 4Q

High Affinity gp100-specific TCR beta chain variable domain amino acid sequence (SEQ ID No: 26):

DGGITQSPKYLFRKEGQNVTLSCEQNLNHDAMYWYRQDPGQGLRLIYYS<u>WAQG</u>DF
QKGDIAEGYSVSREKKESFPLTVTSAQKNPTAFYLCASS<u>H</u>G<u>A</u>PYEQYFGPGTRLTVT

Figure 4R

High Affinity gp100-specific TCR beta chain variable domain amino acid sequence (SEQ ID No: 27):

DGGITQSPKYLFRKEGQNVTLSCEQNLNHDAMYWYRQDPGQGLRLIYYS<u>WAQ</u>GDF
QKGDIAEGYSVSREKKESFPLTVTSAQKNPTAFYLCASS<u>W</u>G<u>A</u>PYEQYFGPGTRLTVT

Figure 4S

High Affinity gp100-specific TCR beta chain variable domain amino acid sequence (SEQ ID No: 28):

DGGITQSPKYLFRKEGQNVTLSCEQNLNHDAMYWYRQDPGQGLRLIYYSQIVNDFQ
KGDIAEGYSVSREKKESFPLTVTSAQKNPTAFYLCASS<u>W</u>G<u>A</u>PYEQYFGPGTRLTVT

Figure 4T

High Affinity gp100-specific TCR beta chain variable domain amino acid sequence (SEQ ID No: 29):

DGGITQSPKYLFRKEGQNVTLSCEQNLNHDAMYWYRQDPGQGLRLIYYSQIVNDFQ
KGDIAEGYSVSREKKESFPLTVTSAQKNPTAFYLCASS<u>Y</u>G<u>A</u>PYEQYFGPGTRLTVT

Figure 4U

High Affinity gp100-specific TCR beta chain variable domain amino acid sequence (SEQ ID No: 30):

DGGITQSPKYLFRKEGQNVTLSCEQNLNHDAMYWYRQDPGQGLRLIYYSQIVNDFQ
KGDIAEGYSVSREKKESFPLTVTSAQKNPTAFYLCASS<u>F</u>G<u>A</u>PYEQYFGPGTRLTVT

Figure 4V

High Affinity gp100-specific TCR beta chain variable domain amino acid sequence (SEQ ID No: 31):

DGGITQSPKYLFRKEGQNVTLSCEQNLNHDAMYWYRQDPGQGLRLIYYSQIVNDFQ
KGDIAEGYSVSREKKESFPLTVTSAQKNPTAFYLCASS<u>H</u>G<u>A</u>PYEQYFGPGTRLTVT

Figure 4W

High Affinity gp100-specific TCR beta chain variable domain amino acid sequence (SEQ ID No: 32):

DGGITQSPKYLFRKEGQNVTLSCEQNLNHDAMYWYRQDPGQGLRLIYYSQIVNDFQ
KGDIAEGYSVSREKKESFPLTVTSAQKNPTAFYLCASS<u>S</u>G<u>A</u>PYEQYFGPGTRLTVT

Figure 4X

High Affinity gp100-specific TCR beta chain variable domain amino acid sequence (SEQ ID No: 33):

DGGITQSPKYLFRKEGQNVTLSCEQNLNHDAMYWYRQDPGQGLRLIYYS<u>WIT</u>GDFQ
KGDIAEGYSVSREKKESFPLTVTSAQKNPTAFYLCASSIGGPYEQYFGPGTRLTVT

Figure 4Y

High Affinity gp100-specific TCR beta chain variable domain amino acid sequence (SEQ ID No: 34):

DGGITQSPKYLFRKEGQNVTLSCEQNLNHDAMYWYRQDPGQGLRLIYYS<u>WG</u>V<u>G</u>DF
QKGDIAEGYSVSREKKESFPLTVTSAQKNPTAFYLCASSIGGPYEQYFGPGTRLTVT

Figure 4Z

High Affinity gp100-specific TCR beta chain variable domain amino acid sequence (SEQ ID No: 35):

DGGITQSPKYLFRKEGQNVTLSCEQNLNHDAMYWYRQDPGQGLRLIYYS<u>WGT</u>NDF
QKGDIAEGYSVSREKKESFPLTVTSAQKNPTAFYLCASSIGGPYEQYFGPGTRLTVT

In-vitro cell staining using high affinity gp100 TCR evaluated by flow cytometry:

1) No TCR
2) $10^{-7}$ M variant gp100 peptide + Irrelevant TCR
3) $10^{-9}$ M variant gp100 peptide + gp100 high affinity TCR
4) $10^{-8}$ M variant gp100 peptide + gp100 high affinity TCR
5) $10^{-7}$ M variant gp100 peptide + gp100 high affinity TCR
6) $10^{-7}$ M irrelevant peptide + gp100 high affinity TCR In-vitro cell staining using high affinity gp100 TCR evaluated by microscopy:

Figure 6

SEQ ID No 36: - Amino acid sequence of an anti-CD3 scFv antibody fragment (bold type) fused via a linker namely GGGGS (underlined) at the N-terminus of a gp100 TCR β chain. The gp100 TCR β chain contains the variable region SEQ ID No: 27:

XXQMTQSPSSLSASVGDRVTITCRASQDIRNYLNWYQQKPGKAPKLLIYYTSRLES
GVPSRFSGSGSGTDYTLTISSLQPEDFATYYCQQGNTLPWTFGQGTKVEIKGGGGS
GGGGSGGGGSGGGGSGGGGSEVQLVESGGGLVQPGGSLRLSCAASGYSFTGYTM
NWVRQAPGKGLEWVALINPYKGVSTYNQKFKDRFTISVDKSKNTAYLQMNSLRAE
DTAVYYCARSGYYGDSDWYFDVWGQGTLVTVSS<u>GGGGS</u>DGGITQSPKYLFRKEG
QNVTLSCEQNLNHDAMYWYRQDPGQGLRLIYYSWAQGDFQKGDIAEGYSVSREKK
ESFPLTVTSAQKNPTAFYLCASSWGAPYEQYFGPGTRLTVTEDLKNVFPPEVAVFEP
SEAEISHTQKATLVCLATGFYPDHVELSWWVNGKEVHSGVCTDPQPLKEQPALNDS
RYALSSRLRVSATFWQDPRNHFRCQVQFYGLSENDEWTQDRAKPVTQIVSAEAWG
RAD

X at position 1 = D or A
X at position 2 = I or Q

Figure 7

Redirection of T cells (within the PBMC population) by the test anti-CD3 scFv-gp100 high affinity TCR to kill the melanoma cell line Mel526 (non-radioactive cytotoxicity assay)

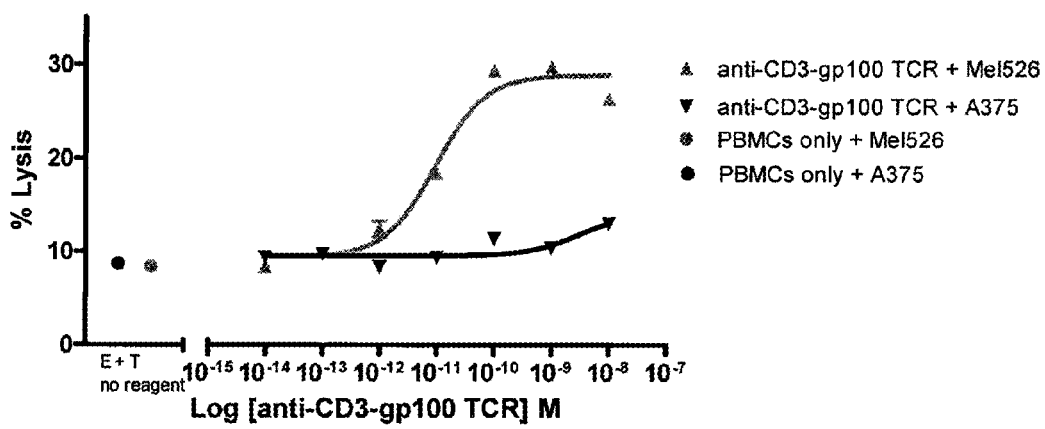

Figure 8A

DNA sequence for the Wild Type gp100-specific TCR WT alpha chain-2A-WT beta chain with Porcine teschovirus-1 2A sequence (bold and underlined) (SEQ ID No: 37):

<u>gctagc</u>cgccaccatggaaaccctgctgggcgtgagcctggtcatcctgtggctgcagctggccagagtgaattccca gcagggcgaagaggaccccaggccctcagcatccaggaaggcgagaacgccaccatgaactgcagctacaag accagcatcaacaacctgcagtggtacagacagaacagcggcagaggcctggtgcacctgatcctgatcagaagca acgagcgggagaagcacagcggcaggctgagagtgaccctggacaccagcaagaagtccagcagcctgctgatc accgccagcagagccgccgacaccgccagctactttgcgccaccgacggcgacacccccctggtgttcggcaagg gcaccagactgagcgtgatcgccaatattcagaagcccgaccccgccgtctaccagctgcgggacagcaagagcag cgacaagagcgtgtgcctgttcaccgacttcgacagccagaccaacgtgtcccagagcaaggacagcgacgtgtac atcaccgacaagaccgtgctggacatgcggagcatggacttcaagagcaacagcgccgtggcctggtccaacaaga gcgacttcgcctgcgccaacgccttcaacaacagcatcatccccgaggacaccttttcccagccccgagagcagct gcgacgtcaaactggtggagaagtccttcgagacagacaccaacctgaacttccagaacctctccgtgatcggcttca gaatcctgctgctgaaggtggccggcttcaacctgctgatgaccctgcggctgtggagcagcggcagccgggccaag agaagcggatccggc<u>gccaccaacttctccctgctgaagcaggccggcgacgtggaggaaaaccctggccc</u> taggatgagcaaccaggtgctctgctgcgtggtgctgtgtttcctggggggccaacaccgtggacggcggcatcacccag agccccaagtacctgttccggaaagagggccagaacgtcaccctgagctgcgagcagaacctcaaccacgacgcc atgtactggtacaggcaggacccaggacaaggcctccggctgatctactacagccagatcgtgaacgacttccagaa gggcgatattgccgagggctacagcgtgtcccgggagaagaaagagagcttcccccctgaccgtcaccagcgcccag aagaacccccaccgccttctacctgtgcgccagcagcatcggcggaccctacgagcagtacttcggccctggcacccg gctgacagtgactgaggacctgaagaacgtgttccccccgaggtggccgtgttcgagcccagcgaggccgagatca gccacacccagaaagccaccctggtctgcctggccaccggcttttaccccgaccacgtggagctgtcttggtgggtgaa cggcaaagaggtgcacagcggcgtcagcaccgaccccagcctctcaaagagcagcccgccctgaacgacagcc ggtactgcctcagctctcggctgcgggtgtccgccaccttctggcagaaccccggaaccacttccggtgccaggtgca gttctacggcctgagcgagaacgacgagtggactcaggatagagccaagcccgtgacccagatcgtgtccgccgag gcctgggggcgcgccgattgcggcttcaccagcgagagctatcagcagggcgtgctgtctgccaccatcctgtacgag atcctgctgggcaaggccaccctgtacgccgtgctcgtgtctgccctggtgctgatggctatggtcaagcggaaggaca gccggggctaa<u>gtcgac</u>

Figure 8B

Wild Type gp100 -specific TCR WT alpha chain-2A-WT beta chain amino acid sequence with Porcine teschovirus-1 2A sequence (bold and underlined) (SEQ ID No: 38)

```
                 10          20          30          40
                  *           *           *           *
METLLGVSLVILWLQLARVNSQQGEEDPQALSIQEGENAT
                 50          60          70          80
                  *           *           *           *
MNCSYKTSINNLQWYRQNSGRGLVHLILIRSNEREKHSGR
                 90         100         110         120
                  *           *           *           *
LRVTLDTSKKSSSLLITASRAADTASYFCATDGDTPLVFGK
               130         140         150         160
                  *           *           *           *
GTRLSVIANIQKPDPAVYQLRDSKSSDKSVCLFTDFDSQT
                170         180         190         200
                  *           *           *           *
NVSQSKDSDVYITDKTVLDMRSMDFKSNSAVAWSNKSDF
                 210         220         230         240
                  *           *           *           *
ACANAFNNSIIPEDTFFPSPESSCDVKLVEKSFETDTNLNF
               250         260         270         280
                  *           *           *           *
QNLSVIGFRILLLKVAGFNLLMTLRLWSSGSRAKRSGSGA
               290         300         310         320
                  *           *           *           *
TNFSLLKQAGDVEENPGPRMSNQVLCCVVLCFLGANTVD
                330         340         350
                  *           *           *
GGITQSPKYLFRKEGQNVTLSCEQNLNHDAMYWYRQDPG
```

Increased activation of gp100 improved-affinity TCR-transduced T cells compared to wild type-affinity TCR-transduced T cells in response to tumour cell lines.

CD8+ T cell activation by gp100 TCR-anti-CD3 scFv fusions having different TCR-pMHC affinities T-cell redirection assay testing the potency of high affinity gp100 TCR-anti-CD3 fusions

US 8,519,100 B2

NON-NATURALLY OCCURRING T CELL RECEPTORS

INCORPORATION BY REFERENCE

This application is a continuation-in-part application of international patent application Serial No. PCT/GB2010/001277 filed Jul. 1, 2010, which published as PCT Publication No. WO2011/001152 on Jan. 6, 2011, which claims benefit of UK patent application Serial No. 0911566.8 filed Jul. 3, 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to T cell receptors (TCRs) which bind the YLEPGPVTA (SEQ ID NO: 1) peptide (derived from the gp100 protein) presented as a peptide-HLA-A2 complex, the TCRs being mutated relative to the native gp100 TCR alpha and/or beta variable domains and having binding affinities for, and/or binding half-lives for, the complex at least double that of a reference gp 100 TCR.

BACKGROUND TO THE INVENTION

With respect to TCRs, mention is made of international patent application Serial No. PCT/GB2005/001924 filed on May 18, 2005 which published as WO/2005/113595 on Dec. 1, 2005 and U.S. Application U.S. Ser. No. 11/596,458 filed on Nov. 13, 2006, both incorporated herein by reference.

The YLEPGPVTA (SEQ ID NO: 1) peptide corresponds to amino acid residue numbers 280-288 of human glycoprotein 100 (gp100) protein. Gp100 is widely, and significantly overexpressed on melanoma cancer cells. For example, one study (Trefzer et al., (2006) *Melanoma Res.* 16(2): 137-45) found that 82% of 192 melanoma metastases from 28 melanoma patients expressed gp100. Several studies reported higher expression levels of gp100 in melanoma tissues (Hofbauer et al., (2004) *J Immunother.* 27(1): 73-8, Barrow et al., (2006) *Clin Cancer Res.* 12:764-71). The YLEPGPVTA (SEQ ID NO: 1) peptide is presented by Class I HLA molecules on gp100+/HLA-A2 cancer cells. (Salgaller et al., (1996) *Cancer Res* 56: 4749-4757)

Therefore, the YLEPGPVTA (SEQ ID NO: 1) HLA-A2 complex provides a cancer marker that the TCRs of the invention can target. For example, TCRs of the invention may be used for the purpose of delivering cytotoxic agents to the cancer cells, or may be transformed into T-cells, rendering them capable of destroying tumour cells presenting that HLA complex, for administration to a patient in the treatment process known as adoptive therapy. However, for the former purpose it would be desirable if the TCRs had a considerably higher affinity and/or considerably slower off-rate, so that the TCRs reside on the targeted tumour cells for an extended period of time. For the latter purpose, it would be desirable if the TCRs had somewhat a higher affinity and/or a slower off-rate for the peptide-HLA complex than native TCRs specific for that complex, but not as high affinity as for the former purpose. Dramatic increases in affinity have been associated with a loss of antigen specificity in TCR gene-modified CDS T cells, which could result in the nonspecific activation of these TCR-transfected CDS T cells, so intermediate affinity TCRs would be preferred for adoptive therapy (see Zhao et al., (2007) *J Immunol.* 179: 5S45-54; Robbins et al., (2005) *J Immunol.* 180: 6116-31; and see also published WO 200S/03S002). The present invention provides such TCRs.

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV17" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV19" defines a TCR Vβ region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The α and β chains of αβ TCR's are generally regarded as each having two "domains", namely variable and constant domains. The variable domain consists of a concatenation of variable region, and joining region. In the present specification and claims, the term "TCR alpha variable domain" therefore refers to the concatenation of TRAV, and TRAJ regions, and the term TCR alpha constant domain refers to the extracellular TRAC region, or to a C-terminal truncated TRAC sequence. Likewise the term "TCR beta variable domain" refers to the concatenation of TRBV and TRBD/TRBJ regions, and the term TCR beta constant domain refers to the extracellular TRBC region, or to a C-terminal truncated TRBC sequence.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

Citation or identification of any document in this application is not an admission that such document is available as prior art to the present invention.

SUMMARY OF THE INVENTION

It was confirmed that a native gp100 TCR clone has the following alpha chain and beta chain V, J and C gene usage:

Alpha chain—TRAV17/TRAJ29/TRAC (the extracellular sequence of the native gp100 TCR alpha chain is given in SEQ ID NO: 2.

Beta chain:—TRBV19*01/TRBD1/TRBJ2-7*01/TRBC2 (the extracellular sequence of the native gp100 TCR beta chain is given in SEQ ID No: 3. (Note that the TRBV19 sequence has three allelic variants, designated in IMGT nomenclature as TRBV19*01, *02 and *03 respectively, and the native gp100 TCR clone referred to above has the *01 variation. In the same way, the TRBJ2-7 sequence has two known variations and it is the *01 sequence which is present in the TCR clone referred to above. Note also that the absence of a "*" qualifier means that only one allele is known for the relevant sequence.)

The terms "wild type TCR", "native TCR", "wild type gp100 TCR" and "native gp100 TCR" are used synonymously herein to refer to this naturally occurring TCR having the extracellular alpha and beta chain SEQ ID NOs: 2 and 3. All embodiments of the invention relate to isolated or non-naturally occurring or engineered TCRs.

An embodiment of the invention relates to a T cell receptor (TCR) having the property of binding to YLEPGPVTA (SEQ ID NO: 1) HLA-A2 complex and comprising a TCR alpha variable domain and/or a TCR beta variable domain, characterized in that or wherein the TCR is mutated, relative to a TCR having the extracellular alpha and beta chain sequences SEQ ID NOs: 2 and 3, in its alpha chain variable domain which comprises amino acids 1 to 109 of SEQ ID NO: 2 and/or its beta chain variable domain which comprises amino acids 1 to 112 of SEQ ID NO: 3. Further, the alpha variable domain has at least 90% sequence identity to the amino acid sequence 1 to 109 of SEQ ID NO: 2, and/or said beta variable domain has at least 90% sequence identity to the amino acid sequence 1 to 112 of SEQ ID NO: 3. Furthermore, the TCR has a binding affinity for, and/or a binding half-life for, the YLEPGPVTA (SEQ ID NO: 1)-HLA-A2 complex at least double that of a reference TCR having the extracellular alpha chain sequence SEQ ID NO: 45 and the extracellular beta chain sequence SEQ ID NO: 46.

Another embodiment of the invention relates to a TCR having the property of binding to YLEPGPVTA (SEQ ID NO: 1) HLA-A2 complex and having the alpha chain variable domain sequence of amino acids 1 to 109 of SEQ ID NO: 2, except that amino acid residues at one or more of positions 94D, 97L, 98V or 102G are mutated, and/or having the beta chain variable sequence of amino acids 1 to 112 of SEQ ID NO: 3 except that amino acid residues at one or more of positions 27L, 28N, 29H, 30D, 31A, 50Q, 51I, 52V, 53N, 54D, 61A, 94S, 95 I, 96G, 97G, 98P or 100E are mutated.

Another embodiment of the invention relates to a TCR wherein the alpha chain variable domain comprises one or more amino acid substitutions selected from the group consisting of: 94S, 94T, 94R, 97M, 98M, 98Q, 98G, 98S, 98A and 102D, with reference to the position numbering of SEQ ID NO: 2.

Another embodiment of the invention relates to a TCR wherein the beta chain variable domain comprises one or more amino acid substitutions selected from the group consisting of: 27I, 28F, 29Q, 30K, 31K, 50W, 51A, 51G, 52Q, 52Y, 52T, 53G, 53F, 54N, 54H, 61T, 94L, 95Y, 95H, 95W, 95F, 95S, 95V, 96C, 97E, 97A, 98G, 100Q and 100P, with reference to the position numbering of SEQ ID NO: 3.

Another embodiment of the invention relates to a TCR wherein the TCR is associated with a detectable label, a therapeutic agent, a PK modifying moiety or any combination thereof.

Yet another embodiment of the invention relates to a multivalent TCR complex comprising at least two or more mutated TCRs.

Another embodiment of the invention relates to DNA or RNA encoding the mutated TCRs.

Another embodiment of the invention relates to isolated cells presenting the mutated TCRs.

A still further embodiment of the invention is a TCR comprising: a TCR alpha chain variable domain comprising an amino acid sequence selected from the group consisting of:
(i) the TCR alpha chain sequence SEQ ID NO: 45, wherein amino acids 1 to 109 are replaced by the sequence SEQ ID NO: 8, wherein amino acid at position 1 is S;
(ii) the TCR alpha chain sequence SEQ ID NO: 45, wherein amino acids 1 to 109 are replaced by the sequence SEQ ID NO: 8, wherein amino acid at position 1 is A;
(iii) the TCR alpha chain sequence SEQ ID NO: 45, wherein amino acids 1 to 109 are replaced by the sequence SEQ ID NO: 8, wherein amino acid at position 1 is G;
(iv) the TCR alpha chain sequence SEQ ID NO: 45, wherein amino acids 1 to 109 are replaced by the sequence SEQ ID NO: 8, wherein amino acid at position 1 is S, and the C-terminus of the alpha chain is truncated by 8 amino acids from F196 to S203 inclusive, based on the numbering of SEQ ID NO: 45;
(v) the TCR alpha chain sequence SEQ ID NO: 45, wherein amino acids 1 to 109 are replaced by the sequence SEQ ID NO: 8, wherein amino acid at position 1 is A, and the C-terminus of the alpha chain is truncated by 8 amino acids from F196 to S203 inclusive, based on the numbering of SEQ ID NO: 45; and
(vi) the TCR alpha chain sequence SEQ ID NO: 45, wherein amino acids 1 to 109 are replaced by the sequence SEQ ID NO: 8, wherein amino acid at position 1 is G, and the C-terminus of the alpha chain is truncated by 8 amino acids from F196 to S203 inclusive, based on the numbering of SEQ ID NO: 45;

and a TCR beta chain variable domain comprising a TCR beta chain-anti-CD3 amino acid sequence selected from the group consisting of:
(vii) the TCR beta chain-anti-CD3 sequence SEQ ID NO: 36, wherein amino acids at positions 1 and 2 are D and I respectively;
(viii) the TCR beta chain-anti-CD3 sequence SEQ ID NO: 36, wherein amino acids at positions 1 and 2 are A and I respectively;
(ix) the TCR beta chain-anti-CD3 sequence SEQ ID NO: 36, wherein amino acids at positions 1 and 2 are A and Q respectively;
(x) the TCR beta chain-anti-CD3 sequence SEQ ID NO: 36, wherein amino acids at positions 1 and 2 are D and I respectively amino acids at positions 108-131 are replaced by SEQ ID NO: 44, and amino acids at positions 254-258 are replaced by SEQ ID NO: 47;
(xi) the TCR beta chain-anti-CD3 sequence SEQ ID NO: 36, wherein amino acids at positions 1 and 2 are D and I respectively and amino acid at position 257 is a S and amino acid at position 258 is a G;
(xii) the TCR beta chain-anti-CD3 sequence SEQ ID NO: 36, wherein amino acids at positions 1 and 2 are D and I respectively and amino acid at position 256 is a S and amino acid at position 258 is a G;
(xiii) the TCR beta chain-anti-CD3 sequence SEQ ID NO: 36, wherein amino acids at positions 1 and 2 are D and I respectively and amino acid at position 255 is a S and amino acid at position 258 is a G;

(xiv) a TCR beta chain-anti-CD3 having the sequence SEQ ID NO: 36, wherein amino acids at positions 1 and 2 are A and Q, and wherein amino acid at position 257 is a S and amino acid at position 258 is a G.

(xv) a TCR beta chain-anti-CD3 having the sequence SEQ ID NO: 36, wherein amino acids at positions 1 and 2 are A and Q, and wherein amino acid at position 256 is a S and amino acid at position 258 is a G;

(xvi) a TCR beta chain-anti-CD3 having the sequence SEQ ID NO: 36, wherein amino acids at positions 1 and 2 are A and Q, and wherein amino acid at position 255 is a S and amino acid at position 258 is a G;

(xvii) and a TCR beta chain-anti-CD3 having the sequence SEQ ID NO: 36, wherein amino acid at positions 1 and 2 are A and I respectively, and wherein amino acid at position 257 is a S and amino acid at position 258 is a G;

(xviii) a TCR beta chain-anti-CD3 having the sequence SEQ ID NO: 36, wherein amino acid at positions 1 and 2 are A and I respectively, and wherein amino acid at position 256 is a S and amino acid at position 258 is a G; and (xix) a TCR beta chain-anti-CD3 having the sequence SEQ ID NO: 36, wherein amino acids at positions 1 and 2 are A and I respectively, and wherein amino acid at position 255 is a S and amino acid at position 258 is a G.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The examples and the following detailed description, given by way of example, but not intended to limit the invention solely to the specific embodiments described, may best be understood in conjunction with the accompanying drawings, in which:

FIGS. 1A and 2A respectively show the extracellular amino acid sequences of the native gp100 TCR alpha chain having the TRAV17/TRAJ29/TRAC gene usage, except that K113 has been substituted for N113 (i.e. N4 of TRAC), and of the native gp100 TCR beta chain having the TRBV19*01/TRBD1/TRBJ2-7*01/TRBC2 gene usage (SEQ ID NOs: 2 and 3 respectively).

FIGS. 1B and 2B respectively show DNA sequences encoding soluble wild-type gp100 TCR alpha and beta chains also referred to as the reference gp100 TCR alpha and beta chains. These sequences include additional cysteine residues to form a non-native disulphide bond. The mutated codons encoding the additional cysteine residues are indicated by shading. The NdeI and HindIII restriction enzyme recognition sequences are underlined.

FIGS. 1C and 2C respectively show the soluble wild-type gp100 TCR, or reference gp100 TCR, alpha and beta chain extracellular amino acid sequences (SEQ ID NOs: 45 and 46 respectively) produced from the DNA sequences of FIGS. 1B and 2B respectively, but without the introduced leading methionine inserted for efficient expression in bacteria. The introduced cysteines are bold and underlined.

FIGS. 3A-C show the alpha chain variable domain amino acid sequences of the high affinity gp100 TCR variants. The mutated residues are bold and underlined.

FIGS. 4A-Z show the beta chain variable domain amino acid sequences of the high affinity gp100 TCR variants. The mutated residues are bold and underlined.

FIG. 6 shows the amino acid sequence of an anti-CD3 scFv antibody fragment (bold type) fused via a linker namely GGGGS SEQ ID NO: 48 (underlined) at the N-terminus of a gp100 TCR beta chain. The gp100 TCR beta chain contains the variable region SEQ ID NO: 27.

FIG. 7 is a response curve showing the redirection of T cells by an anti-CD3 scFv-gp100 high affinity TCR to kill the melanoma cell line Mel526 in a non-radioactive cytotoxicity assay.

FIG. 8A shows the DNA sequence for the wild type gp100-specific TCR gene (WT alpha chain-2A-WT beta chain construct with the Porcine teschovirus-1 2A sequence bold and underlined) for transduction of T-cells.

FIGS. 8B and 8C shows the amino acid sequence (SEQ ID NO: 38) of the wild type gp 100-specific TCR for T-cell transduction produced from the DNA sequence of FIG. 8A. The Porcine teschovirus-1 2A sequence is bold and underlined.

DETAILED DESCRIPTION

Figure 5A:
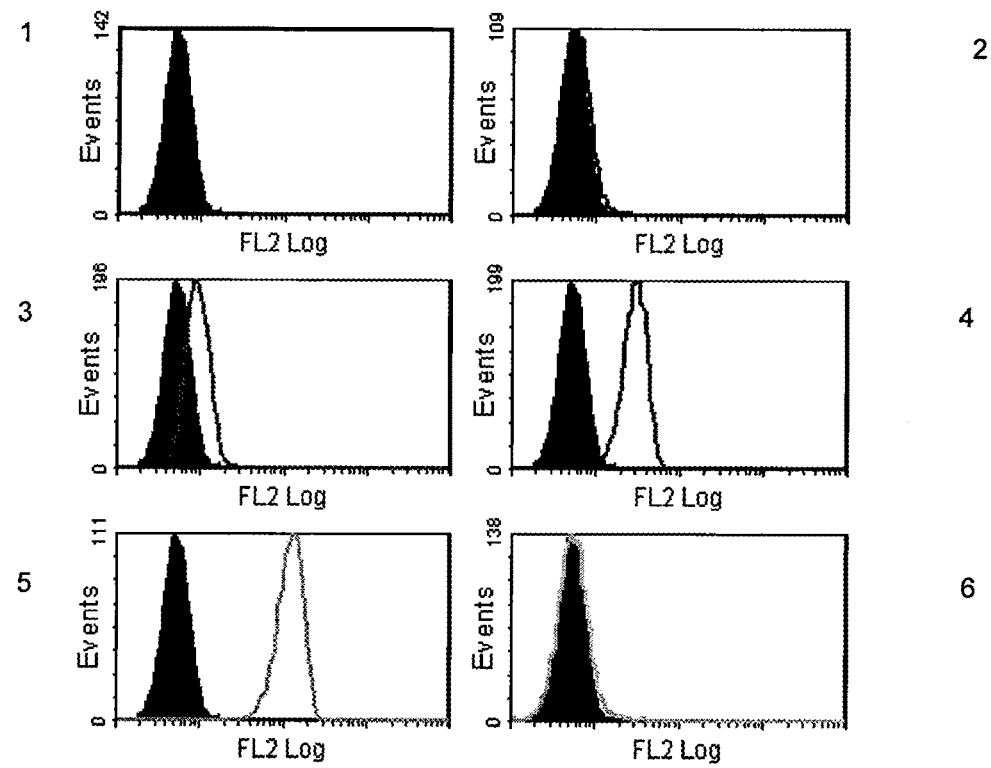
FIG. 5A shows flow cytometry data for the in vitro staining of T2 cells pulsed with the YLEPGPVTV (SEQ ID NO: 6) variant gp100 peptide by a high affinity gp100 TCR.

According to the invention, there is provided an isolated or non-naturally occurring or engineered T cell receptor (TCR)

having the property of binding to YLEPGPVTA (SEQ ID NO: 1) HLA-A2 complex and comprising a TCR alpha variable domain and/or a TCR beta variable domain, characterized in that or wherein said TCR (i) is mutated relative to a native gp100 TCR having the extracellular alpha and beta chain sequences SEQ ID NOs: 2 and 3 in its alpha chain variable domain (amino acids 1 to 109 of SEQ ID NO: 2) and/or its beta chain variable domain (amino acids 1 to 112 of SEQ ID NO: 3); and (ii) has a binding affinity for, and/or a binding half-life for, the YLEPGPVTA (SEQ ID NO: 1)-HLA-A2 complex at least double that of a reference gp100 TCR, the said reference gp100 TCR having the extracellular alpha chain sequence SEQ ID NO: 45 and the extracellular beta chain sequence SEQ ID NO: 46.

"Isolated" or "Non-naturally occurring" or "Engineered" TCRs refers to TCRs encoded by a sequence that is at least substantially free from at least one other component that the sequence is naturally associated and found in nature. Isolated or non-naturally occurring or engineered means that the sequence is at least substantially free from at least one other component that the sequence is naturally associated and found in nature, e.g., genomic sequences or has been modified in any manner from its natural state. e.g., genomic sequences have been modified in any manner from its natural state, including by isolation. Non-naturally occurring has the menaing ascribed to it in Diamond v. Chakrabarty, 447 U.S. 303, 206 U.S.P.Q. (BNA) 193 (1980) and MPEP 2105, i.e. a product of human ingenuity.

Note that SEQ ID NO: 45 is the native alpha chain extracellular sequence ID NO: 2 except that C157 has been substituted for T157 (i.e. T48 of TRAC), and K113 has been substituted for N113. Likewise SEQ ID NO: 46 is the native beta chain extracellular sequence ID NO: 3 except that C169 has been substituted for S169 (i.e. S57 of TRBC2), A187 has been substituted for C187 and D201 has been substituted for N201. These cysteine substitutions relative to the native alpha and beta chain extracellular sequences enable the formation of an interchain disulfide bond which stabilises the refolded soluble TCR, ie the TCR formed by refolding extracellular alpha and beta chains. Use of the stable disulfide linked soluble TCR as the reference TCR enables more convenient assessment of binding affinity and binding half life. The other mutations in the alpha chain SEQ ID NO: 45 and the beta chain SEQ ID NO: 46 relative to the native alpha and beta chains SEQ ID NOs: 2 and 3 are "silent" in the sense that they do not affect the binding affinity or binding half life relative the native sequence. Hence, if a TCR of the invention has a binding affinity for, and/or a binding half-life for, the YLEPG-PVTA-(SEQ ID NO: 1) HLA-A2 complex at least double that of the reference gp100 TCR, it impliedly also meets those criteria with respect to the native gp100 TCR clone referred to above.

The "reference gp100 TCR having the extracellular alpha chain sequence SEQ ID NO: 45 and the extracellular beta chain sequence SEQ ID NO: 46" are referred to synonymously hereafter either as "the reference TCR" or "the reference gp100 TCR".

Binding affinity (inversely proportional to the equilibrium constant $K_D$) and binding half-life (expressed as $T_{1/2}$) can be determined by any appropriate method. It will be appreciated that doubling the affinity of a TCR results in halving the $K_D$. $T_{1/2}$ is calculated as ln 2 divided by the off-rate ($k_{off}$). So doubling of $T_{1/2}$ results in a halving in $k_{off}$. $K_D$ and $k_{off}$ values for TCRs are usually measured for soluble forms of the TCR, i.e. those forms which are truncated to remove hydrophobic transmembrane domain residues. Therefore it is to be understood that a given TCR meets the requirement that it has a binding affinity for, and/or a binding half-life for, the YLEPG-PVTA (SEQ ID NO: 1)-HLA-A2 complex if a soluble form of that TCR meets that requirement. Preferably the binding affinity or binding half-life of a given TCR is measured several times, for example 3 or more times, using the same assay protocol, and an average of the results is taken. In a preferred embodiment these measurements are made using the Surface Plasmon Resonance (BIAcore) method of Example 3 herein. The reference gp100 TCR has Kn of approximately 19 μM as measured by that method, and the $k_{off}$ was approximately 1 s$^{-1}$ (i.e $T_{1/2}$ was approximately 0.7s).

As mentioned, YLEPGPVTA (SEQ ID NO: 1) is the native gp100$_{280-288}$ peptide presented in the HLA A2 complex. However, it is well known that a slightly modified version of that peptide (YLEPGPVTV (SEQ ID NO: 6)) shows enhanced binding to HLA-A2, increasing the stability of the peptide-HLA complex (Salgaller et al. (1996) *Cancer Res* 56: 4749-57). Thus the variant YLEPGPVTV (SEQ ID NO: 6) peptide-HLA-A2 complex is more suitable for assay work in assessment of potential TCRs capable of binding the YLEPG-PVTA (SEQ ID NO: 1)-HLA-A2 complex. Such TCRs bind both peptide HLA complexes with substantially similar $K_D$ and $T_{1/2}$.

The TCRs of the invention have an affinity and/or a binding half-life for the YLEPGPVTA (SEQ ID NO: 1)-HLA-A2 complex at least twice that of the reference gp100 TCR, while retaining acceptable YLEPGPVTA (SEQ ID NO: 1)-HLA-A2 complex specificity, for example similar to the reference gp100 TCR. In general, TCRs required as targeting agents for delivering therapeutic agents, such as cytotoxic or immune effector agents, to cells presenting the HLA complex should have considerably higher affinities and/or longer binding half-lives for the said YLEPGPVTA (SEQ ID NO: 1)-HLAA2 complex than the reference gp 100 TCR. Where the TCR is required for transfection of T-cells for adoptive therapy, lower affinities, for example and/or shorter binding half-lives (though still respectively at least twice those of the reference TCR) are generally required.

For example, TCRs of the invention may have a $K_D$ for the complex of ≦8 μM, ≦5 μM, ≦1 μM, ≦0.1 μM, ≦0.01 μM, ≦0.001 μM, or ≦0.0001 μM and/or have a binding half-life (T½) for the complex of ≧1.5 s, ≧3 s, ≧10 s, ≧20 s, ≧40 s, ≧60 s, ≧600 s, or ≧6000 s.

For the purposes of the present invention, a TCR is a moiety having at least one TCR alpha and/or TCR beta variable domain. Generally they comprise both a TCR alpha variable domain and a TCR beta variable domain. They may be αβ heterodimers or may be single chain format. For use as a targeting agent for delivering therapeutic agents to the antigen presenting cell an αβ heterodimeric TCR may be in soluble form (i.e. having no transmembrane of cytoplasmic domains). For stability, such soluble TCRs preferably have an introduced disulfide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full length chains having both cytoplasmic and transmembrane domains. If desired, an introduced disulfide bond between residues of the respective constant domains may be present (see for example WO 2006/000830). For use as a targeting agent for delivering therapeutic agents to the antigen presenting cell a soluble TCR may be in single chain format. These may include αβ TCR polypeptides of the Vα-L-Vβ, Vβ-L-Vα, Vα-Cα-L-Vα or Vα-L-Vβ-Cβ types, wherein Vα and Vβ are TCR α and β variable regions respectively, Cα and Cβ are TCR α and β constant regions respectively, and L is a linker sequence. Adoptive therapy can employ full-length TCR sequences incorporating the transmembrane domains as both native disulfide and introduced disulfide bond formats, or as a single chain TCR construct; or/and variations around this theme.

Whatever the format, the TCRs of the invention are mutated relative to the native gp100 TCR having the extracellular alpha and beta chain sequences SEQ ID NOs: 2 and 3 in their alpha variable domain (extending from S1 to A109 of SEQ ID NO: 2) and/or beta variable domain (extending from D1 to T112 of SEQ ID NO: 3). The native gp100 TCR or the reference gp 100 TCR can be used as a template into which the various mutations that cause high affinity and/or a slow off-rate for the interaction between TCRs of the invention and the YLEPGPVTA (SEQ ID NO: 1)-HLA-A2 complex can be introduced. Embodiments of the inventions include TCRs which are mutated relative to the a chain variable domain extending from S1 to A109 of SEQ ID NO: 2 and/or β chain variable domain extending from D1 to T112 of SEQ ID NO: 3 in at least one complementarity determining region (CDR) and/or variable domain framework region thereof.

Mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see Sambrook & Russell, (2001) Molecular Cloning—A Laboratory Manual (3$^{rd}$ Ed.) CSHL Press. Further information on LIC procedures can be found in (Rashtchian, (1995) *Curr Opin Biotechnol* 6 (1): 30-6).

One method for generating high affinity gp100 TCRs of the invention is selection from a diverse library of phage particles displaying such TCRs as disclosed in WO 2004/044004.

It should be noted that any αβ TCR that comprises similar Vα and Vβ gene usage and therefore variable domain amino acid sequences to that of the reference gp100 TCR could make a convenient template TCR. It would then be possible to introduce into the DNA encoding one or both of the variable domains of the template αβ TCR the changes required to produce the mutated high affinity TCRs of the invention. As will be obvious to those skilled in the art, the necessary mutations could be introduced by a number of methods, for example site-directed mutagenesis.

Preferred TCRs of the invention include those whose alpha variable domain has at least 90% (for example at least 93%, and preferably at least 94%) sequence identity to the amino acid sequence 1 to 109 of SEQ ID NO: 2 (i.e. less than 10% (or less than 7% or preferably less than 6%) of the residues of the native Vα domain are changed), and/or whose beta variable domain has at least 90% (for example at least 93%, and preferably at least 94%) sequence identity to the amino acid sequence 1 to 112 of SEQ ID NO: 3 (i.e. less than 10% (or less than 7% or preferably less than 6%) of the residues of the native Vα domain are changed). A single change includes a single insertion, deletion or mutation. Sequence identity may be determined, for example, by sequence alignment, either manually or by use of computer programs.

In some embodiments, the TCRs of the invention have the alpha chain variable domain extending from S1 to A109 of SEQ ID NO: 2, except that amino acid residues at one or more of positions 94D, 97L, 98V or 102G are mutated, and/or having the beta chain variable domain extending from D1 to T112 of SEQ ID NO: 3, except that amino acid residues at one or more of positions 27L, 28N, 29H, 30D, 31A, 50Q, 51I, 52V, 53N, 54D, 61A, 94S, 95 I, 96G, 97G, 98P or 100E are mutated. For example, TCRs of the invention may have one or more of alpha chain variable domain amino acid residues 94S, 94T, 94R, 97M, 98M, 98Q, 98G, 98S, 98A or 102D using the numbering shown in SEQ ID NO: 2, and/or one or more of beta chain variable domain amino acid residues 27I, 28F, 29Q, 30K, 31K, 50W, 51A, 51G, 52Q, 52Y, 52T, 53G, 53F, 54N, 54H, 61T, 94L, 95Y, 95H, 95W, 95F, 95S, 95V, 96C, 97E, 97A, 98G, 100Q or 100P using the numbering shown in SEQ ID NO: 3.

Specific TCRs of the invention include those comprising one of the alpha chain variable domain amino acid sequences SEQ ID NOs: 7, 8 and 9 and/or one of the beta chain variable domain amino acid sequences SEQ ID NOs: 10, 11, 12, 13, 14, 15, 16, 17, 18, 19, 20, 21, 22, 23, 24, 25, 26, 27, 28, 29, 30, 31, 32, 33, 34 and 35. Thus TCRs with the variable domain sequence of the wild type alpha chain (S1 to A109 of SEQ ID No 2) may be associated with a beta chain having one of SEQ ID NOs: 10-35. Alternatively, an alpha chain having one of SEQ ID NOs: 7-9 may be associated with the variable domain sequence of the wild type beta chain (D1 to T112) of SEQ ID No 3. Alternatively an alpha chain having one of SEQ ID NOs: 7-9 may be associated with a beta chain having one of SEQ ID NOs: 10-35. Currently preferred as soluble TCRs for targeting uses, principally for their high affinity and slow off-rate (i.e. long half-life), are those comprising the alpha chain variable domain amino acid sequence SEQ ID NO: 8 (X=S or A or G) and the beta chain variable domain amino acid sequence SEQ ID NO: 27. Such preferred TCRs are preferably in αβ heterodimeric format, ie including TRAC and TRBC domains. As mentioned, such TRAC and TRBC domains may be truncated at one C-terminus or both C termini. For example, the C-terminus of the constant domain of the reference TCR alpha chain may be truncated by deletion of up to 15, or up to 10 or up to 8 fewer amino acids.

Phenotypically silent variants of the TCRs discussed above also form part of this invention. The term "phenotypically silent variants" refers to TCRs which are identical in sequence to a TCR of the invention except that they incorporate changes in the constant and/or variable domains which do not alter the affinity and/or off-rate for the interaction with the peptide-HLA complex. One example of such a variant is provided by TCRs of the invention in which the TCR alpha constant domain contains a Phenylalanine (F) amino acid residue substituted for the 130 Serine (S) amino acid residue using the numbering of SEQ ID NO: 2.

As mentioned above, αβ heterodimeric TCRs of the invention may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned in the preceding paragraph, αβ heterodimeric TCRs of the invention may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

As mentioned, soluble TCRs of the invention may be associated (covalently or otherwise) with a detectable label (for diagnostic purposes wherein the TCR is used to detect the presence of cells presenting the YLEPGPVTA (SEQ ID NO: 1) HLA-A2 complex); a therapeutic agent; a PK modifying moiety (for example by PEGylation); or a combination of the above.

Detectable labels for diagnostic purposes include, but are not limited to, fluorescent or luminescent labels, radiolabels, MRI or CT contrast reagents, or enzymes that produce a detectable product.

Therapeutic agents which may be associated with the TCRs of the invention include, but are not limited to, radioactive compounds, prodrug activating enzymes (DT-diaphorase (DTD) or Biphenyl hydrolase-like protein (BPHL) for example), chemotherapeutic agents (cis-platin for example), toxins (*Pseudomonas* exotoxin such as PE38, calcimycin or diphtheria toxin for example), immune-modulating antibody fragments such as anti-CD3 or anti-CD16 for example, or immune-modulating cytokines (IL-2 for example). To ensure that toxic effects are exercised in the desired location the toxin could be inside a liposome linked to TCR so that the compound is released slowly or through coupling the toxin to the TCR via a labile linker. This will prevent damaging effects during the transport in the body and ensure that the toxin has maximum effect after binding of the TCR to the relevant antigen presenting cells.

Other suitable therapeutic agents include but are not limited to:
   small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;
   peptide cytotoxins, i.e. proteins or fragments thereof with the ability to kill mammalian cells. For example, ricin, diphtheria toxin, pseudomonas bacterial exotoxin A, DNase and RNase;
   radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;
   immuno-stimulants, i.e. immune effector molecules which stimulate immune response. For example, cytokines such as IL-2 and IFN-γ,
   Superantigens and mutants thereof;
   TCR-HLA fusions, wherein the HLA defines an immunogenic antigen;
   chemokines such as IL-8, platelet factor 4, melanoma growth stimulatory protein, etc;
   antibodies or fragments thereof, including anti-T cell or NK-cell determinant antibodies (e.g. anti-CD3 or anti-CD28 or anti-CD16);
   complement activators;
   xenogeneic protein domains, allogeneic protein domains, viral/bacterial protein domains, viral/bacterial peptides.

One preferred embodiment is provided by a TCR of the invention associated with an anti-CD3 antibody, or a functional fragment or variant of said anti-CD3 antibody. Antibody fragments and variants/analogues which are suitable for use in the compositions and methods described herein include but are not limited to minibodies, Fab fragments, F(ab')$_2$ fragments, dsFv and scFv fragments, or other antibody scaffold proteins such as Nanobodies™ (these constructs, marketed by Ablynx (Belgium), comprise synthetic single immunoglobulin variable heavy domain derived from a camelid (e.g. camel or llama) antibody), Domain Antibodies (marketed by Domantis (Belgium), comprising an affinity matured single immunoglobulin variable heavy domain or immunoglobulin variable light domain), UniBodies (marketed by Genmab, UniBodies are modified fully human IgG4 antibodies where the hinge region of the antibody has been eliminated), Trifunctional Antibodies (monoclonal antibodies with binding sites for two different antigens), Affibodies (marketed by Affibody, Affibodies are based on a 58-amino acid residue protein domain, a three helix bundle domain, derived from one of the IgG-binding domains of staphylococcal protein A), Anticalins (antibody mimetics synthesised from human lipocalins, which can also be formatted as dual targeting proteins, so-called Duocalins) or DARPins (Designed Ankyrin Repeat Proteins) (which are another example of antibody mimetic based on repeat proteins, such as ankyrin or leucine-rich repeat proteins, which are ubiquitous binding molecules).

More particular TCR-anti CD3 fusions of the invention include a TCR alpha chain amino acid sequence selected from the group consisting of:
   (i) the TCR alpha chain sequence SEQ ID NO: 45, wherein amino acids 1 to 109 are replaced by the sequence SEQ ID NO: 8, wherein amino acid at position 1 is S;
   (ii) the TCR alpha chain sequence SEQ ID NO: 45, wherein amino acids 1 to 109 are replaced by the sequence SEQ ID NO: 8, wherein amino acid at position 1 is A;
   (iii) the TCR alpha chain sequence SEQ ID NO: 45, wherein amino acids 1 to 109 are replaced by the sequence SEQ ID NO: 8, wherein amino acid at position 1 is G;
   (iv) the TCR alpha chain sequence SEQ ID NO: 45, wherein amino acids 1 to 109 are replaced by the sequence SEQ ID NO: 8, wherein amino acid at position 1 is S, and the C-terminus of the alpha chain is truncated by 8 amino acids from F196 to S203 inclusive, based on the numbering of SEQ ID NO: 45;
   (v) the TCR alpha chain sequence SEQ ID NO: 45, wherein amino acids 1 to 109 are replaced by the sequence SEQ ID NO: 8, wherein amino acid at position 1 is A, and the C-terminus of the alpha chain is truncated by 8 amino acids from F196 to S203 inclusive, based on the numbering of SEQ ID NO: 45;
   (vi) the TCR alpha chain sequence SEQ ID NO: 45, wherein amino acids 1 to 109 are replaced by the sequence SEQ ID NO: 8, wherein amino acid at position 1 is G, and the C-terminus of the alpha chain is truncated by 8 amino acids from F196 to S203 inclusive, based on the numbering of SEQ ID NO: 45; and a TCR beta chain-anti-CD3 amino acid sequence selected from the group consisting of:
   (vii) the TCR beta chain-anti-CD3 sequence SEQ ID NO: 36, wherein amino acids at positions 1 and 2 are D and I respectively;
   (viii) the TCR beta chain-anti-CD3 sequence SEQ ID NO: 36, wherein amino acids at positions 1 and 2 are A and I respectively;

(ix) the TCR beta chain-anti-CD3 sequence SEQ ID NO: 36, wherein amino acids at positions 1 and 2 are A and Q respectively;
(x) the TCR beta chain-anti-CD3 sequence SEQ ID NO: 36, wherein amino acids at positions 1 and 2 are D and I respectively amino acids at positions 108-131 are replaced by RTSGPGDGGKGGPGKGPGGEGTKGT-GPGG (SEQ ID NO: 44), and amino acids at positions 254-258 are replaced by GGEGGGSEGGGS (SEQ ID NO: 47);
(xi) the TCR beta chain-anti-CD3 sequence SEQ ID NO: 36, wherein amino acids at positions 1 and 2 are D and I respectively and amino acid at position 257 is a S and amino acid at position 258 is a G;
(xii) the TCR beta chain-anti-CD3 sequence SEQ ID NO: 36, wherein amino acids at positions 1 and 2 are D and I respectively and amino acid at position 256 is a S and amino acid at position 258 is a G;
(xiii) the TCR beta chain-anti-CD3 sequence SEQ ID NO: 36, wherein amino acids at positions 1 and 2 are D and I respectively and amino acid at position 255 is a S and amino acid at position 258 is a G;
(xiv) a TCR beta chain-anti-CD3 having the sequence SEQ ID NO: 36, wherein amino acids at positions 1 and 2 are A and Q, and wherein amino acid at position 257 is a S and amino acid at position 258 is a G.
(xv) a TCR beta chain-anti-CD3 having the sequence SEQ ID NO: 36, wherein amino acids at positions 1 and 2 are A and Q, and wherein amino acid at position 256 is a S and amino acid at position 258 is a G;
(xvi) a TCR beta chain-anti-CD3 having the sequence SEQ ID NO: 36, wherein amino acids at positions 1 and 2 are A and Q, and wherein amino acid at position 255 is a S and amino acid at position 258 is a G;
(xvii) and a TCR beta chain-anti-CD3 having the sequence SEQ ID NO: 36, wherein amino acid at positions 1 and 2 are A and I respectively, and wherein amino acid at position 257 is a S and amino acid at position 258 is a G;
(xviii) a TCR beta chain-anti-CD3 having the sequence SEQ ID NO: 36, wherein amino acids at positions 1 and 2 are A and I respectively, and wherein amino acid at position 256 is a S and amino acid at position 258 is a G;
(xix) a TCR beta chain-anti-CD3 having the sequence SEQ ID NO: 36, wherein amino acid at positions 1 and 2 are A and I respectively, and wherein amino acid at position 255 is a S and amino acid at position 258 is a G;

Examples of such TCR-anti CD3 fusions, based on the above description, are:

a TCR in which the alpha chain amino acid sequence is (i) and the beta chain-anti-CD3 amino acid sequence is (vii);
a TCR in which the alpha chain amino acid sequence is (i) and the beta chain-anti-CD3 amino acid sequence is (x);
a TCR in which the alpha chain amino acid sequence is (vi) and the beta chain-anti-CD3 amino acid sequence is (ix);
a TCR in which the alpha chain amino acid sequence is (v) and the beta chain-anti-CD3 amino acid sequence is (viii);
a TCR in which the alpha chain amino acid sequence is (vi) and the beta chain-anti-CD3 amino acid sequence is (vii);
a TCR in which the alpha chain amino acid sequence is (i) and the beta chain-anti-CD3 amino acid sequence is (xi);
a TCR in which the alpha chain amino acid sequence is (i) and the beta chain-anti-CD3 amino acid sequence is (xii);
a TCR in which the alpha chain amino acid sequence is (i) and the beta chain-anti-CD3 amino acid sequence is (xiii);
a TCR in which the alpha chain amino acid sequence is (vi) and the beta chain-anti-CD3 amino acid sequence is (xiv);
a TCR in which the alpha chain amino acid sequence is (vi) and the beta chain-anti-CD3 amino acid sequence is (xv);
a TCR in which the alpha chain amino acid sequence is (vi) and the beta chain-anti-CD3 amino acid sequence is (xvi);
a TCR in which the alpha chain amino acid sequence is (v) and the beta chain-anti-CD3 amino acid sequence is (xvii);
a TCR in which the alpha chain amino acid sequence is (v) and the beta chain-anti-CD3 amino acid sequence is (xviii);
a TCR in which the alpha chain amino acid sequence is (v) and the beta chain-anti-CD3 amino acid sequence is (xix);
a TCR in which the alpha chain amino acid sequence is (vi) and the beta chain-anti-CD3 amino acid sequence is (xi);
a TCR in which the alpha chain amino acid sequence is (vi) and the beta chain-anti-CD3 amino acid sequence is (xii); and
a TCR in which the alpha chain amino acid sequence is (vi) and the beta chain-anti-CD3 amino acid sequence is (xiii).

Since the αβ heterodimeric TCRs of the invention have utility in adoptive therapy, the invention also includes an isolated cell, especially a T-cell, presenting a TCR of the invention. There are a number of methods suitable for the transfection of T cells with DNA or RNA encoding the high affinity TCRs of the invention. (See for example Robbins et al., (2008) *J. Immunol.* 180: 6116-6131)). T cells expressing the high affinity TCRs of the invention will be suitable for use in adoptive therapy-based treatment of gp100$^+$ HLA-A2$^+$ cancers. As will be known to those skilled in the art there are a number of suitable methods by which adoptive therapy can be carried out. (See for example Rosenberg et al., (2008) *Nat Rev Cancer* 8 (4): 299-308).

For some purposes, the TCRs of the invention may be multimerised into a complex comprising several TCRs to form a multivalent TCR complex. There are a number of human proteins that contain a multimerisation domain that could be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment. (Willuda et al. (2001) J. Biol. Chem. 276 (17) 14385-14392). Haemoglobin also has a tetramerisation domain that could potentially be used for this kind of application. A multivalent TCR complex of the invention may have enhanced binding capability for the YLEPGPVTA (SEQ ID NO: 1)-HLA-A2 complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

The TCRs of the invention intended for use in adoptive therapy are glycosylated when expressed by the transfected T cells. As is well known, the glycosylation pattern of transfected TCRs may be modified by mutations of the transfected gene.

For administration to patients, the TCRs of the invention, and T cells transfected with TCRs of the invention, may be provided in pharmaceutical composition together with a pharmaceutically acceptable carrier. Therapeutic or imaging TCRs, multivalent TCR complexes and cells in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, preferably a parenteral (including subcutaneous, intramuscular, or preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

The invention will now be further described by way of the following non-limiting examples.

EXAMPLES

Example 1

Cloning of the Reference gp100 TCR Alpha and Beta Chain Variable Region Sequences into pGMT7-Based Expression Plasmids The reference gp100 TCR variable alpha and TCR variable beta domains were PCR amplified from total cDNA isolated from a gp100 T cell clone. In the case of the alpha chain, an alpha chain variable region sequence specific oligonucleotide A1 (ggaattccatatgagtcaacaaggagaagaagatcc SEQ ID NO: 39) which encodes the restriction site NdeI, an introduced methionine for efficient initiation of expression in bacteria, and an alpha chain constant region sequence specific oligonucleotide A2 (ttgtcagtcgacttagagtctctcagctggtacacg SEQ ID NO: 40) which encodes the restriction site SalI are used to amplify the alpha chain variable region. In the case of the beta chain, a beta chain variable region sequence specific oligonucleotide B1 (tctctcatatggatggtggaattactcaatccccaa SEQ ID NO: 41) which encodes the restriction site NdeI, an introduced methionine for efficient initiation of expression in bacteria, and a beta chain constant region sequence specific oligonucleotide B2 (tagaaaccggtggccaggcacaccagtgtggc SEQ ID NO: 42) which encodes the restriction site AgeI are used to amplify the beta chain variable region.

The alpha and beta variable regions were cloned into pGMT7-based expression plasmids containing either Cα or Cβ by standard methods described in (Molecular Cloning a Laboratory Manual Third edition by Sambrook and Russell). Plasmids were sequenced using an Applied Biosystems 3730×1 DNA Analyzer.

The DNA sequences encoding the TCR alpha chain cut with NdeI and SalI were ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI.

Ligation

Ligated plasmids are transformed into competent *Escherichia coli* strain XL1-blue cells and plated out on LB/agar plates containing 100 µg/ml ampicillin. Following incubation overnight at 37° C., single colonies are picked and grown in 10 ml LB containing 100 µg/ml ampicillin overnight at 37° C. with shaking. Cloned plasmids are purified using a Miniprep kit (Qiagen) and the insert is sequenced using an automated DNA sequencer (Lark Technologies).

FIGS. 1C and 2C show respectively the soluble disulfide-linked reference gp100 TCR α and β chain extracellular amino acid sequences, but without the introduced leading methionine inserted for efficient expression in bacteria (SEQ ID NOs: 45 and 46 respectively) produced from the DNA sequences of FIGS. 1B and 2B respectively. Note that cysteines were substituted in the constant regions of the alpha and beta chains to provide an artificial inter-chain disulphide bond on refolding to form the heterodimeric TCR. The introduced cysteines are shown shaded. The restriction enzyme recognition sequences in the DNA sequences of FIGS. 1B and 2B are underlined.

Example 2

Expression, Refolding and Purification of Soluble Reference gp100 TCR

The expression plasmids containing the TCR α-chain and β-chain respectively as prepared in Example 1 were transformed separately into *E. coli* strain Rosetta (DE3)pLysS, and single ampicillin-resistant colonies were grown at 37° C. in TYP (ampicillin 100 µg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH8.0, 0.5% Triton-X100, 200 mM NaCl, 10 mM NaEDTA) before being pelleted by centrifugation for 15 minutes at 4,000 rpm. Detergent and salt were then removed by a similar wash in the following buffer: 50 mM Tris-HCl, 1 mM NaEDTA, pH 8.0. Finally, the inclusion bodies were divided into 30 mg aliquots and frozen at −70° C. Inclusion body protein yield was quantitated by solubilising with 6 M Guanidine-HCl and an OD measurement was taken on a Hitachi U-2001 Spectrophotometer. The protein concentration was then calculated using the extinction coefficient.

Approximately 30 mg of TCR β chain and 60 mg of TCR α chain solubilised inclusion bodies were thawed from frozen stocks and diluted into 15 ml of a guanidine solution (6 M Guanidine-hydrochloride, 50 mM Tris HCl pH8.1, 100 mM NaCl, 10 mM EDTA, 10 mM DTT), to ensure complete chain denaturation. The guanidine solution containing fully reduced and denatured TCR chains were then injected into 1 liter of the following refolding buffer: 100 mM Tris pH 8.1, 400 mM L-Arginine, 2 mM EDTA, 5 M Urea. The redox couple (cysteamine hydrochloride and cystamine dihydrochloride (to final concentrations of 6.6 mM and 3.7 mM, respectively) were added approximately 5 minutes before addition of the denatured TCR chains. The solution was left for ~1 hr. The refolded TCR was dialysed in dialysis tubing cellulose membrane (Sigma-Aldrich; Product No. D9402) against 10 L H$_2$O at 5° C.±3° C. for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from misfolded, degradation products and impurities by loading the dialysed refold onto a POROS 50HQ anion exchange column and eluting bound protein with a gradient of 0-500 mM NaCl in 10 mM Tris pH 8.1 over 6 column volumes using an Akta purifier (GE Healthcare). A cocktail of protease inhibitors (Calbiochem) were added to the peak fractions. The fractions were then stored at 4° C. and analysed by Coomassie-stained SDS-PAGE before being pooled and concentrated. Finally, the soluble TCR was purified and characterised using a GE Healthcare Superdex 75HR gel filtration column pre-equilibrated in PBS buffer (Sigma). The peak eluting at a relative molecular weight of approximately 50 kDa was pooled and concentrated prior to characterisation by BIAcore surface plasmon resonance analysis.

Example 3

Binding Characterisation

BIAcore Analysis

A surface plasmon resonance biosensor (BIAcore 3000™) can be used to analyse the binding of a soluble TCR to its peptide-MHC ligand. This is facilitated by producing soluble biotinylated peptide-HLA ("pHLA") complexes which can be immobilised to a streptavidin-coated binding surface (sensor chip). The sensor chips comprise four individual flow cells which enable simultaneous measurement of T-cell receptor binding to four different pHLA complexes. Manual injection of pHLA complex allows the precise level of immobilised class I molecules to be manipulated easily.

Biotinylated class I HLA-A*02 molecules were refolded in vitro from bacterially-expressed inclusion bodies containing the constituent subunit proteins and synthetic peptide, followed by purification and in vitro enzymatic biotinylation (O'Callaghan et al. (1999) Anal. Biochem. 266: 9-15). HLA-A*02-heavy chain was expressed with a C-terminal biotinylation tag which replaces the transmembrane and cytoplasmic domains of the protein in an appropriate construct. Inclusion body expression levels of ~75 mg/liter bacterial culture were obtained. The HLA light-chain or β2-microglobulin (β2m) was also expressed as inclusion bodies in E. coli from an appropriate construct, at a level of ~500 mg/liter bacterial culture.

E. coli cells were lysed and inclusion bodies processed to approximately 80% purity. Synthetic peptide (gp100 YLEPGPVTA (SEQ ID NO: 1)) is dissolved in DMSO to a final concentration of 4 mg/ml. Inclusion bodies of b2m and heavy chain were denatured separately in 6 M guanidineHCl, 50 mM Tris pH 8.1, 100 mM NaCl, 10 mM DTT, 10 mM EDTA. Refolding buffer was prepared containing 0.4 M L-Arginine, 100 mM Tris pH 8.1, 3.7 mM cystamine dihydrochloride, 6.6 mM cysteamine hydrochloride and chilled to <5° C. Preferably the peptide is added first to the refold buffer, followed by addition of denatured b2m then addition of denatured heavy chain. The gp100 YLEPGPVTA (SEQ ID NO: 1) peptide is added to the refold buffer at 4 mg/liter (final concentration). Then 30 mg/liter b2m followed by 30 mg/liter heavy chain (final concentrations) are added. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 µm cellulose acetate filter and loaded onto a POROS 50HQ anion exchange column (8 ml bed volume). Protein was eluted with a linear 0-500 mM NaCl gradient in 10 mM Tris pH 8.1 using an Akta purifier (GE Healthcare). HLA-A*02-peptide complex eluted at approximately 250 mM NaCl, and peak fractions were collected, a cocktail of protease inhibitors (Calbiochem) was added and the fractions were chilled on ice.

Biotinylation tagged pHLA molecules were buffer exchanged into 10 mM Tris pH 8.1, 5 mM NaCl using a GE Healthcare fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl$_2$, and 5 µg/ml BirA enzyme (purified according to O'Callaghan et al. (1999) Anal. Biochem. 266: 9-15). The mixture was then allowed to incubate at room temperature overnight.

The biotinylated pHLA-A*02 molecules were purified using gel filtration chromatography. A GE Healthcare Superdex 75 HR 10/30 column was pre-equilibrated with filtered PBS and 1 ml of the biotinylation reaction mixture was loaded and the column was developed with PBS at 0.5 ml/min using an Akta purifier (GE Healthcare). Biotinylated pHLA-A*02 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*02 molecules were stored frozen at −20° C.

Such immobilised complexes are capable of binding both T-cell receptors and the coreceptor CD8αα, both of which may be injected in the soluble phase. The pHLA binding properties of soluble TCRs are observed to be qualitatively and quantitatively similar if the TCR is used either in the soluble or immobilised phase. This is an important control for partial activity of soluble species and also suggests that biotinylated pHLA complexes are biologically as active as non-biotinylated complexes.

The BIAcore 3000™ surface plasmon resonance (SPR) biosensor measures changes in refractive index expressed in response units (RU) near a sensor surface within a small flow cell, a principle that can be used to detect receptor ligand interactions and to analyse their affinity and kinetic parameters. The BIAcore experiments were performed at a temperature of 25° C., using PBS buffer (Sigma, pH 7.1-7.5) as the running buffer and in preparing dilutions of protein samples. Streptavidin was immobilised to the flow cells by standard amine coupling methods. The pHLA complexes were immobilised via the biotin tag. The assay was then performed by passing soluble TCR over the surfaces of the different flow cells at a constant flow rate, measuring the SPR response in doing so.

Equilibrium Binding Constant

The above BIAcore analysis methods were used to determine equilibrium binding constants. Serial dilutions of the disulfide linked soluble heterodimeric form of the reference gp100 TCR were prepared and injected at constant flow rate of 5 fll min-1 over two different flow cells; one coated with ~300 RU of specific YLEPGPVTA (SEQ ID NO: 1) HLA-A2 complex (or the variant peptide YLEPGPVTV (SEQ ID NO:

6) HLA-A2 complex), the second coated with ~300 RU of non-specific HLA-A2-WT1 wt peptide (RMFPNAPYL) complex. Response was normalised for each concentration using the measurement from the control cell. Normalised data response was plotted versus concentration of TCR sample and fitted to a non-linear curve fitting model in order to calculate the equilibrium binding constant, $K_D$. (Price & Dwek, Principles and Problems in Physical Chemistry for Biochemists ($2^{nd}$ Edition) 1979, Clarendon Press, Oxford). The disulfide linked soluble form of the reference gp100 TCR (Example 2) demonstrated a $K_D$ of approximately 19 μM. From the same BIAcore data the T½ was approximately 0.8 s.

This affinity determination was also repeated using a variant peptide (YLEPGPVTV—SEQ ID NO: 6) of the gp100 YLEPGPVTA (SEQ ID NO: 1) peptide loaded by the HLA-A*0201. The soluble disulfide-linked reference gp100 TCR has a similar affinity ($K_D$) for the YLEPGPVTV (SEQ ID NO: 6)-HLA*0201 complex (approximately 19 μM) to that obtained for the gp100 YLEPGPVTA (SEQ ID NO: 1)-HLA*0201 complex.

Kinetic Parameters

The above BIAcore analysis methods were also used to determine equilibrium binding constants and off-rates.

For high affinity TCRs (see Example 4 below) $K_D$ was determined by experimentally measuring the dissociation rate constant, $k_{off}$, and the association rate constant, $k_{on}$. The equilibrium constant $K_D$ was calculated as $k_{off}/k_{on}$.

TCR was injected over two different cells one coated with ~300 RU of specific YLEPGPVTA (SEQ ID NO: 1) HLA-A*02 complex (or YLEPGPVTV (SEQ ID NO: 6) HLA-A*02 complex when specified), the second coated with ~300 RU of non-specific HLA-A2-peptide complex. Flow rate was set at 50 μl/min. Typically 250 μl of TCR at a concentration equivalent to ~10 times the Kn was injected. Buffer was then flowed over until the response had returned to baseline or >2 hours had elapsed. Kinetic parameters were calculated using BIAevaluation software. The dissociation phase was fitted to a single exponential decay equation enabling calculation of half-life.

Example 4

Generation of High Affinity Variants of the Native gp100 TCR

Phage display is one means by which libraries of gp100 TCR variants can be generated in order to identify high affinity mutants. The TCR phage display and screening methods described in (Li et al, (2005) Nature Biotech 23 (3): 349-354) were applied to the reference gp100 TCR of Example 2. All six gp100 TCR CDR regions (which are the same in the reference TCR as in the native TCR, were targeted by mutagenesis and each CDR library panned and screened separately.

TCRs with affinities and/or binding half-lives at least twice that of the reference gp100 TCR (and therefore impliedly at least twice that of the native TCR) were identified, having one or more of alpha chain variable domain amino acid residues 94S, 94T, 94R, 97M, 98M, 98Q, 98G, 98S, 98A or 102D using the numbering shown in SEQ ID NO: 2 and/or one or more of beta chain variable domain amino acid residues 27I, 28F, 29Q, 30K, 31K, 50W, 51A, 51G, 52Q, 52Y, 52T, 53G, 53F, 54N, 54H, 61T, 94L, 95Y, 95H, 95W, 95F, 95S, 95V, 96C, 97E, 97A, 98G, 100Q or 100P using the numbering shown in SEQ ID NO: 3.

Specific examples of the amino acid sequences of the variable regions of the alpha chains (SEQ ID NOs: 7, 8 and 9) and beta chains (SEQ ID NOs: 10, 11, 12, 13, 14, 15, 16, 17, 18, 19, 20, 21, 22, 23, 24, 25, 26, 27, 28, 29, 30, 31, 32, 33, 34 and 35) of high affinity TCRs are shown in FIGS. 3A-C and 4A-Z respectively. These alpha chains are mutated only in CDR3 and the beta chains are mutated in one or more of CDR1, CDR2 and CDR3.

TCR heterodimers were refolded using the method of Example 2 above (including the introduced cysteines in the constant regions to provide the artificial inter-chain disulphide bond). In that way TCRs were prepared, consisting of (a) the reference TCR beta chain, together with alpha chains mutated to include the variable domains SEQ ID NOs: 7, 8 and 9; (b) the reference TCR alpha chain together with reference TCR beta chains mutated to include the beta chain variable domains SEQ ID NOs: 10, 11, 12, 13, 14, 15, 16, 17, 18, 19, 20, 21, 22, 23, 24, 25, 26, 27, 28, 29, 30, 31, 32, 33, 34 and 35; and (c) various combinations of beta and alpha chains including the mutant variable domains.

The interaction between these high affinity soluble disulfide-linked gp 100 TCRs and the native peptide YLEPGPVTA (SEQ ID NO: 1) HLA-A*02 complex was analysed using the BIAcore method described above, and the binding data is shown in Table 1. Table 1 A shows the binding data for these high affinity TCRs when tested against the variant peptide YLEPGPVTV (SEQ ID NO: 6) HLA-A *02 complex.

The interaction between these high affinity soluble disulfide-linked gp100 TCRs and the YLEPGPVTV HLA-A*02 complex was analysed using the BIAcore method described above, and the binding data is shown in Table 2.

TABLE 1

| TCR variable domain SEQ ID | | | | | |
|---|---|---|---|---|---|
| A | β | $k_{off}(s^{-1})$ | T½ | $k_{on}(M^{-1}s^{-1})$ | $K_D$ |
| 2 (1-109) | 10 | 2.47e-3 | 4.6 min | 4.77e5 | 5.18 nM |
| 2 (1-109) | 13 | 0.0109 | 63 sec | 2.88e5 | 37.8 nM |
| 2 (1-109) | 14 | 4.71e-3 | 2.4 min | 3.2e5 | 14.7 nM |
| 2 (1-109) | 16 | 3.13e-3 | 3.6 min | 2.84e5 | 11 nM |
| 2 (1-109) | 17 | 5.82e-3 | 1.9 min | 2.99e5 | 19.5 nM |
| 2 (1-109) | 18 | 3.84e-3 | 2.9 min | 6.54e4 | 58.7 nM |
| 2 (1-109) | 19 | 3.41e-3 | 3.3 min | 1.25e5 | 27.2 nM |
| 2 (1-109) | 20 | 0.0133 | 52 sec | 3.44e5 | 38.7 nM |

TABLE 1A binding data for the gp100 TCRs from table 1 tested against the gp100 variant peptide-HLA-A2 complex

| TCR variable domain SEQ ID | | | | | |
|---|---|---|---|---|---|
| A | β | $k_{off}(s^{-1})$ | T½ | $k_{on}(M^{-1}s^{-1})$ | $K_D$ |
| 2 (1-109) | 10 | 2.33e-3 | 4.9 min | 4e5 | 5.83 nM |
| 2 (1-109) | 13 | 0.0102 | 67 sec | 3.05e5 | 33.4 nM |
| 2 (1-109) | 14 | 4.47e-3 | 2.57 min | 3.71e5 | 12 nM |
| 2 (1-109) | 16 | 3.02e-3 | 3.8 min | 3.16e5 | 9.5 nM |
| 2 (1-109) | 17 | 5.81e-3 | 1.98 min | 2.32e5 | 25 nM |
| 2 (1-109) | 18 | 3.56e-3 | 3.2 min | 8.96e4 | 39.7 nM |
| 2 (1-109) | 19 | 3.33e-3 | 3.4 min | 3.53e5 | 9.44 nM |
| 2 (1-109) | 20 | 0.0124 | 56 sec | 2.78e5 | 44.6 nM |

Tables 1 and 1A above show that very similar kinetic parameters were obtained, within experimental error, for each high affinity TCR tested against either the natural gp 100 YLEPGPVTA (SEQ ID NO: 1) peptide HLA-A*02 complex or the variant gp100 YLEPGPVTV (SEQ ID NO: 6) peptide HLAA *02 complex. Following this observation, some high affinity TCRs were only tested against the variant YLEPGPVTV (SEQ ID NO: 6) peptide HLA-A *02 complex (see table 2). It is expected that these TCRs present very similar kinetic parameters for the natural peptide HLA-A *02 complex.

TABLE 2

| TCR variable domain SEQ ID | | | | | |
|---|---|---|---|---|---|
| A | β | $k_{off}(s^{-1})$ | $T\frac{1}{2}$ | $k_{on}$ ($M^{-1}s^{-1}$) | $K_D$ |
| 2 (1-109) | 22 | 7.05e-4 | 16.3 min | 1.72e5 | 4.1 nM |
| 2 (1-109) | 23 | 5.6e-4 | 20.5 min | 3.28e5 | 1.7 nM |
| 2 (1-109) | 24 | 9.93e-5 | 115 min | 4.87e5 | 0.2 nM |
| 7 | 20 | 2.85e-3 | 4 min | 4.55e5 | 6.2 nM |
| 8 | 20 | 2.49e-3 | 4.6 min | 4.36e5 | 5.7 nM |
| 9 | 20 | 2.82e-3 | 4 min | 5.33e5 | 5.3 nM |
| 8 | 25 | 2.35e-5 | 8 h | 6.21e5 | 37 pM |
| 8 | 26 | 3.75e-5 | 5 h | 4.47e5 | 83 pM |
| 8 | 27 | 6.7e-6 | 28 h | 5.31e5 | 12 pM |
| 7 | 3 (1-112) | 0.99 | 0.7 sec | 1.25e5 | 7.9 μM |
| 8 | 3 (1-112) | 0.79 | 0.88 sec | 1.97e5 | 4 μM |
| 9 | 3 (1-112) | 0.96 | 0.72 sec | 2.08e5 | 4.6 μM |
| 2 (1-109) | 26 | 5.6e-5 | 2.7 h | 1.7e5 | 320 pM |
| 2 (1-109) | 28 | 0.082 | 8.5 sec | 7.4e4 | 1.1 μM |
| 2 (1-109) | 29 | 0.122 | 5.7 sec | 6.5e4 | 1.9 μM |
| 2 (1-109) | 30 | 0.194 | 3.6 sec | 7.5e4 | 2.6 μM |
| 2 (1-109) | 31 | 0.54 | 1.3 sec | 6.4e4 | 8.4 μM |
| 2 (1-109) | 32 | 0.385 | 1.8 sec | 2.9e4 | 13.4 μM |
| 2 (1-109) | 33 | 5.75e-2 | 12.1 sec | 2.56e5 | 0.225 μM |
| 2 (1-109) | 34 | 6.3e-3 | 110.5 sec | 2.38e5 | 26 nM |
| 2 (1-109) | 35 | 0.01 | 69.3 sec | 1.96e5 | 51 nM |

Note:
In the above Table the TCRs with variable domain SEQ ID NO: 8 had variable amino acid X as S. However, the variants with variable amino acid X as A had essentially similar $T_{1/2}$ and $K_D$.

Example 5

In-Vitro Cell Staining Using High Affinity gp100 TCR

The following assay was carried out to demonstrate that the soluble high affinity gp100 TCR of Example 4 having the Vα SEQ ID NO: 8 (X=S) and the Vβ SEQ ID NO: 27 was capable of staining T2 cells pulsed with the variant YLEPGPVTV (SEQ ID NO: 6) peptide.

For the purpose of this example, a biotin tag was fused to the C-terminal end of the constant domain of the gp100 beta chain having the Vβ SEQ ID NO: 27 and the whole gene (Vβ Cβ biotin tag inserted into a pGMT7-based expression plasmid. The TCR beta chain-biotin tag was expressed using the method described in Example 2. The αβTCR-biotin tag was refolded using the method described in Example 2. The refolded TCR was purified in a first anion exchange step using the method as described in Example 2. The TCR was then biotinylated using the method described in Example 3. Finally, the biotinylated TCR was purified using a GE Healthcare Superdex 75HR gel filtration column as described in Example 2.

Reagents

R10Assay media: 10% FCS (heat-inactivated, Gibco, cat#10108-165), 88% RPMI 1640 (Gibco, cat#42401-018), 1% glutamine (Gibco, cat#25030-024) and 1% penicillin/streptomycin (Gibco, cat#15070-063).

FACS buffer: PBS/0.5% BSA (Promega, cat#W3841), 2 mM EDTA

Microscopy buffer: PBS/0.5% BSA (Promega, cat#W3841), 400 μM $CaPO_4$, 400 μM $MgPO_4$ Flow Cytometry Method T2 lymphoblastoid cells were pulsed with a variant gp100 peptide (YLEPGPVTV (SEQ ID NO: 6)) or an irrelevant peptide (ELAGIGILTV (SEQ ID NO: 43)) at a range of concentrations ($10^{-7}$ to $10^{-9}$ M) for at least 90 minutes at 37° C./5% $CO_2$ in R10 media.

After pulsing, cells were washed 3 times in FACS buffer and $1 \times 10^6$ cells were incubated with high affinity biotinylated gp100 TCR (5 μg/ml) for 30 minutes at room temperature, washed twice with FACS buffer, and incubated with streptavidin-PE (5 μg/ml: BD biosciences, cat#349023) for 20 minutes at room temperature. After washing with FACS buffer, bound high affinity gp100 TCR was quantified by flow cytometry using a Beckman Coulter FC500 flow cytometer. Controls using peptide-pulsed T2 cells were included in which the gp100 TCR was omitted, or an irrelevant TCR was added.

Results

Staining of T2 cells pulsed with between $10^{-9}$ M to $10^{-7}$ M YLEPGPVTV (SEQ ID NO: 6) variant gp100 peptide by the soluble high affinity gp100 TCR was successfully demonstrated. See FIG. 5A for flow cytometry histograms demonstrating test versus control staining of peptide-pulsed T2 cells. (The filled curves being the "no TCR" controls)

Microscopy Method

The staining of variant peptide YLEPGPVTV (SEQ ID NO: 6)-pulsed T2 cells was visualised by fluorescence microscopy using the high-affinity biotinylated gp100 TCR. Pulsing and staining of T2 cells was carried out as described in "flow cytometry" above. Following staining and washing, the $3 \times 10^4$ cells were washed once more in R10 (without phenol red) and finally resuspended in 400 μl of R10 (without phenol red) and transferred to chambered glass cover slides (Nunc, Lab-tek, cat#155411) and allowed to settle prior to 3-dimensional fluorescence microscopy.

Fluorescent microscopy was carried out using an Axiovert 200M (Zeiss) microscope with a 63× Oil objective (Zeiss). A Lambda LS light source containing a 300W Xenon Arc lamp (Sutter) was used for illumination, and light intensity was reduced to optimal levels by placing a 0.3 and a 0.6 neutral density filter into the light path. Excitation and emission spectra were separated using a TRITC/DiI filter set (Chroma). Cells were imaged in three dimensions by z-stack acquisition (21 planes, 1 μm apart). Image acquisition and analysis was performed using Metamorph software (Universal Imaging) as described (Irvine et al., (2002) *Nature* 419 (6909): 845-9, and Purbhoo et al., *Nature Immunology* 5 (5): 524-30.)

Results

Figure 5B:
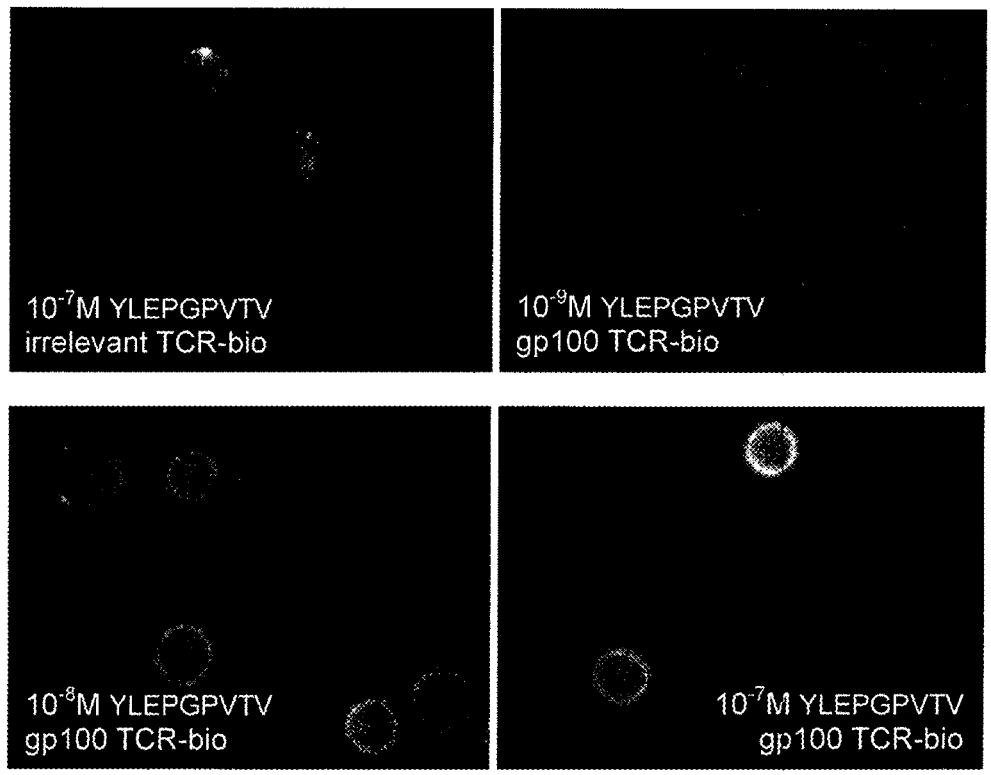
FIG. 5B shows microscopy images of the staining of T2 cells pulsed with the YLEPGPVTV (SEQ ID NO: 6) variant gp100 peptide by a high affinity gp100 TCR.

FIG. 5B shows the successful binding of the high affinity biotinylated gp100 TCR to T2 cells pulsed with the YLEPGPVTV (SEQ ID NO: 6) peptide.

Example 6

Expression, Refolding and Purification of Soluble Anti-CD3 scFv-gp100 TCR Fusion SEQ ID NO: 36 (FIG. 6) is the amino acid sequence of an anti-CD3 scFv antibody fragment (bold type) fused via a linker namely GGGGS SEQ ID NO: 48 (underlined) at the N-terminus of a gp100 TCR β chain, but without the leading introduced methionine for efficient initiation of protein synthesis. The gp100 TCR β chain contains the variable domain SEQ ID NO: 27.

The gp100 TCR α chain of the TCR fusion in this example contains the variable domain SEQ ID NO: 8 (FIG. 3B) with X=S.

The construct above was prepared as follows:

Ligation

Synthetic genes encoding (a) the TCR Vα chain and (b) the fusion sequence SEQ ID NO: 36 wherein amino acids at positions 1 and 2 are D and I respectively, were separately ligated into pGMT7+Cα (having an introduced cysteine enabling formation of a disulfide bond) vector and pGMT7-based expression plasmid respectively, which contain the T7 promoter for high level expression in *E. coli* strain Rosetta (DE3)pLysS (Pan et al., *Biotechniques* (2000) 29 (6): 1234-8). Note that a leading methionine was introduced at the N-terminus of the TCR alpha chain variable domain and at the N-terminus of the fusion sequence SEQ ID NO: 36 to allow efficient initiation of protein synthesis in bacteria.

Expression

The expression plasmids were transformed separately into *E. coli* strain Rosetta (DE3)pLysS, and single ampicillin-resistant colonies were grown at 37° C. in TYP (ampicillin 100 μg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNase. Inclusion body pellets were recovered by centrifugation for 30 minutes at 4,000 rpm. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA,) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C.

Refolding

Approximately 20 mg of TCR α chain and 40 mg of scFv-TCR β chain solubilised inclusion bodies were thawed from frozen stocks, diluted into 20 ml of a guanidine solution (6 M Guanidine-hydrochloride, 50 mM Tris HCl pH 8.1, 100 m NaCl, 10 mM EDTA, 20 mM DTT), and incubated in a 37° C. water bath for 30 min-1 hr to ensure complete chain denaturation. The guanidine solution containing fully reduced and denatured TCR chains was then injected into 1 liter of the following refolding buffer: 100 mM Tris pH 8.1, 400 mM L-Arginine, 2 mM EDTA, 5 M Urea. The redox couple (cysteamine hydrochloride and cystamine dihydrochloride (to final concentrations of 10 mM and 1 mM, respectively)) were added approximately 5 minutes before addition of the denatured TCR α and scFv-TCR β chains. The solution was left for ~30 minutes. The refolded scFv-TCR was dialysed in dialysis tubing cellulose membrane (Sigma-Aldrich; Product No. D9402) against 10 L $H_2O$ for 18-20 hours. After this time, the dialysis buffer was changed twice to fresh 10 mM Tris pH 8.1 (10 L) and dialysis was continued at 5° C.±3° C. for another ~8 hours. Soluble and correctly folded scFv-TCR was separated from degradation products and impurities by a 3-step purification method as described below.

First Purification Step

The dialysed refold (in 10 mM Tris pH8.1) was loaded onto a POROS 50HQ anion exchange column and the bound protein eluted with a gradient of 0-500 mM NaCl over 6 column volumes using an Akta purifier (GE Healthcare). Peak fractions (eluting at a conductivity ~20 mS/cm) were stored at 4° C. Peak fractions were analysed by Instant Blue Stain (Novexin) stained SDS-PAGE before being pooled.

Second Purification Step: Cation Exchange Purification

The anion exchange pooled fractions were buffer exchanged by dilution with 20 mM MES pH6-6.5, depending on the pI of the scFv-TCR fusion. The soluble and correctly folded scFv-TCR was separated from misfolded, degradation products and impurities by loading the diluted pooled fractions (in 20 mM MES pH6-6.5) onto a POROS 50HS cation exchange column and eluting bound protein with a gradient of 0-500 mM NaCl over 6 column volumes using an Akta purifier (GE Healthcare). Peak fractions (eluting at a conductivity ~10 mS/cm) were stored at 4° C.

Final Purification Step

Peak fractions from second purification step were analysed by Instant Blue Stain (Novexin) stained SDS-PAGE before being pooled. The pooled fractions were then concentrated for the final purification step, when the soluble scFv-TCR was purified and characterised using a Superdex S200 gel filtration column (GE Healthcare) pre-equilibrated in PBS buffer (Sigma). The peak eluting at a relative molecular weight of approximately 78 kDa was analysed by Instant Blue Stain (Novexin) stained SDS-PAGE before being pooled.

The construct prepared according to the above Example 6 may be varied by substituting the GGGGS SEQ ID NO: 48 linker sequence with an alternative linker sequence, for example selected from GGGSG SEQ ID NO: 49, GGSGG SEQ ID NO: 50, GSGGG SEQ ID NO: 51, and GGEGGG-SEGGGS SEQ ID NO: 47, and/or by substituting amino acid D1 of SEQ ID NO: 36 by A, and/or substituting amino acid 12 of SEQ ID NO: 36 by Q, and/or by substituting amino acid 51 of SEQ ID NO: 8 by A or G. In another variation, the beta variable domain sequence forming part of SEQ ID NO: 36 may be changed from SEQ ID NO: 27 to SEQ ID NOs: 13, 17, 23 or 26.

Example 7

Non-Radioactive Cytotoxicity Assay

This assay is a colorimetric alternative to $^{51}Cr$ release cytotoxicity assays and quantitatively measures lactate dehydrogenase (LDH) which is an enzyme that is released upon cell lysis. Released LDH in culture supernatants is measured with a 30-minute coupled enzymatic assay, which results in the conversion of a tetrazolium salt (INT) into a red formazan product. The amount of colour formed is proportional to the number of lysed cells. The absorbance data is collected using a standard 96-well plate reader at 490 nm.

Materials

CytoTox96® Non-Radioactive Cytotoxicity Assay (Promega) (G1780) contains Substrate Mix, Assay Buffer, Lysis Solution, and Stop Solution Assay media: 10% FCS (heat-inactivated, Gibco, cat#10108-165), 88% RPMI 1640 without phenol red (Invitrogen, cat#32404014), 1% glutamine, 200 mM (Invitrogen, cat#25030024), 1% penicillin/streptomycin (Invitrogen cat#15070063)

Nunc microwell round bottom 96 well tissue culture plate (Nunc, cat#163320)

Nunc-Immuno plates Maxisorb (Nunc, cat#442404)

Method

Target Cell Preparation

The targets cells used in this assay were from the tumour cell lines Mel526 (melanoma cell line HLA-A2$^+$ gp100$^+$) and A375 (melanoma cell line HLA-A2$^+$ gp100$^-$). Target cells were prepared in assay medium: target cell concentration was adjusted to 2×10⁵ cells/ml to give 1×10⁴ cells/well in 500.

Effector Cell Preparation

The effector cells used in this assay were PBMCs (peripheral blood mononuclear cells). The effector to target ratio used was 50:1 (1×10⁷ cells/ml to give 5×10⁵ cells/well in 50 µl).

Reagent/Test Compound Preparation

Varying concentrations of the anti-CD3 scFv-gp100 TCR fusion (from 30 nM to 0.03 pM) were prepared by dilution into assay media. The anti-CD3 scFv-gp100 TCR fusion was prepared according to Example 6.

Assay Preparation

The constituents of the assay were added to the plate in the following order:
50 µl of target cells (prepared as explained previously) to each well
50 µl of effector cells (prepared as explained previously) to each well
50 µl of reagent (prepared as explained previously) to each well.
Several controls were prepared as explained below:
Effector spontaneous release: 50 µl effector cells alone.
Target cells spontaneous release: 50 µl target cells alone.
Target maximum release: 50 µl target cells alone.
Assay medium control: 150 µl medium alone.
Assay medium volume control for lysis solution: 150 µl medium alone.
All wells are prepared in triplicate in a final volume of 150 µl.

The plate was centrifuged at 250×g for 4 minutes then incubated at 37° C. for 24 hours. Forty-five minutes prior to supernatant harvest, 15 µl of lysis solution was added to Target cell maximum release and to Assay medium volume control wells.

The plate was centrifuged at 250×g for 4 minutes. 50 µl of the supernatant from each well of the assay plate was transferred to the corresponding well of a flat-bottom 96 well Nunc Maxisorb plate. The Substrate Mix was reconstituted using Assay Buffer (12 ml). 50 µl of the reconstituted Substrate Mix was then added to each well of the plate. The plate was covered with aluminium foil and incubated at room temperature for 30 minutes. 50 µl of Stop Solution was added to each well of the plate to stop the reaction. The absorbance at 490 nm was recorded on an ELISA plate reader within one hour after the addition of Stop Solution.

Calculation of Results

The average of absorbance values of the Culture Medium Background was subtracted from all absorbance values of Experimental, Target Cell Spontaneous Release and Effector Cell Spontaneous Release.

The average of the absorbance values of the Volume Correction Control was subtracted from the absorbance values obtained for the Target Cell Maximum Release Control.

The corrected values obtained in the first two steps were used in the following formula to compute percent cytotoxicity:

% cytotoxicity=100×(Experimental−Effector Spontaneous−Target Spontaneous)/(Target Maximum−Target Spontaneous)

Results

The graph in FIG. 7 shows the specific killing of melanoma cells by T cells redirected by the anti-CD3 scFv-gp100 high affinity TCR (prepared as explained at example 6) specifically binding to gp100 presenting cells (Mel526 cells).

Example 8

Transfection of T-Cells with High Affinity Variants of the Native gp100 TCR (a) Lentiviral Vector Preparation by Express-in-Mediated Transient Transfection of 293T Cells A 3$^{rd}$ generation lentiviral packaging system is used to package lentiviral vectors containing the gene encoding the desired TCR. 293T cells are transfected with 4 plasmids (one lentiviral vector containing the TCR alpha chain-P2A-TCR beta chain single ORF gene described in Example 8c, and 3 plasmids containing the other components necessary to construct infective but non-replicative lentiviral particles) using Express-In-mediated transfection (Open Biosystems).

For transfection take one T150 flask of 293T cells in exponential growth phase, with cells evenly distributed on the plate, and slightly more than 50% confluent. Bring Express-In aliquots to room temperature. Place 3 ml Serum-Free Medium (RPMI 1640+10 mM HEPES) in a sterile 15 ml conical tube. Add 174 µl of Express-In Reagent directly into the Serum-Free Medium (this provides for a 3.6:1 weight ratio of Reagent to DNA). Mix thoroughly by inverting tubes 3-4 times and incubate at room temperature for 5-20 minutes.

In a separate 1.5 ml microtube, add 15 µg plasmid DNA to premixed packaging mix aliquots (containing 18 µg pRS-V.REV (Rev expression plasmid), 18 µg pMDLg/p.RRE (Gag/Pol expression plasmid), 7 µg pVSV-G (VSV glycoprotein expression plasmid), usually ~22 µl, and pipette up and down to ensure homogeneity of the DNA mix. Add ~1 ml of Express-In/Serum-Free Medium to the DNA mix drop wise then pipette up and down gently before transferring back to the remainder of the Express-In/Serum-Free Medium. Invert tube 3-4 times and incubate at room temperature for 15-30 minutes.

Remove old culture medium from flask of cells. Add Express-In/medium/DNA (3 ml) complex to flask direct into the bottom of an upright flask of 293T cells. Slowly place flask flat to cover cells and very gently rock the flask to ensure even distribution. After 1 minute add 22 ml fresh culture medium ($R_{10}$+HEPES: RPMI 1640, 10% heat-inactivated FBS, 1% Pen/Strep/L-glutamine, 10 mM HEPES) and carefully return to incubator. Incubate overnight at 37° C./5% $CO_2$. After 24 hours, proceed to harvest the medium containing packaged lentiviral vectors.

To harvest the packaged lentiviral vectors, filter the cell culture supernatent through a 0.45 micron nylon syringe filter, centrifuge the culture medium at 10,000 g for 18 hours (or 112,000 g for 2 hours), remove most of the supernatant (taking care not to disturb the pellet) and resuspend the pellet in the remaining few ml of supernatant (usually about 2 ml from a 31 ml starting volume per tube). Snap freeze on dry ice in 1 ml aliquots and store at −80° C.

(b) Transduction of T Cells with Packaged Lentiviral Vectors Containing Gene of Interest Prior to transduction with the packaged lentiviral vectors, human T cells (CD8 or CD4 or both depending on requirements) are isolated from the blood of healthy volunteers. These cells are counted and incubated overnight in $R_{10}$ containing 50 U/ml IL-2 at 1×10⁶ cells per ml (0.5 ml/well) in 48 well plates with pre-washed anti-CD3/CD28 antibody-coated microbeads (Dynal T cell expander, Invitrogen) at a ratio of 3 beads per cell.

After overnight stimulation, 0.5 ml of neat packaged lentiviral vector is added to the desired cells. Incubate at 37° C./5% $CO_2$ for 3 days. 3 days post-transduction count cells and dilute to $0.5 \times 10^6$ cells/ml. Add fresh medium containing IL-2 as required. Remove beads 5-7 days post-transduction. Count cells and replace or add fresh medium containing IL-2 at 2 day intervals. Keep cells between $0.5 \times 10^6$ and $1 \times 10^6$ cells/ml. Cells can be analysed by flow cytometry from day 3 and used for functional assays (e.g. ELISPOT for IFNγ release) from day 5. From day 10, or when cells are slowing division and reduced in size, freeze cells in aliquots of at least $4 \times 10^6$ cells/vial (at $1 \times 10^7$ cells/ml in 90% FBS/10% DMSO) for storage.

(c) Wild Type (Wt) TCR Gene for T-Cell Transfection by Methods (a) and (b) Above FIG. 8A is a DNA sequence (SEQ ID NO: 37) encoding the native gp100 TCR (codon-optimised for maximal human cell expression). It is a full length alpha chain (TRAV17)-Porcine teschovirus-12A-full length beta chain (TRBV19) single open reading frame construct. The 2A sequence is underlined, and is preceded by nucleotides encoding a furin cleavage site to assist proteolytic removal of the 2A sequence (discussed further below in relation to FIG. 8B (SEQ ID No 38). Peptide bond skipping during protein translation of the mRNA at the 3' end of the 2A sequence produces two proteins: 1) alpha TCR chain-2A fusion. 2) beta TCR chain. SEQ ID NO: 37 (FIG. 8A) includes NheI and SalI restriction sites (underlined).

FIG. 8B is the amino acid sequence (SEQ ID NO: 38) corresponding to FIG. 8A

In FIG. 8B:
M1-N20 is a leader sequence which is removed on maturation of the wild type alpha chain TCR;
S21-S223 corresponds to the wild type alpha chain sequence SEQ ID NO: 2;
S21-R250 corresponds to the wild type alpha chain extracellular domain;
I251-L267 is the alpha chain transmembrane region of the mature TCR;
W268-S270 is the alpha chain intracellular region of the mature TCR;
R273-R276 is the furin cleavage site to assist proteolytic removal, in the Golgi apparatus, of the P2A sequence A281-P299;
G271, S272, S277 to G280, R300 are flexible linkers allowing full function of furin cleavage and P2A sequences;
M301-V319 is a leader sequence which is removed on maturation of the wild type beta chain TCR;
D320-D561 corresponds to the wild type beta chain sequence SEQ ID NO: 3;
D320-E581 corresponds to the wild type beta chain extracellular domain;
I582-V603 is the beta chain transmembrane region of the mature TCR;
K604-G610 is the beta chain intracellular region of the mature TCR.

(d) T-Cells Transfected with Wild Type and High Affinity gp100 TCRs

Following the procedures described in (a) and (b) above, the gp100 alpha wt-2A-beta wt TCR gene (SEQ ID No 37 (FIG. 8A)) was inserted into the pELNSxv lenti vector using the NheI and SalI restriction sites unique to both DNA constructs, and transfected T-cells created.

Similarly, T-cells may be created by transfection with genes identical to SEQ ID No 37 (FIG. 8A) except that they encode (a) TCRs with the variable domain sequence (S1 to A109) of the wild type alpha chain SEQ ID No 2, associated with a beta chain variable domain having one of SEQ ID NOs: 10-35; or (b) an alpha chain variable domain having one of SEQ ID NOs: 7-9 associated with the variable domain sequence (D1 to T112) of the wild type beta chain SEQ ID No 3; or (c) an alpha chain variable domain having one of SEQ ID NOs: 7-9 associated with a beta chain variable domain having one of SEQ ID NOs: 10-35.

Example 9

Increased Activation of gp100 Improved-Affinity TCR-Transduced T Cells Compared to Wild Type-Affinity TCR-Transduced T Cells in Response to Tumour Cell Lines ELISPOT Protocol The following assay was carried out to demonstrate the activation of TCR-transduced cytotoxic T lymphocytes (CTLs) in response to tumour cell lines. IFN-γ production, as measured using the ELISPOT assay, was used as a read-out for cytotoxic T lymphocyte (CTL) activation.

Reagents

Assay media: 10% FCS (Gibco, Cat#2011-09), 88% RPMI 1640 (Gibco, Cat#42401), 1% glutamine (Gibco Cat#25030) and 1% penicillin/streptomycin (Gibco Cat#15070-063).

Wash buffer: 0.01 M PBS/0.05% Tween 20

PBS (Gibco Cat#10010)

The Human IFNγ ELISPOT PVDF-Enzymatic kit (Diaclone, France; Cat#856.051.020) contains all other reagents required. (Capture and detection antibodies, skimmed milk powder, BSA, streptavidin-alkaline phosphatase and BCIP/NBT solution as well as the Human IFN-γ PVDF ELISPOT 96 well plates)

Method

Target Cell Preparation

The target cells used in this method were natural epitope-presenting cells: Mel526 melanoma, Mel624 melanoma, MeWo and SKMel5 which are all HLA-A2$^+$ gp100$^+$. A375 melanoma (HLA-A2$^+$ gp100$^-$) was used as a negative control cell line. HLA-A2$^+$ human primary hepatocytes (lot HEP2, obtained from ScienCell) were determined to be gp100$^-$ (gp100 mRNA expression was not detected by RT-PCR) and were used as a negative control. Sufficient target cells (50,000 cells/well) were washed by centrifugation three times at 1200 rpm, 10 minutes in a Megafuge 1.0 (Heraeus). Cells were then re-suspended in assay media at $10^6$ cells/ml.

Effector Cell Preparation

The effector cells (T cells) used in this method were a 1:1 mix of CD4+ and CD8+ T cells (obtained by negative selection (using the CD4 and CD8 Negative Isolation Kits, Dynal) from PBL). Cells were stimulated with antiCD3/CD28 coated beads (T cell expander, Invitrogen), transduced with lentiviruses carrying the gene encoding the full αβ TCR of interest (based on the construct described in Example 8 and shown in FIG. 8B) and expanded in assay media containing 50 U/ml IL-2 until between 10 and 13 days post transduction. These cells were then placed in assay media prior to washing by centrifugation at 1200 rpm, 10 minutes in a Megafuge 1.0 (Heraeus). Cells were then re-suspended in assay media at a 4× the final required concentration.

ELISPOTs

Plates were prepared as follows: 100 µl anti-IFN-γ capture antibody was diluted in 10 ml sterile PBS per plate. 100 µl of the diluted capture antibody was then aliquoted into each well. The plates were then incubated overnight at 4° C. Following incubation the plates were washed (programme 1, plate type 2, Ultrawash Plus 96-well plate washer; Dynex) to remove the capture antibody. Plates were then blocked by adding 100 μl 2% skimmed milk in sterile PBS to each well and incubating the plates at room temperature for two hours. The skimmed milk was then washed from the plates (programme 1, plate type 2, Ultrawash Plus 96-well plate washer, Dynex) and any remaining wash buffer was removed by flicking and tapping the ELISPOT plates on a paper towel.

The constituents of the assay were then added to the ELISPOT plate in the following order:
- 50 μl of target cells $10^6$ cells/ml (giving a total of 50,000 target cells/well).
- 50 μl of soluble high affinity gp100 TCR can be added (at 1.2 μM to give 300 nM final concentration) to block the gp100-specific activation of TCR-transduced T cells.
- Media sufficient to give 200 ul per well final volume (assay media).
- 50 μl effector cells (5,000 mixed CD4/8$^+$ cells/well).

The plates were then incubated overnight (37° C./5% $CO_2$). The next day the plates were washed three times (programme 1, plate type 2, Ultrawash Plus 96-well plate washer, Dynex) with wash buffer and tapped on paper towel to remove excess wash buffer. 100 μl primary detection antibody was then added to each well. The primary detection antibody was prepared by adding 550 μl of distilled water to a vial of detection antibody supplied with the Diaclone kit. 100 μl of this solution was then diluted in 10 ml PBS/1% BSA (the volume required for a single plate). Plates were then incubated at room temperature for at least 2 hr prior to being washed three times (programme 1, plate type 2, Ultrawash Plus 96-well plate washer, Dynex) with wash buffer, excess wash buffer was removed by tapping the plate on a paper towel.

Secondary detection was performed by adding 100 μl of diluted streptavidin-Alkaline phosphatase to each well and incubating the plate at room temperature for 1 hour. The streptavidin-Alkaline phosphatase was prepared by addition of 10 μl streptavidin-Alkaline phosphatase to 10 ml PBS/1% BSA (the volume required for a single plate). The plates were then washed three times (programme 1, plate type 2, Ultrawash Plus 96-well plate washer, Dynex) with wash buffer and tapped on paper towel to remove excess wash buffer. 100 μl of BCIP/NBT solution, as supplied with the Diaclone kit, was then added to each well. During development plates were covered in foil and left for 5-15 min. Developing plates were regularly checked for spots during this period to determine optimal time to terminate the reaction. The plates were washed in a sink full of tap water to terminate the development reaction, and shaken dry prior to their disassembly into their three constituent parts. The plates were then dried at 50° C. for 1 hr prior to counting the spots that have formed on the membrane using an Immunospot Plate reader (CTL; Cellular Technology Limited).

Results

IFNγ release by activated TCR-transduced T cells in response to a variety of gp100-positive and control tumour cell lines or control hepatocytes was tested by ELISPOT assay (as described above). The number of ELISPOT spots observed in each well was plotted using Prism (Graph Pad).

Mixed CD4$^+$/CD8$^+$ T cells expressing a) TCR NO: 1 (amino acid sequence SEQ ID NO: 38), b) TCR NO: 2 or c) TCR NO: 3, based on the construct described in Example 8 and shown in FIG. 8B, but having the TCR alpha chain and beta chain variable domains as described in the table below, were incubated with gp100$^+$ HLA-A2$^+$ tumour cell lines Mel526, Mel624, SKMel5, or MeWo or with gp100$^-$ HLA-A2$^+$ A375 or HEP2. gp100-specific blocking was performed by addition of 300 nM of the gp100 TCR of Example 4 (prepared as described in Example 2) having the Vα SEQ ID NO: 8 and the Vβ SEQ ID NO: 27.

| TCR No | TCR α variable domain SEQ ID NO: | TCR β variable domain SEQ ID NO: |
|---|---|---|
| 1 | S1 to A109 of SEQ ID NO: 2 | D1 to T112 of SEQ ID NO: 3 |
| 2 | 8 | D1 to T112 of SEQ ID NO: 3 |
| 3 | S1 to A109 of SEQ ID NO: 2 | 33 |

Figure 9A:
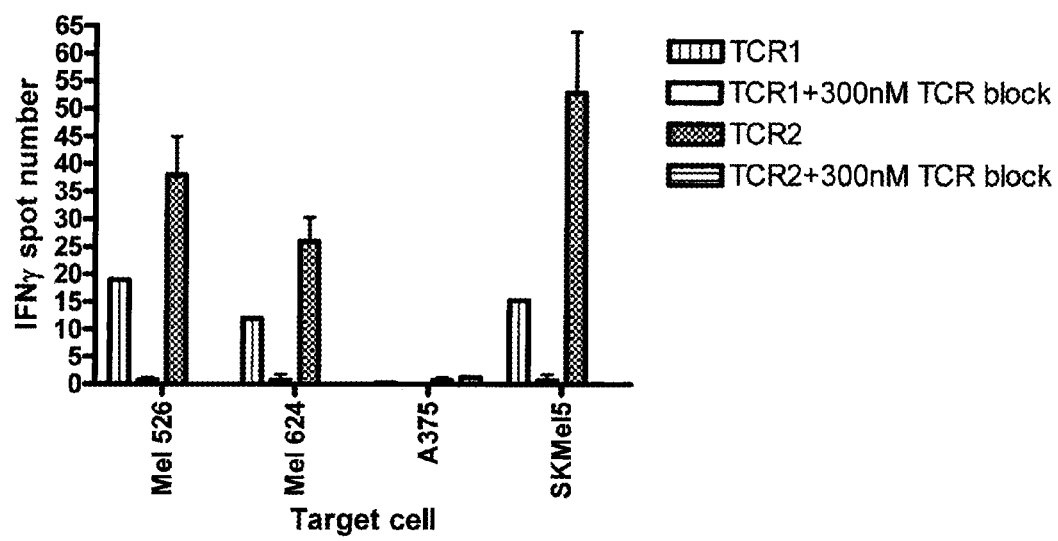
FIGS. 9A and 9B show the IFN-γ release of gp100 TCR-transduced T-cells in response to a range of target cells in an ELISPOT assay. These figures show the increased specific activation of T cells transduced with high affinity gp 100 TCRs compared to T cells transduced with the native gp100 TCR.
Figure 9B:
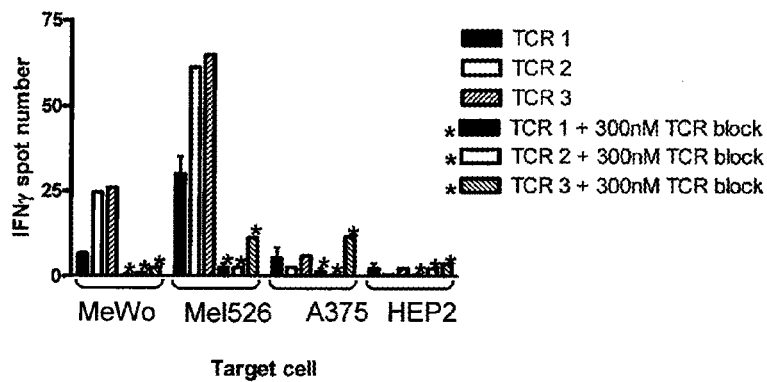

FIG. 9.a demonstrates that TCR NO: 1-transduced T cells released IFNγ in response to Mel526, Mel624 and SKMel5 melanoma lines only, which was effectively blocked by 300 nM of the gp100 TCR of Example 4 having the Vα sequence ID NO: 8 and the Vβ sequence ID NO: 27.

Improved-affinity gp100 TCR NO: 2-transduced T cells showed a greater response to these tumour cell lines, which was effectively blocked by 300 nM of the gp100 TCR of Example 4 having the Vα sequence ID NO: 8 and the Vβ sequence ID NO: 27.

FIG. 9.b demonstrates that TCR NO: 1-transduced T cells released IFNγ in response to Mel526 cells which was effectively blocked by 300 nM of the gp100 TCR. IFNγ release was very poor against MeWo cells.

TCR NO: 2-transduced T cells and TCR NO: 3-transduced T cells showed a greater response to both Mel526 and MeWo cells, which was effectively blocked by 300 nM of the gp100 TCR.

Example 10

Evaluation of the Potency of Several gp100 TCR-Anti-CD3 Fusions Having a Range of TCR Affinities ELISPOT Protocol The following assay was carried out to compare the potency of various gp100 TCR-anti-CD3 fusion proteins in activating cytotoxic T lymphocytes (CTLs) in response to a tumour cell line presenting the gp100 peptide-HLA-A2 complex. IFN-γ production, as measured using the ELISPOT assay, was used as a read-out for T cell activation. The ELISPOT assay is described in previous Example 9.

Reagents

Assay media, wash buffer, PBS and the Human IFNγ ELISPOT PVDF-Enzymatic kit were used as described in Example 9.

Method

Target Cell Preparation

The target cells used in this method were natural epitope-presenting cells Mel526 melanoma cells which are HLA-A2$^+$ gp100$^+$. Sufficient target cells (50,000 cells/well) were washed by centrifugation once at 1200 rpm, 10 min in a Megafuge 1.0 (Heraeus). Cells were then re-suspended in assay media at $10^6$ cells/ml.

Effector Cell Preparation

The effector cells (T cells) used in this method were CD8+ T cells (obtained by negative selection (using the CD8 Negative Isolation Kit, Dynal, Cat#113.19) from PBL). Effector cells were defrosted and placed in assay media prior to washing by centrifugation at 1200 rpm, 10 min in a Megafuge 1.0

(Heraeus). Cells were then resuspended in assay media at a 4× the final required concentration.

Reagent/Test Compound Preparation

Varying concentrations of each gp100 TCR-scFv (from 10 nM to 0.1 pM) were prepared by dilution into assay media to give 4× final concentration. The gp100 TCR-scFv fusions tested are identified in the results section and were prepared as described in Example 6.

ELISPOTs

Plates were prepared as described in Example 9.

The constituents of the assay were then added to the ELISPOT plate in the following order:

50 µl of target cells $10^6$ cells/ml (giving a total of 50,000 target cells/well)

50 µl of reagent (the TCR-anti-CD3 fusions; varying concentrations)

50 µl media (assay media)

50 µl effector cells (5,000 CD8+ cells/well).

The plates were then incubated overnight (37° C./5% CO2). Washing of the plates, preparation of the primary antibody and detection with a primary antibody were performed as explained in Example 9.

Secondary detection and development were performed as explained in Example 9. The plates were then dried at 50° C. for 1 hr prior to counting the spots that have formed on the membrane using an Immunospot Plate reader (CTL; Cellular Technology Limited).

Results

The gp100 TCR-anti-CD3 scFv fusions tested in this example comprise the gp100 TCR alpha chain sequence SEQ ID NO: 45 having the variable domain (amino acids 1 to 109) of SEQ ID NO: 2 (amino acids 1 to 109) or the gp100 TCR alpha chain sequence SEQ ID NO: 45 but having the variable domain (amino acids 1 to 109) of SEQ ID NO: 8 (with X=S), and the gp100 TCR beta chain-anti-CD3 scFv of SEQ ID NO: 36 but wherein amino acids at positions 1 and 2 are D and I respectively, and wherein amino acid residues 108 to 131 are replaced by a variant linker, namely RTSGPGDGGKGG-PGKGPGGEGTKGTGPGG (SEQ ID NO: 44), and amino acid residues 254 to 258 are replaced by a variant linker, namely GGEGGGSEGGGS (SEQ ID NO: 47), having the beta chain variable domain of SEQ ID NO: 27 which can be changed to the variable domain of SEQ ID NO: 3 (D1 to T112 of SEQ ID NO: 3), or to the variable domain of SEQ ID NO: 13, or to the variable domain of SEQ ID NO: 17, or to the variable domain of SEQ ID NO: 23 or to the variable domain of SEQ ID NO: 26, as shown in the table below. The TCR-anti-CD3 fusions were prepared as described in Example 6.

Figure 10:
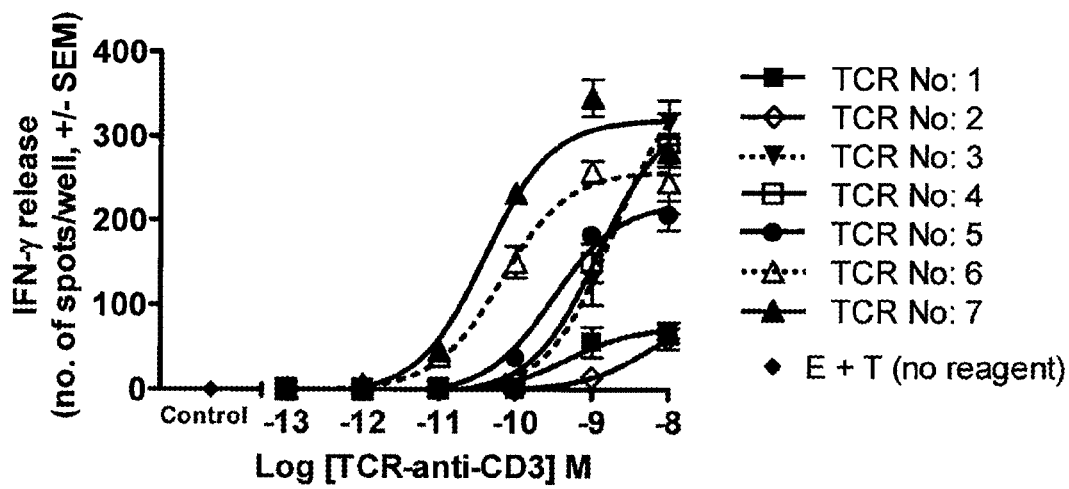
FIG. 10 shows the IFN-γ release of CD8+ T cells activated by different gp100 TCR-anti-CD3 scFv fusions having increasing TCR-pMHC affinities.

The number of ELISPOT spots observed in each well was plotted against the concentration of the fusion construct using Prism (Graph Pad) (see FIG. 10). From these dose-response curves, the EC50 values were determined (EC50 are determined at the concentration of TCR-anti-CD3 fusion that induces 50% of the maximum response).

The graph in FIG. 10 shows the specific activation of CD8+ T cells by the gp100 TCR-anti-CD3 fusions specifically binding to gp100 presenting cells.

The table below shows the $EC_{50}$ of each gp100 TCR-anti-CD3 fusion as well as the improvement in TCR/peptide-HLA affinity compared to the WT TCR (TCR NO: 1).

| TCR No | Alpha chain TCR variable domain SEQ ID | Beta chain TCR variable domain SEQ ID | Affinity improvement | $EC_{50}$ |
|---|---|---|---|---|
| 1 | 2 (1-109) | 3 (1-112) | — | Not determined* |
| 2 | 8 | 3 (1-112) | 3.7 | Not determined* |
| 3 | 2 (1-109) | 13 | 492 | 1.928e−9 |
| 4 | 2 (1-109) | 17 | 698 | 1.232e−9 |
| 5 | 2 (1-109) | 23 | 7,692 | 3.129e−10 |
| 6 | 2 (1-109) | 26 | 93,750 | 6.540e−11 |
| 7 | 8 | 27 | 1,000,000 | 3.995e−11 |

*Note: At the highest concentration of fusion tested, the maximal signal with the WT TCR (TCR NO: 1)-anti-CD3 was less than 20% of the signal observed with TCR NO: 7-anti-CD3 and consequently the $EC_{50}$ value for TCR NO: 1-anti-CD3 was not reliably determinable. At the highest concentration of TCR NO: 2-anti-CD3 fusion tested, the T cell activation did not reach a maximum and consequently the EC50 value was not reliably determinable.

Overall, this experiment indicates that TCR-anti-CD3 fusions with higher affinity TCR moieties give better activation of CD8+ T cells. These results demonstrate a correlation between the affinity of the TCR for the gp100 peptide-HLA-A2 complex and the potency of the TCR-anti-CD3 fusion to activate CD8+ T cells. TCR NO: 7-anti-CD3 fusion demonstrated a superior potency compared to the other TCR fusions tested.

Example 11

T-Cell Redirection Assay Testing the Potency of High Affinity gp100-Anti-CD3 Fusions ELISPOT Protocol The following assay was carried out to compare the potency of various gp100 TCR-anti-CD3 fusion proteins in activating cytotoxic T lymphocytes (CTLs) in response to a tumour cell line presenting the gp100 peptide-HLA-A2 complex. IFN-γ production, as measured using the ELISPOT assay, was used as a read-out for T cell activation.

Reagents

Assay media: 10% FBS (heat-inactivated) (Sera Laboratories International, Cat#EU-000-F1) 88% RPMI 1640 (Invitrogen, Cat#42401018), 1% L-glutamine (Invitrogen, Cat#25030024) and 1% penicillin/streptomycin (Invitrogen, Cat#15070063).

Wash buffer: 0.01 M PBS, one sachet diluted in 1 L deionised water (Sigma, Cat#P3813)/0.05% Tween 20 (Sigma, Cat#P7949)

PBS (Invitrogen, cat#10010015)

Dilution buffer: PBS (Invitrogen, cat#10010015) containing 10% FBS (heat-inactivated) (Sera Laboratories International, cat#EU-000-F1)

The Human IFNγ ELISPOT PVDF-Enzymatic kit (10 plate) (BD; Cat#551849) which includes PVDF ELISPOT 96 well plates, capture antibody, detection antibody and streptavidin-HRP (horse radish peroxidise)

AEC substrate reagent set (BD, cat#551951)

Method

Target Cell Preparation

The target cells used in this method were natural epitope-presenting cells Mel526 melanoma cells which are HLA-A2+ gp100+. A375 melanoma (HLA-A2+ gp100−) was used as a negative control cell line. Sufficient target cells (50,000 cells/well) were washed by centrifugation once at 1200 rpm, 10 min in a Megafuge 1.0 (Heraeus). Cells were then re-suspended in assay media at $10^6$ cells/ml.

Effector Cell Preparation

The effector cells (T cells) used in this method were CD8+ T cells (obtained by negative selection (using the CD8 Negative Isolation Kit, Dynal, Cat#113.19) from PBL). Effector cells were defrosted and placed in assay media prior to washing by centrifugation at 1200 rpm, 5 min in a Megafuge 1.0 (Heraeus). Cells were then resuspended in assay media at $1.6 \times 10^5$ cells per ml to give 8,000 cells per well in 50 µl Reagent/Test Compound Preparation Varying concentrations of each gp100 TCR-scFv (from 10 nM to 0.1 pM) were prepared by dilution into assay media to give 4× final concentration. The gp100 TCR-scFv fusions tested are identified in the results section and were prepared as described in Example 6.

ELISPOTs

Plates were prepared as follows: 50 µl anti-IFN-γ capture antibody was diluted in 10 ml sterile PBS per plate. 100 µl of the diluted capture antibody was then aliquoted into each well. The plates were then incubated overnight at 4° C. Following incubation the plates were then blocked by flicking out capture antibody into the sink, tapping on blue roll to remove residual antibody and then adding 200 µl assay media to each well and incubating the plates at room temperature for two hours. The blocking assay media was removed by flicking the media into the sink and any remaining media was removed by tapping the ELISPOT plates on a paper towel.

The constituents of the assay were then added to the ELISPOT plate in the following order:

50 µl of target cells $10^6$ cells/ml (giving a total of 50,000 target cells/well)

50 µl of reagent (the TCR-anti-CD3 fusions; varying concentrations)

50 µl media (assay media)

50 µl effector cells (8,000 CD8+ cells/well).

The plates were then incubated overnight (37° C./5% CO2). The next day the plates were washed three times (programme 1, plate type 2, Ultrawash Plus 96-well plate washer, Dynex) with wash buffer and tapped on paper towel to remove excess wash buffer. 100 µl primary detection antibody was then added to each well. The primary detection antibody was prepared by adding 40 µl to 10 ml dilution buffer (the volume required for a single plate). Plates were then incubated at room temperature for at least 2 hr prior to being washed three times (programme 1, plate type 2, Ultrawash Plus 96-well plate washer, Dynex) with wash buffer, excess wash buffer was removed by tapping the plate on a paper towel.

Secondary detection was performed by adding 100 µl of diluted streptavidin-HRP to each well and incubating the plate at room temperature for 1 hour. The streptavidin-HRP was prepared by addition of 100 µl streptavidin-HRP to 10 ml dilution buffer (the volume required for a single plate). The plates were then washed three times (programme 1, plate type 2, Ultrawash Plus 96-well plate washer, Dynex) with wash buffer followed by two washes with PBS which was pipetted by hand by adding 200 µl per well and flicking out into the sink. The plate was tapped on paper towel to remove excess PBS. 100 µl of AEC substrate reagent was then added to each well. The substrate was prepared by adding 10 drops of AEC chromogen to 10 ml AEC buffer (the volume required for a single plate). During development plates were covered in foil and left for 5-15 min. Developing plates were regularly checked for spots during this period to determine optimal time to terminate the reaction. The plates were washed with deionised water to terminate the development reaction, and tapped dry prior to their disassembly into their three constituent parts. The plates were then air dried at room temperature for at least 1 hr prior to counting the spots that have formed on the membrane using an Immunospot Plate reader (CTL; Cellular Technology Limited).

Results

The gp100 TCR-anti-CD3 scFv fusions tested in this example are described below as proteins 1, 2, 3 and 4.

Protein 1 comprises the gp100 TCR alpha chain having the sequence SEQ ID NO: 45 but with the variable domain of SEQ ID NO: 8 where X=S, and the gp100 TCR beta chain-anti-CD3 scFv of SEQ ID NO: 36 but with amino acids at positions 1 and 2 being D and I respectively.

Protein 2 comprises the gp100 TCR alpha chain having the sequence SEQ ID NO: 45 but with the variable domain of SEQ ID NO: 8 where X=G, but with 8 amino acid residues truncated at its C-terminus (F196 to S203 inclusive), and the gp100 TCR beta chain-anti-CD3 scFv of SEQ ID NO: 36 but with amino acids at positions 1 and 2 being A and Q respectively Protein 3 comprises the gp100 TCR alpha chain having the sequence SEQ ID NO: 45 but with the variable domain of SEQ ID NO: 8 where X=A, but with 8 amino acid residues truncated at its C-terminus (F196 to S203 inclusive), and the gp100 TCR beta chain-anti-CD3 scFv of SEQ ID NO: 36 but with amino acids at positions 1 and 2 being A and I respectively.

Protein 4 comprises the gp100 TCR alpha chain having the sequence SEQ ID NO: 45 but with the variable domain of SEQ ID NO: 8 where X=G, but with 8 amino acid residues truncated at its C-terminus (F196 to S203 inclusive), and the gp100 TCR beta chain-anti-CD3 scFv of SEQ ID NO: 36 but with amino acids at positions 1 and 2 being D and I respectively.

The TCR-anti-CD3 fusions were prepared as described in Example 6.

IFNγ release by activated CD8 T cells redirected by the high affinity gp100 TCR-anti-CD3 fusion proteins was tested by ELISPOT assay (as described above). The number of ELISPOT spots observed in each well was plotted using Prism (Graph Pad) (see FIG. 11). From the dose-response curves, the EC50 values were determined (EC50 are determined at the concentration of TCR-anti-CD3 fusion that induces 50% of the maximum response).

Figure 11:
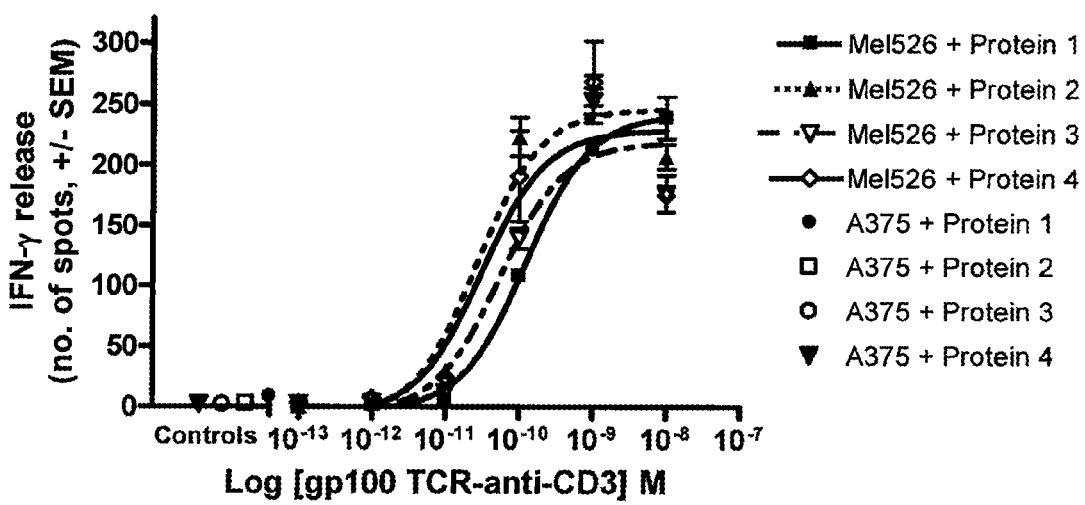
FIG. 11 shows the IFN-γ release of CD8+ T cells activated by different gp100 TCR-anti-CD3 scFv fusions.

The graph in FIG. 11 shows the specific activation of CD8+ T cells by the gp100 TCR-anti-CD3 fusions specifically binding to gp100 presenting cells. This assay allowed testing of four gp100 TCR-anti-CD3 fusion proteins which all showed efficient redirection of T cells and very similar potencies as shown in the table below.

| Protein No | $EC_{50}$ |
|---|---|
| 1 | 1.252e−10 |
| 2 | 2.69e−11 |
| 3 | 5.54e−11 |
| 4 | 3.149e−11 |

Example 12

In Vivo Efficacy of High Affinity gp100-Anti-CD3 Fusion

High affinity gp100-anti-CD3 fusions are specific for the human YLEPGPVTA (SEQ ID NO: 1) gp100 peptide-HLA-A2 complex and human CD3 and do not bind to mice gp100 peptide-HLA complex or CD3. Therefore anti-tumour efficacy was studied in immunodeficient mice with a human melanoma xenograft model.

Beige/SCID Mel526 Xenograft Model:

The Mel526 human melanoma cell line was selected for the establishment of a human xenograft model since Mel526 cells present the gp100 peptide-HLA-A2 complex and high affinity gp100-anti-CD3 fusions demonstrated redirected lysis of Mel526 cells in vitro. Immunodeficient Beige/SCID mice (deficient in T, B, NK cells function) were used in this model.

Cell Engraftment

The Mel526 tumour cells ($2\times10^6$/mouse) were mixed with human PBMC cells ($5\times10^6$/mouse) in PBS (200 μl/mouse) and were subcutaneously injected into each mice at Day 0. PBMCs originating from 4 healthy human donors were distributed evenly among the 6 groups of 8 mice.

Study Design:

Eight animals per group were intravenously treated with vehicle control (PBS+murine serum) or the high affinity gp100 TCR-anti-CD3 fusion for five consecutive days, starting one hour after subcutaneous injection of Mel526 tumour cells and PBMCs or Mel526 cells alone. Details of the study design are presented in the table below. The gp100 TCR-anti-CD3 fusion tested in this experiment comprises a gp100 TCR alpha chain containing the alpha variable domain SEQ ID NO: 8 (X=S) and the gp100 TCR beta chain-anti-CD3 scFv of SEQ ID NO: 36 wherein amino acids at positions 1 and 2 are D and I respectively. This TCR-anti-CD3 fusion was prepared as explained in Example 6.

| Group | N | Target cells (Mel 526) | Effector cells (PBMCs) | Treatment | Dose |
|---|---|---|---|---|---|
| 1 | 8 | $2 \times 10^6$ | — | Vehicle | — |
| 2 | 8 | $2 \times 10^6$ | $5 \times 10^6$ | Vehicle | — |
| 3 | 8 | $2 \times 10^6$ | $5 \times 10^6$ | gp100 TCR-anti-CD3 fusion | 0.1 mg/kg |
| 4 | 8 | $2 \times 10^6$ | $5 \times 10^6$ | gp100 TCR-anti-CD3 fusion | 0.04 mg/kg |
| 5 | 8 | $2 \times 10^6$ | $5 \times 10^6$ | gp100 TCR-anti-CD3 fusion | 0.01 mg/kg |
| 6 | 8 | $2 \times 10^6$ | $5 \times 10^6$ | gp100 TCR-anti-CD3 fusion | 0.004 mg/kg |

Study Read-Out

Tumour size and body weight were measured throughout study (three times a week) starting the day of Tumour/PBMCs engraftment. Dimensions of the tumour were determined by the measurement lengths and widths by using an external calliper. The length corresponds to the horizontal dimension largest of the tumour and the width corresponds to the shortest dimension of the tumour. The average tumour volume (Mean+SD; Mean+SEM) was estimated and given in graph. The tumour growth data were recorded for each individually identified mouse. Tumour volume was calculated by using the following formula: $V = Length \times Width^2/2$.

Results

Figure 12:
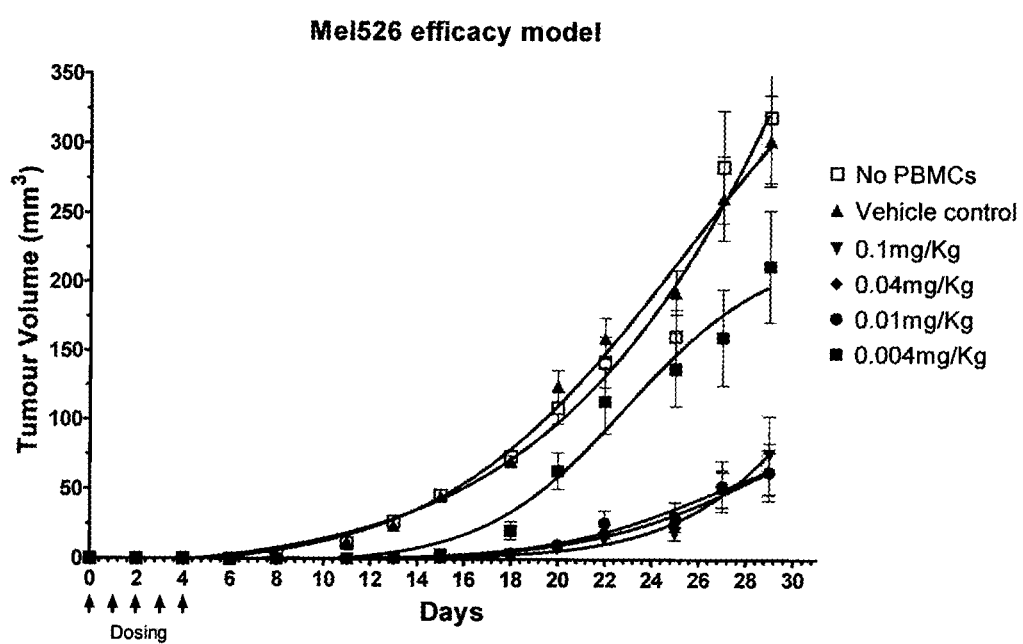
FIG. 12 shows the evolution of the average tumour volume in an in vivo model, using immunodeficient mice with a human melanoma xenograft, and testing the anti-tumour efficacy of a gp100 high affinity TCR-anti-CD3 scFv fusion protein.

FIG. 12 shows average tumour volume in each study group. Injection of target cells without effector cells followed by vehicle treatment (group 1) and injection of target cells with effector cells followed by vehicle treatment (group 2) showed measurable tumour growth starting at day 11. The growth rate of the tumours in group 2 was similar to the tumour growth rate in group 1.

High affinity gp100 TCR-anti-CD3 treatment showed a significant therapeutic efficacy in measurable tumour growth and induced a dose-dependent inhibition of Mel 526 tumour growth in the presence of PBMC effector cells.

The invention is further described by the following numbered paragraphs:

1. A T cell receptor (TCR) having the property of binding to YLEPGPVTA (SEQ ID NO: 1) HLA-A2 complex and comprising a TCR alpha variable domain and/or a TCR beta variable domain, characterized in that:

(i) said TCR is mutated relative to a TCR having the extracellular alpha and beta chain sequences SEQ ID NOs: 2 and 3 in its alpha chain variable domain amino acids 1 to 109 of SEQ ID NO: 2 and/or its beta chain variable domain amino acids 1 to 112 of SEQ ID NO: 3; and (ii) said alpha variable domain has at least 90% sequence identity to the amino acid sequence 1 to 109 of SEQ ID NO: 2, and/or said beta variable domain has at least 90% sequence identity to the amino acid sequence 1 to 112 of SEQ ID NO: 3; and (iii) said TCR has a binding affinity for, and/or a binding half-life for, the YLEPGPVTA (SEQ ID NO: 1)-HLA-A2 complex at least double that of a reference TCR, the said reference TCR having the extracellular alpha chain sequence SEQ ID NO: 45 and the extracellular beta chain sequence SEQ ID NO: 46.

2. A TCR as claimed in paragraph 1 in which the said mutation or mutations is/are in one or more of the complementarity determining regions of the alpha and/or beta variable domain.

3. A TCR as claimed in paragraph 1 or paragraph 2 in which the said mutation or mutations is/are in complementarity determining region 3 of the alpha chain variable domain, and/or one or more of the complementarity determining regions of the beta chain variable domain.

4. A TCR having the property of binding to YLEPGPVTA (SEQ ID NO: 1) HLA-A2 complex and having the alpha chain variable domain sequence of amino acids 1 to 109 of SEQ ID NO: 2, except that amino acid residues at one or more of positions 94D, 97L, 98V or 102G are mutated, and/or having the beta chain variable sequence of amino acids 1 to 112 of SEQ ID NO: 3 except that amino acid residues at one or more of positions 27L, 28N, 29H, 30D, 31A, 50Q, 51I, 52V, 53N, 54D, 61A, 94S, 95 I, 96G, 97G, 98P or 100E are mutated.

5. A TCR as claimed in paragraph 4 having a binding affinity for, and/or a binding half-life for, the YLEPGPVTA-HLA-A2 complex at least double that of the reference TCR.

6. A TCR as claimed in any one of the preceding paragraphs comprising one or more substitutions of alpha chain variable domain amino acid residues 94S, 94T, 94R, 97M, 98M, 98Q, 98G, 98S, 98A or 102D using the numbering shown in SEQ ID NO: 2.

7. A TCR as claimed in any one of the preceding paragraphs comprising one or more substitutions of beta chain variable domain amino acid residues 27I, 28F, 29Q, 30K, 31K, 50W, 51A, 51G, 52Q, 52Y, 52T, 53G, 53F, 54N, 54H, 61T, 94L, 95Y, 95H, 95W, 95F, 95S, 95V, 96C, 97E, 97A, 98G, 100Q or 100P using the numbering shown in SEQ ID NO: 3.

5. A TCR as claimed in paragraph 4 having a binding affinity for, and/or a binding half-life for, the YLEPGPVTA (SEQ ID NO: 1)-HLA-A2 complex at least double that of the reference TCR.

9. A TCR as claimed in any one of the preceding paragraphs comprising one of the beta chain variable domain amino acid sequences SEQ ID NOs: 10, 11, 12, 13, 14, 15, 16, 17, 18, 19, 20, 21, 22, 23, 24, 25, 26, 27, 28, 29, 30, 31, 32, 33, 34 and 35.

10. A TCR as claimed in any one of the preceding paragraphs which is an αβ heterodimeric TCR, and which have alpha and beta chain constant domain sequences in which cysteine residues are substituted for Thr 48 of TRAC and Ser 57 of TRBC1 or TRBC2, the said cysteines forming a disulfide bond between the alpha and beta constant domains of the TCR.

11. A TCR as claimed in any one of the preceding paragraphs which is an αβ heterodimeric TCR, and which have alpha and beta chain constant domain sequences in which, constant domain sequences are linked by the native disulfide bond between Cys4 of exon 2 of TRAC and Cys2 of exon 2 of TRBC1 or TRBC2.

12. A TCR as claimed in any one of the preceding paragraphs which is associated with a detectable label, a therapeutic agent, a PK modifying moiety or a combination of any of these.

13. A TCR as claimed in paragraph 12 wherein the therapeutic agent is an anti-CD3 antibody covalently linked to the C- or N-terminus of the alpha or beta chain of the TCR.

14. A TCR as claimed in any one of the preceding paragraphs with modified glycosylation compared to the TCR having the extracellular alpha and beta chain sequences SEQ ID NOs: 2 and 3.

15. A multivalent TCR complex comprising at least two TCRs as claimed in any one of the preceding paragraphs.

16. DNA or RNA encoding a TCR as claimed in any one of paragraphs 1 to 14.

17. An isolated cell presenting a TCR as claimed in any one of paragraphs 1 to 11.

18. A TCR as claimed in paragraph 13 comprising:
a TCR alpha chain amino acid sequence selected from the group consisting of:
(i) the TCR alpha chain sequence SEQ ID NO: 45, wherein amino acids 1 to 109 are replaced by the sequence SEQ ID NO: 8, wherein amino acid at position 1 is S;
(ii) the TCR alpha chain sequence SEQ ID NO: 45, wherein amino acids 1 to 109 are replaced by the sequence SEQ ID NO: 8, wherein amino acid at position 1 is A;
(iii) the TCR alpha chain sequence SEQ ID NO: 45, wherein amino acids 1 to 109 are replaced by the sequence SEQ ID NO: 8, wherein amino acid at position 1 is G;
(iv) the TCR alpha chain sequence SEQ ID NO: 45, wherein amino acids 1 to 109 are replaced by the sequence SEQ ID NO: 8, wherein amino acid at position 1 is S, and the C-terminus of the alpha chain is truncated by 8 amino acids from F196 to S203 inclusive, based on the numbering of SEQ ID NO: 45;
(v) the TCR alpha chain sequence SEQ ID NO: 45, wherein amino acids 1 to 109 are replaced by the sequence SEQ ID NO: 8, wherein amino acid at position 1 is A, and the C-terminus of the alpha chain is truncated by 8 amino acids from F196 to S203 inclusive, based on the numbering of SEQ ID NO: 45; and
(vi) the TCR alpha chain sequence SEQ ID NO: 45, wherein amino acids 1 to 109 are replaced by the sequence SEQ ID NO: 8, wherein amino acid at position 1 is G, and the C-terminus of the alpha chain is truncated by 8 amino acids from F196 to S203 inclusive, based on the numbering of SEQ ID NO: 45;
and a TCR beta chain-anti-CD3 amino acid sequence selected from the group consisting of:

(vii) the TCR beta chain-anti-CD3 sequence SEQ ID NO: 36, wherein amino acids at positions 1 and 2 are D and I respectively;
(viii) the TCR beta chain-anti-CD3 sequence SEQ ID NO: 36, wherein amino acids at positions 1 and 2 are A and I respectively;
(ix) the TCR beta chain-anti-CD3 sequence SEQ ID NO: 36, wherein amino acids at positions 1 and 2 are A and Q respectively;
(x) the TCR beta chain-anti-CD3 sequence SEQ ID NO: 36, wherein amino acids at positions 1 and 2 are D and I respectively amino acids at positions 108-131 are replaced by SEQ ID NO: 44, and amino acids at positions 254-258 are replaced by SEQ ID NO: 47;
(xi) the TCR beta chain-anti-CD3 sequence SEQ ID NO: 36, wherein amino acids at positions 1 and 2 are D and I respectively and amino acid at position 257 is a S and amino acid at position 258 is a G;
(xii) the TCR beta chain-anti-CD3 sequence SEQ ID NO: 36, wherein amino acids at positions 1 and 2 are D and I respectively and amino acid at position 256 is a S and amino acid at position 258 is a G;
(xiii) the TCR beta chain-anti-CD3 sequence SEQ ID NO: 36, wherein amino acids at positions 1 and 2 are D and I respectively and amino acid at position 255 is a S and amino acid at position 258 is a G;
(xiv) a TCR beta chain-anti-CD3 having the sequence SEQ ID NO: 36, wherein amino acids at positions 1 and 2 are A and Q, and wherein amino acid at position 257 is a S and amino acid at position 258 is a G.
(xv) a TCR beta chain-anti-CD3 having the sequence SEQ ID NO: 36, wherein amino acids at positions 1 and 2 are A and Q, and wherein amino acid at position 256 is a S and amino acid at position 258 is a G;
(xvi) a TCR beta chain-anti-CD3 having the sequence SEQ ID NO: 36, wherein amino acids at positions 1 and 2 are A and Q, and wherein amino acid at position 255 is a S and amino acid at position 258 is a G;
(xvii) and a TCR beta chain-anti-CD3 having the sequence SEQ ID NO: 36, wherein amino acid at positions 1 and 2 are A and I respectively, and wherein amino acid at position 257 is a S and amino acid at position 258 is a G;
(xviii) a TCR beta chain-anti-CD3 having the sequence SEQ ID NO: 36, wherein amino acid at positions 1 and 2 are A and I respectively, and wherein amino acid at position 256 is a S and amino acid at position 258 is a G; and
(xix) a TCR beta chain-anti-CD3 having the sequence SEQ ID NO: 36, wherein amino acids at positions 1 and 2 are A and I respectively, and wherein amino acid at position 255 is a S and amino acid at position 258 is a G.

19. A TCR as claimed in paragraph 18 in which the alpha chain amino acid sequence is (i) and the beta chain-anti-CD3 amino acid sequence is (vii).

20. A TCR as claimed in paragraph 18 in which the alpha chain amino acid sequence is (i) and the beta chain-anti-CD3 amino acid sequence is (x).

21. A TCR as claimed in paragraph 18 in which the alpha chain amino acid sequence is (vi) and the beta chain-anti-CD3 amino acid sequence is (ix).

22. A TCR as claimed in paragraph 18 in which the alpha chain amino acid sequence is (v) and the beta chain-anti-CD3 amino acid sequence is (viii). 23. A TCR as claimed in paragraph 18 in which the alpha chain amino acid sequence is (vi) and the beta chain-anti-CD3 amino acid sequence is (vii).

24. A TCR as claimed in paragraph 18 in which the alpha chain amino acid sequence is (i) and the beta chain-anti-CD3 amino acid sequence is (xi).

25. A TCR as claimed in paragraph 18 in which the alpha chain amino acid sequence is (i) and the beta chain-anti-CD3 amino acid sequence is (xii).

26. A TCR as claimed in paragraph 18 in which the alpha chain amino acid sequence is (i) and the beta chain-anti-CD3 amino acid sequence is (xiii).

27. A TCR as claimed in paragraph 18 in which the alpha chain amino acid sequence is (vi) and the beta chain-anti-CD3 amino acid sequence is (xiv).

28. A TCR as claimed in paragraph 18 in which the alpha chain amino acid sequence is (vi) and the beta chain-anti-CD3 amino acid sequence is (xv).

29. A TCR as claimed in paragraph 18 in which the alpha chain amino acid sequence is (vi) and the beta chain-anti-CD3 amino acid sequence is (xvi).

30. A TCR as claimed in paragraph 18 in which the alpha chain amino acid sequence is (v) and the beta chain-anti-CD3 amino acid sequence is (xvii).

31. A TCR as claimed in paragraph 18 in which the alpha chain amino acid sequence is (v) and the beta chain-anti-CD3 amino acid sequence is (xviii).

32. A TCR as claimed in paragraph 18 in which the alpha chain amino acid sequence is (v) and the beta chain-anti-CD3 amino acid sequence is (xix).

33. A TCR as claimed in paragraph 18 in which the alpha chain amino acid sequence is (vi) and the beta chain-anti-CD3 amino acid sequence is (xi).

34. A TCR as claimed in paragraph 18 in which the alpha chain amino acid sequence is (vi) and the beta chain-anti-CD3 amino acid sequence is (xii).

35. A TCR as claimed in paragraph 18 in which the alpha chain amino acid sequence is (vi) and the beta chain-anti-CD3 amino acid sequence is (xiii).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A non-naturally occurring T cell receptor (TCR) that binds to a YLEPGPVTA (SEQ ID NO: 1)-HLA-A2 complex comprising a TCR alpha chain variable domain and a TCR beta chain variable domain, wherein:
   (a) the alpha chain variable domain has
       (i) at least 90% sequence identity to the amino acid sequence comprising amino acids 1 to 109 of SEQ ID NO: 2, or
       (ii) at least 90% sequence identity to the amino acids 1 to 109 of SEQ ID NO: 2 and has a mutation at one or more positions selected from the group consisting of: 94D, 97L, 98V and 102G;
   (b) the beta chain variable domain has
       (i) amino acids 1 to 112 of SEQ ID NO: 3, and a mutation at one or more positions selected from the group consisting of: 27L, 28N, 29H, 30D, 31A, 50Q, 51I, 52V, 53N, 54D, 61A, 94S, 95I, 96G, 97G, 98P and 100E, or
       (ii) at least 90% sequence identity to the amino acid sequence comprising amino acids 1 to 112 of SEQ ID NO: 3;
   (c) the TCR has a binding affinity for, and/or a binding half-life for, the YLEPGPVTA-(SEQ ID NO: 1) HLA-A2 complex which is at least double that of a reference TCR, the reference TCR having an extracellular alpha chain sequence of SEQ ID NO: 45 and an extracellular beta chain sequence of SEQ ID NO: 46; and
   (d) at least one of the alpha and beta chain variable domains has at least one mutation.

2. A TCR according to claim 1, wherein the alpha chain variable domain comprises one or more amino acid substitutions selected from the group consisting of 94S, 94T, 94R, 97M, 98M, 98Q, 98G, 98S, 98A and 102D, with reference to the position numbering of SEQ ID NO: 2.

3. A TCR according to claim 1, wherein the beta chain variable domain comprises one or more amino acid substitutions selected from the group consisting of: 27I, 28F, 29Q, 30K, 31K, 50W, 51A, 51G, 52Q, 52Y, 52T, 53G, 53F, 54N, 54H, 61T, 94L, 95Y, 95H, 95W, 95F, 95S, 95V, 96C, 97E, 97A, 98G, 100Q and 100P, with reference to the position numbering of SEQ ID NO: 3.

4. A TCR according to claim 1, wherein the alpha chain variable domain comprises an amino acid sequence selected from the group consisting of SEQ ID NOs: 7, 8 and 9.

5. A TCR according to claim 1, wherein the beta chain variable domain comprises an amino acid sequence selected from the group consisting of SEQ ID NOs: 10, 11, 12, 13, 14, 15, 16, 17, 18, 19, 20, 21, 22, 23, 24, 25, 26, 27, 28, 29, 30, 31, 32, 33, 34 and 35.

6. A TCR according to claim 1, wherein the TCR is an αβ heterodimeric TCR comprising alpha and beta chain constant domain sequences in which cysteine residues are substituted for Thr 48 of TRAC and Ser 57 of TRBC1 or TRBC2 and form a disulfide bond between the alpha and beta constant domains of the TCR.

7. A TCR according to claim 1, wherein the TCR is an αβ heterodimeric TCR comprising alpha and beta chain constant domain sequences in which the constant domain sequences are linked by a native disulfide bond between Cys4 of exon 2 either of TRAC and Cys2 of exon 2 of either TRBC1 or TRBC2.

8. A TCR according to claim 1, wherein the TCR is associated with a detectable label, a therapeutic agent, a PK modifying moiety or any combination thereof.

9. A TCR according to claim 8, wherein the therapeutic agent is an anti-CD3 antibody covalently linked to the C- or N-terminus of the alpha or beta chain of the TCR.

10. A TCR according to claim 1, wherein the TCR has modified glycosylation compared to the TCR having an extracellular alpha chain sequence of SEQ ID NO: 2 and an extracellular beta chain sequence of SEQ ID NO: 3.

11. A multivalent TCR complex comprising at least two or more TCRs according to claim 1.

12. A TCR according to claim 9, wherein the TCR comprises:
   (a) a TCR alpha chain variable domain comprising an amino acid sequence selected from the group consisting of:
       (i) the TCR alpha chain sequence SEQ ID NO: 45, wherein amino acids 1 to 109 are replaced by the sequence SEQ ID NO: 8, wherein amino acid at position 1 is S;
       (ii) the TCR alpha chain sequence SEQ ID NO: 45, wherein amino acids 1 to 109 are replaced by the sequence SEQ ID NO: 8, wherein amino acid at position 1 is A;
       (iii) the TCR alpha chain sequence SEQ ID NO: 45, wherein amino acids 1 to 109 are replaced by the sequence SEQ ID NO: 8, wherein amino acid at position 1 is G;
       (iv) the TCR alpha chain sequence SEQ ID NO: 45, wherein amino acids 1 to 109 are replaced by the sequence SEQ ID NO: 8, wherein amino acid at position 1 is S, and the C-terminus of the alpha chain is truncated by 8 amino acids from F196 to S203 inclusive, based on the numbering of SEQ ID NO: 45;
       (v) the TCR alpha chain sequence SEQ ID NO: 45, wherein amino acids 1 to 109 are replaced by the sequence SEQ ID NO: 8, wherein amino acid at position 1 is A, and the C-terminus of the alpha chain is truncated by 8 amino acids from F196 to 5203 inclusive, based on the numbering of SEQ ID NO: 45; and
       (vi) the TCR alpha chain sequence SEQ ID NO: 45, wherein amino acids 1 to 109 are replaced by the sequence SEQ ID NO: 8, wherein amino acid at position 1 is G, and the C-terminus of the alpha chain is truncated by 8 amino acids from F 196 to 5203 inclusive, based on the numbering of SEQ ID NO: 45; and (b) a TCR beta chain variable domain comprising a TCR beta chain-anti-CD3 amino acid sequence selected from the group consisting of:
- (vii) the TCR beta chain-anti-CD3 sequence SEQ ID NO: 36, wherein amino acids at positions 1 and 2 are D and I, respectively;
- (viii) the TCR beta chain-anti-CD3 sequence SEQ ID NO: 36, wherein amino acids at positions 1 and 2 are A and I, respectively;
- (ix) the TCR beta chain-anti-CD3 sequence SEQ ID NO: 36, wherein amino acids at positions 1 and 2 are A and Q, respectively;
- (x) the TCR beta chain-anti-CD3 sequence SEQ ID NO: 36, wherein amino acids at positions 1 and 2 are D and I, respectively, and amino acids at positions 108-131 are replaced by SEQ ID NO: 44, and amino acids at positions 254-258 are replaced by SEQ ID NO: 47;
- (xi) the TCR beta chain-anti-CD3 sequence SEQ ID NO: 36, wherein amino acids at positions 1 and 2 are D and I, respectively, and the amino acid at position 257 is an S and the amino acid at position 258 is a G;
- (xii) the TCR beta chain-anti-CD3 sequence SEQ ID NO: 36, wherein amino acids at positions 1 and 2 are D and I, respectively, and the amino acid at position 256 is an S and the amino acid at position 258 is a G;
- (xiii) the TCR beta chain-anti-CD3 sequence SEQ ID NO: 36, wherein amino acids at positions 1 and 2 are D and L respectively and the amino acid at position 255 is an S and the amino acid at position 258 is a G;
- (xiv) a TCR beta chain-anti-CD3 having the sequence SEQ ID NO: 36, wherein amino acids at positions 1 and 2 are A and Q, and wherein the amino acid at position 257 is an S and the amino acid at position 258 is a G;
- (xv) a TCR beta chain-anti-CD3 having the sequence SEQ ID NO: 36, wherein amino acids at positions 1 and 2 are A and Q, and wherein the amino acid at position 256 is an S and the amino acid at position 258 is a G;
- (xvi) a TCR beta chain-anti-CD3 having the sequence SEQ ID NO: 36, wherein amino acids at positions 1 and 2 are A and Q, and wherein the amino acid at position 255 is an S and the amino acid at position 258 is a G;
- (xvii) and a TCR beta chain-anti-CD3 having the sequence SEQ ID NO: 36, wherein amino acid at positions 1 and 2 are A and I, respectively, and wherein the amino acid at position 257 is an S and the amino acid at position 258 is a G;
- (xviii) a TCR beta chain-anti-CD3 having the sequence SEQ ID NO: 36, wherein amino acid at positions 1 and 2 are A and I, respectively, and wherein the amino acid at position 256 is an S and the amino acid at position 258 is a G; and
- (xix) a TCR beta chain-anti-CD3 having the sequence SEQ ID NO: 36, wherein amino acids at positions 1 and 2 are A and I, respectively, and wherein the amino acid at position 255 is an S and the amino acid at position 258 is a G.

13. A TCR according to claim 12, wherein alpha chain amino acid sequence is (i) and the beta chain-anti-CD3 amino acid sequence is (vii).

14. A TCR according to claim 12, wherein the alpha chain amino acid sequence is (i) and the beta chain-anti-CD3 amino acid sequence is (x).

15. A TCR according to claim 12, wherein the alpha chain amino acid sequence is (vi) and the beta chain-anti-CD3 amino acid sequence is (ix).

16. A TCR according to claim 12, wherein the alpha chain amino acid sequence is (v) and the beta chain-anti-CD3 amino acid sequence is (viii).

17. A TCR according to claim 12, wherein the alpha chain amino acid sequence is (vi) and the beta chain-anti-CD3 amino acid sequence is (vii).

18. A TCR according to claim 12, wherein the alpha chain amino acid sequence is (i) and the beta chain-anti-CD3 amino acid sequence is (xi).

19. A TCR according to claim 12, wherein the alpha chain amino acid sequence is (i) and the beta chain-anti-CD3 amino acid sequence is (xii).

20. A TCR according to claim 12, wherein the alpha chain amino acid sequence is (i) and the beta chain-anti-CD3 amino acid sequence is (xiii).

21. A TCR according to claim 12, wherein the alpha chain amino acid sequence is (vi) and the beta chain-anti-CD3 amino acid sequence is (xiv).

22. A TCR according to claim 12, wherein the alpha chain amino acid sequence is (vi) and the beta chain-anti-CD3 amino acid sequence is (xv).

23. A TCR according to claim 12, wherein the alpha chain amino acid sequence is (vi) and the beta chain-anti-CD3 amino acid sequence is (xvi).

24. A TCR according to claim 12, wherein the alpha chain amino acid sequence is (v) and the beta chain-anti-CD3 amino acid sequence is (xvii).

25. A TCR according to claim 12, wherein the alpha chain amino acid sequence is (v) and the beta chain-anti-CD3 amino acid sequence is (xviii).

26. A TCR according to claim 12, wherein the alpha chain amino acid sequence is (v) and the beta chain-anti-CD3 amino acid sequence is (xix).

27. A TCR according to claim 12, wherein the alpha chain amino acid sequence is (vi) and the beta chain-anti-CD3 amino acid sequence is (xi).

28. A TCR according to claim 12, wherein the alpha chain amino acid sequence is (vi) and the beta chain-anti-CD3 amino acid sequence is (xii).

29. A TCR according to claim 12, wherein the alpha chain amino acid sequence is (vi) and the beta chain-anti-CD3 amino acid sequence is (xiii).

30. A TCR according to claim 1, wherein:
- (a) the alpha chain variable domain has at least 90% sequence identity to the amino acid sequence comprising amino acids 1 to 109 of SEQ ID NO: 2 and has a mutation at one or more positions selected from the group consisting of: 94D, 97L, 98V and 102G;
- (b) the beta chain variable domain has at least 90% sequence identity to the amino acid sequence comprising amino acids 1 to 112 of SEQ ID NO: 3 and has a mutation at one or more positions selected from the group consisting of: 27L, 28N, 29H, 30D, 31A, 50Q, 51I, 52V, 53N, 54D, 61A, 94S, 95I, 96G, 97G, 98P and 100E; and
- (c) the TCR has a binding affinity for, and/or a binding half-life for, the YLEPGPVTA-(SEQ ID NO: 1) HLA-A2 complex which is at least double that of a reference TCR, the reference TCR having an extracellular alpha chain sequence of SEQ ID NO: 45 and an extracellular beta chain sequence of SEQ ID NO: 46.

31. A TCR according to claim 1, wherein the alpha chain variable domain has at least 93% sequence identity to the amino acid sequence comprising amino acids 1 to 109 of SEQ ID NO: 2 and has a mutation at one or more positions selected from the group consisting of: 94D, 97L, 98V and 102G.

32. A TCR according to claim 1, wherein the alpha chain variable domain has at least 94% sequence identity to the amino acid sequence comprising amino acids 1 to 109 of SEQ ID NO: 2 and has a mutation at one or more positions selected from the group consisting of: 94D, 97L, 98V and 102G.

33. A TCR according to claim 1, wherein the alpha chain variable domain has the amino acid sequence comprising amino acids 1 to 109 of SEQ ID NO: 2.

34. A TCR according to claim 1, wherein the alpha chain variable domain has at least one or more of the mutations.

\* \* \* \* \*

UNITED STATES PATENT AND TRADEMARK OFFICE
CERTIFICATE OF CORRECTION

PATENT NO. : 8,519,100 B2  
APPLICATION NO. : 13/342579  
DATED : August 27, 2013  
INVENTOR(S) : Bent Karsten Jakobsen, Naomi Harwood and Nathaniel Ross Liddy Page 1 of 1

It is certified that error appears in the above-identified patent and that said Letters Patent is hereby corrected as shown below:

On the Title Page

Item (75), the "Inventors" section should read:
Bent Karsten Jakobsen, Oxfordshire (GB); Naomi Harwood, Oxfordshire (GB); Nathaniel Ross Liddy, Abingdon (GB)

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 51

<210> SEQ ID NO 1
<211> LENGTH: 9
<212> TYPE: PRT
<213> ORGANISM: Homo sapiens

<400> SEQUENCE: 1

Tyr Leu Glu Pro Gly Pro Val Thr Ala
1               5

<210> SEQ ID NO 2
<211> LENGTH: 203
<212> TYPE: PRT
<213> ORGANISM: Homo sapiens

<400> SEQUENCE: 2

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Gly Asp Thr Pro
                85                  90                  95

Leu Val Phe Gly Lys Gly Thr Arg Leu Ser Val Ile Ala Asn Ile Gln
            100                 105                 110

Lys Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
    130                 135                 140

Gln Ser Lys Asp Ser Asp Val Tyr Ile Thr Asp Lys Thr Val Leu Asp
145                 150                 155                 160

Met Arg Ser Met Asp Phe Lys Ser Asn Ser Ala Val Ala Trp Ser Asn
```

```
                        165                 170                 175
Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser
        195                 200

<210> SEQ ID NO 3
<211> LENGTH: 242
<212> TYPE: PRT
<213> ORGANISM: Homo sapiens

<400> SEQUENCE: 3

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 4
<211> LENGTH: 622
<212> TYPE: DNA
<213> ORGANISM: Artificial Sequence
<220> FEATURE:
<223> OTHER INFORMATION: T cell receptor alpha chain

<400> SEQUENCE: 4
catatgagtc aacaaggaga agaagatcct caggccttga gcatccagga gggtgaaaat      60
gccaccatga actgcagtta caaaactagt ataaacaatt tacagtggta tagacaaaat     120
tcaggtagag gccttgtcca cctaatttta atacgttcaa atgaaagaga gaaacacagt     180
ggaagattaa gagtcacgct tgacacttcc aagaaaagca gttccttgtt gatcacggct     240
```

```
tcccgggcag cagacactgc ttcttacttc tgtgctacgg acggagacac acctcttgtc    300
tttggaaagg gcacaagact ttctgtgatt gcaaatatcc agaagcctga ccctgccgtg    360
taccagctga gagactctaa gtcgagtgac aagtctgtct gcctattcac cgattttgat    420
tctcaaacaa atgtgtcaca agtaaggat tctgatgtgt atatcacaga caaatgtgtg    480
ctagacatga ggtctatgga cttcaagagc aacagtgctg tggcctggag caacaaatct    540
gactttgcat gtgcaaacgc cttcaacaac agcattattc cagaagacac cttcttcccc    600
agcccagaaa gttcctaagc tt                                             622
```

```
<210> SEQ ID NO 5
<211> LENGTH: 739
<212> TYPE: DNA
<213> ORGANISM: Artificial Sequence
<220> FEATURE:
<223> OTHER INFORMATION: T cell receptor beta chain

<400> SEQUENCE: 5
```

```
catatggatg gtggaattac tcaatcccca aagtacctgt tcagaaagga aggacagaat    60
gtgaccctga gttgtgaaca gaatttgaac cacgatgcca tgtactggta ccgacaggac    120
ccagggcaag ggctgagatt gatctactac tcacagatag taaatgactt tcagaaagga    180
gatatagctg aagggtacag cgtctctcgg gagaagaagg aatcctttcc tctcactgtg    240
acatcggccc aaaagaaccc gacagctttc tatctctgtg ccagtagtat agggggcccc    300
tacgagcagt acttcgggcc gggcaccagg ctcacggtca cagaggacct gaaaaacgtg    360
ttcccacccg aggtcgctgt gtttgagcca tcagaagcag agatctccca cacccaaaag    420
gccacactgg tgtgcctggc caccggtttc taccccgacc acgtggagct gagctggtgg    480
gtgaatggga aggaggtgca cagtggggtc tgcacagacc cgcagcccct caaggagcag    540
cccgccctca atgactccag atacgctctg agcagccgcc tgagggtctc ggccaccttc    600
tggcaggacc cccgcaacca cttccgctgt caagtccagt tctacgggct ctcggagaat    660
gacgagtgga cccaggatag ggccaaaccc gtcacccaga tcgtcagcgc cgaggcctgg    720
ggtagagcag actaagctt                                                 739
```

```
<210> SEQ ID NO 6
<211> LENGTH: 9
<212> TYPE: PRT
<213> ORGANISM: Artificial Sequence
<220> FEATURE:
<223> OTHER INFORMATION: Variant gp100 peptide

<400> SEQUENCE: 6

Tyr Leu Glu Pro Gly Pro Val Thr Val
1               5
```

```
<210> SEQ ID NO 7
<211> LENGTH: 109
<212> TYPE: PRT
<213> ORGANISM: Artificial Sequence
<220> FEATURE:
<223> OTHER INFORMATION: T cell receptor alpha chain variable domain

<400> SEQUENCE: 7

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30
```

```
Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
 50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Gly Ser Thr Pro
                 85                  90                  95

Leu Met Phe Gly Lys Gly Thr Arg Leu Ser Val Ile Ala
            100                 105

<210> SEQ ID NO 8
<211> LENGTH: 109
<212> TYPE: PRT
<213> ORGANISM: Artificial Sequence
<220> FEATURE:
<223> OTHER INFORMATION: T cell receptor alpha chain variable domain
<220> FEATURE:
<221> NAME/KEY: MISC_FEATURE
<222> LOCATION: (1)..(1)
<223> OTHER INFORMATION: Xaa can either be Ser or Ala or Gly

<400> SEQUENCE: 8

Xaa Gln Gln Gly Glu Glu Asp Pro Gln Ala Leu Ser Ile Gln Glu Gly
 1               5                  10                  15

Glu Asn Ala Thr Met Asn Cys Ser Tyr Lys Thr Ser Ile Asn Asn Leu
                 20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
 50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Gly Ser Thr Pro
                 85                  90                  95

Met Gln Phe Gly Lys Gly Thr Arg Leu Ser Val Ile Ala
            100                 105

<210> SEQ ID NO 9
<211> LENGTH: 109
<212> TYPE: PRT
<213> ORGANISM: Artificial Sequence
<220> FEATURE:
<223> OTHER INFORMATION: T cell receptor alpha chain variable domain

<400> SEQUENCE: 9

Ser Gln Gln Gly Glu Glu Asp Pro Gln Ala Leu Ser Ile Gln Glu Gly
 1               5                  10                  15

Glu Asn Ala Thr Met Asn Cys Ser Tyr Lys Thr Ser Ile Asn Asn Leu
                 20                  25                  30

Gln Trp Tyr Arg Gln Asn Ser Gly Arg Gly Leu Val His Leu Ile Leu
            35                  40                  45

Ile Arg Ser Asn Glu Arg Glu Lys His Ser Gly Arg Leu Arg Val Thr
 50                  55                  60

Leu Asp Thr Ser Lys Lys Ser Ser Ser Leu Leu Ile Thr Ala Ser Arg
 65                  70                  75                  80

Ala Ala Asp Thr Ala Ser Tyr Phe Cys Ala Thr Asp Gly Thr Thr Pro
                 85                  90                  95

Leu Gly Phe Gly Lys Asp Thr Arg Leu Ser Val Ile Ala
            100                 105
```

-continued

```
<210> SEQ ID NO 10
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 10

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Ala Gln Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 11

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Ala Gln Gly Asp Phe Gln Lys Gly Asp Ile Thr Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 12

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45
```

```
                35                  40                  45
Ser Trp Ala Gln Gly Asn Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ile Gly
                 85                  90                  95

Gly Pro Tyr Glu Gln Tyr Phe Gly Pro Gly Thr Arg Leu Thr Val Thr
                100                 105                 110

<210> SEQ ID NO 13
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 13

Asp Gly Gly Ile Thr Gln Ser Pro Lys Tyr Leu Phe Arg Lys Glu Gly
  1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
             35                  40                  45

Ser Trp Gly Val Gly Asp Phe Gln Lys Gly Asp Ile Thr Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ile Gly
                 85                  90                  95

Gly Pro Tyr Glu Gln Tyr Phe Gly Pro Gly Thr Arg Leu Thr Val Thr
                100                 105                 110

<210> SEQ ID NO 14
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 14

Asp Gly Gly Ile Thr Gln Ser Pro Lys Tyr Leu Phe Arg Lys Glu Gly
  1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
             35                  40                  45

Ser Trp Ala Gln Gly His Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ile Gly
                 85                  90                  95

Gly Pro Tyr Glu Gln Tyr Phe Gly Pro Gly Thr Arg Leu Thr Val Thr
                100                 105                 110

<210> SEQ ID NO 15
<211> LENGTH: 112
<212> TYPE: PRT
```

```
<213> ORGANISM: Artificial Sequence
<220> FEATURE:
<223> OTHER INFORMATION: T cell receptor beta chain variable domain

<400> SEQUENCE: 15

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Ala Gln Gly Asn Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

<210> SEQ ID NO 16
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 16

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Ala Tyr Gly His Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 17

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Ala Val Gly Asn Phe Gln Lys Gly Asp Ile Ala Glu Gly Tyr
    50                  55                  60
```

-continued

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ile Gly
                 85                  90                  95

Gly Pro Tyr Glu Gln Tyr Phe Gly Pro Gly Thr Arg Leu Thr Val Thr
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 18

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
             35                  40                  45

Ser Gln Ile Val Asn Asp Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Leu Tyr Cys
                 85                  90                  95

Glu Gly Tyr Glu Gln Tyr Phe Gly Pro Gly Thr Arg Leu Thr Val Thr
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 19

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
             35                  40                  45

Ser Trp Ala Gln Phe Asp Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ile Gly
                 85                  90                  95

Gly Pro Tyr Glu Gln Tyr Phe Gly Pro Gly Thr Arg Leu Thr Val Thr
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 20

```
Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Gly Thr Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110
```

<210> SEQ ID NO 21
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 21

```
Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Ile Phe Gln Lys Lys Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 22

```
Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Gly Thr Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95
```

```
Ala Pro Tyr Pro Gln Tyr Phe Gly Pro Gly Thr Arg Leu Thr Val Thr
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 23

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Gly Thr Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser His Gly
                85                  90                  95

Ala Pro Tyr Glu Gln Tyr Phe Gly Pro Gly Thr Arg Leu Thr Val Thr
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 24

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Gly Thr Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Trp Gly
                85                  90                  95

Ala Pro Tyr Glu Gln Tyr Phe Gly Pro Gly Thr Arg Leu Thr Val Thr
            100                 105                 110

<210> SEQ ID NO 25
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 25

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
```

```
            20                  25                  30
Tyr Trp Tyr Arg Gln Asp Pro Gly Gln Gly Leu Arg Leu Ile Tyr Tyr
         35                  40                  45

Ser Trp Ala Gln Gly Asp Phe Gln Lys Gly Asp Ile Ala Glu Gly Tyr
     50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Ile Gly
                 85                  90                  95

Ala Pro Tyr Pro Gln Tyr Phe Gly Pro Gly Thr Arg Leu Thr Val Thr
                100                 105                 110

<210> SEQ ID NO 26
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 26

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
         35                  40                  45

Ser Trp Ala Gln Gly Asp Phe Gln Lys Gly Asp Ile Ala Glu Gly Tyr
     50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser His Gly
                 85                  90                  95

Ala Pro Tyr Glu Gln Tyr Phe Gly Pro Gly Thr Arg Leu Thr Val Thr
                100                 105                 110

<210> SEQ ID NO 27
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 27

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
                 20                  25                  30

Tyr Trp Tyr Arg Gln Asp Pro Gly Gln Gly Leu Arg Leu Ile Tyr Tyr
         35                  40                  45

Ser Trp Ala Gln Gly Asp Phe Gln Lys Gly Asp Ile Ala Glu Gly Tyr
     50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Trp Gly
                 85                  90                  95

Ala Pro Tyr Glu Gln Tyr Phe Gly Pro Gly Thr Arg Leu Thr Val Thr
                100                 105                 110
```

```
<210> SEQ ID NO 28
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 28

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Trp Gly
                85                  90                  95

Ala Pro Tyr Glu Gln Tyr Phe Gly Pro Gly Thr Arg Leu Thr Val Thr
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 29

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Tyr Gly
                85                  90                  95

Ala Pro Tyr Glu Gln Tyr Phe Gly Pro Gly Thr Arg Leu Thr Val Thr
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 30

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45
```

Ser Gln Ile Val Asn Asp Phe Gln Lys Gly Asp Ile Ala Glu Gly Tyr
            50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys Ala Ser Ser Phe Gly
                85                  90                  95

Ala Pro Tyr Glu Gln Tyr Phe Gly Pro Gly Thr Arg Leu Thr Val Thr
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 31

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser His Gly
                85                  90                  95

Ala Pro Tyr Glu Gln Tyr Phe Gly Pro Gly Thr Arg Leu Thr Val Thr
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 32

Asp Gly Gly Ile Thr Gln Ser Pro Lys Tyr Leu Phe Arg Lys Glu Gly
 1               5                  10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ser Gly
                85                  90                  95

Ala Pro Tyr Glu Gln Tyr Phe Gly Pro Gly Thr Arg Leu Thr Val Thr
            100                 105                 110

<210> SEQ ID NO 33
<211> LENGTH: 112
<212> TYPE: PRT
<213> ORGANISM: Artificial Sequence
<220> FEATURE:

<223> OTHER INFORMATION: T cell receptor beta chain variable domain

<400> SEQUENCE: 33

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Ile Thr Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 34

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Gly Val Gly Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: T cell receptor beta chain variable domain

<400> SEQUENCE: 35

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Trp Gly Thr Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

```
Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
                100                 105                 110

<210> SEQ ID NO 36
<211> LENGTH: 500
<212> TYPE: PRT
<213> ORGANISM: Artificial Sequence
<220> FEATURE:
<223> OTHER INFORMATION: T cell receptor beta chain - antibody fragment
      fusion
<220> FEATURE:
<221> NAME/KEY: MISC_FEATURE
<222> LOCATION: (1)..(1)
<223> OTHER INFORMATION: Xaa can either be Asp or Ala
<220> FEATURE:
<221> NAME/KEY: MISC_FEATURE
<222> LOCATION: (2)..(2)
<223> OTHER INFORMATION: Xaa can either be Ile or Gln

<400> SEQUENCE: 36

Xaa Xaa Gln Met Thr Gln Ser Pro Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
                35                  40                  45

Tyr Tyr Thr Ser Arg Leu Glu Ser Gly Val Pro Ser Arg Phe Ser Gly
                50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Gly Gly Gly Gly Ser Gly
                115                 120                 125

Gly Gly Ser Glu Val Gln Leu Val Glu Ser Gly Gly Gly Leu Val Gln
                130                 135                 140

Pro Gly Gly Ser Leu Arg Leu Ser Cys Ala Ala Ser Gly Tyr Ser Phe
145                 150                 155                 160

Thr Gly Tyr Thr Met Asn Trp Val Arg Gln Ala Pro Gly Lys Gly Leu
                165                 170                 175

Glu Trp Val Ala Leu Ile Asn Pro Tyr Lys Gly Val Ser Thr Tyr Asn
                180                 185                 190

Gln Lys Phe Lys Asp Arg Phe Thr Ile Ser Val Asp Lys Ser Lys Asn
                195                 200                 205

Thr Ala Tyr Leu Gln Met Asn Ser Leu Arg Ala Glu Asp Thr Ala Val
                210                 215                 220

Tyr Tyr Cys Ala Arg Ser Gly Tyr Tyr Gly Asp Ser Asp Trp Tyr Phe
225                 230                 235                 240

Asp Val Trp Gly Gln Gly Thr Leu Val Thr Val Ser Ser Gly Gly Gly
                245                 250                 255

Gly Ser Asp Gly Gly Ile Thr Gln Ser Pro Lys Tyr Leu Phe Arg Lys
                260                 265                 270

Glu Gly Gln Asn Val Thr Leu Ser Cys Glu Gln Asn Leu Asn His Asp
                275                 280                 285
```

-continued

```
Ala Met Tyr Trp Tyr Arg Gln Asp Pro Gly Gln Gly Leu Arg Leu Ile
    290                 295                 300

Tyr Tyr Ser Trp Ala Gln Gly Asp Phe Gln Lys Gly Asp Ile Ala Glu
305                 310                 315                 320

Gly Tyr Ser Val Ser Arg Glu Lys Lys Glu Ser Phe Pro Leu Thr Val
                325                 330                 335

Thr Ser Ala Gln Lys Asn Pro Thr Ala Phe Tyr Leu Cys Ala Ser Ser
            340                 345                 350

Trp Gly Ala Pro Tyr Glu Gln Tyr Phe Gly Pro Gly Thr Arg Leu Thr
        355                 360                 365

Val Thr Glu Asp Leu Lys Asn Val Phe Pro Pro Glu Val Ala Val Phe
    370                 375                 380

Glu Pro Ser Glu Ala Glu Ile Ser His Thr Gln Lys Ala Thr Leu Val
385                 390                 395                 400

Cys Leu Ala Thr Gly Phe Tyr Pro Asp His Val Glu Leu Ser Trp Trp
                405                 410                 415

Val Asn Gly Lys Glu Val His Ser Gly Val Cys Thr Asp Pro Gln Pro
            420                 425                 430

Leu Lys Glu Gln Pro Ala Leu Asn Asp Ser Arg Tyr Ala Leu Ser Ser
        435                 440                 445

Arg Leu Arg Val Ser Ala Thr Phe Trp Gln Asp Pro Arg Asn His Phe
    450                 455                 460

Arg Cys Gln Val Gln Phe Tyr Gly Leu Ser Glu Asn Asp Glu Trp Thr
465                 470                 475                 480

Gln Asp Arg Ala Lys Pro Val Thr Gln Ile Val Ser Ala Glu Ala Trp
                485                 490                 495

Gly Arg Ala Asp
            500

<210> SEQ ID NO 37
<211> LENGTH: 1852
<212> TYPE: DNA
<213> ORGANISM: Artificial Sequence
<220> FEATURE:
<223> OTHER INFORMATION: Lentivirus vector insert

<400> SEQUENCE: 37
gctagccgcc accatggaaa ccctgctggg cgtgagcctg gtcatcctgt ggctgcagct      60
ggccagagtg aattcccagc agggcgaaga ggaccccccag gccctcagca tccaggaagg     120
cgagaacgcc accatgaact gcagctacaa gaccagcatc aacaacctgc agtggtacag     180
acagaacagc ggcagaggcc tggtgcacct gatcctgatc agaagcaacg agcgggagaa     240
gcacagcggc aggctgagag tgaccctgga caccagcaag aagtccagca gcctgctgat     300
caccgccagc agagccgccg acaccgccag ctactttgcc gccaccgacg gcgacacccc     360
cctggtgttc ggcaagggca ccagactgag cgtgatcgcc aatattcaga gcccgacccc     420
cgccgtctac cagctgcggg acagcaagag cagcgacaag agcgtgtgcc tgttcaccga     480
cttcgacagc cagaccaacg tgtcccgaga caggacagc gacgtgtaca tcaccgacaa     540
gaccgtgctg gacatgcgga gcatggactt caagagcaac agcgccgtgg cctggtccaa     600
caagagcgac ttcgcctgcg ccaacgcctt caacaacagc atcatccccg aggacacctt     660 tttcccagc ccgagagca gctgcgacgt caaactggtg gagaagtcct tcgagacaga     720
caccaacctg aacttccaga acctctccgt gatcggcttc agaatcctgc tgctgaaggt     780
ggccggcttc aacctgctga tgaccctgcg gctgtggagc agcggcagcc gggccaagag     840
```

-continued

```
aagcggatcc ggcgccacca acttctccct gctgaagcag gccggcgacg tggaggaaaa    900
ccctggccct aggatgagca accaggtgct ctgctgcgtg gtgctgtgtt tcctgggggc    960
caacaccgtg gacggcggca tcacccagag ccccaagtac ctgttccgga agagggcca   1020
gaacgtcacc ctgagctgcg agcagaacct caaccacgac gccatgtact ggtacaggca   1080
ggacccagga caaggcctcc ggctgatcta ctacagccag atcgtgaacg acttccagaa   1140
gggcgatatt gccgagggct acagcgtgtc ccgggagaag aaagagagct tccccctgac   1200
cgtcaccagc gcccagaaga accccaccgc cttctacctg tgcgccagca gcatcggcgg   1260
accctacgag cagtacttcg gccctggcac ccggctgaca gtgactgagg acctgaagaa   1320
cgtgttcccc cccgaggtgg ccgtgttcga gcccagcgag gccgagatca gccacaccca   1380
gaaagccacc ctggtctgcc tggccaccgg cttttacccc gaccacgtgg agctgtcttg   1440
gtgggtgaac ggcaaagagg tgcacagcgg cgtcagcacc gaccccagc ctctcaaaga   1500
gcagcccgcc ctgaacgaca gccggtactg cctcagctct cggctgcggg tgtccgccac   1560
cttctggcag aaccccgga accacttccg gtgccaggtg cagttctacg gcctgagcga   1620
gaacgacgag tggactcagg atagagccaa gcccgtgacc cagatcgtgt ccgccgaggc   1680
ctgggggcgc gccgattgcg gcttcaccag cgagagctat cagcagggcg tgctgtctgc   1740
caccatcctg tacagatcc tgctgggcaa ggccaccctg tacgccgtgc tcgtgtctgc   1800
cctggtgctg atggctatgg tcaagcggaa ggacagccgg ggctaagtcg ac           1852
```

<210> SEQ ID NO 38
<211> LENGTH: 610
<212> TYPE: PRT
<213> ORGANISM: Artificial Sequence
<220> FEATURE:
<223> OTHER INFORMATION: Lentivirus vector insert

<400> SEQUENCE: 38

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
                100                 105                 110

Gly Asp Thr Pro Leu Val Phe Gly Lys Gly Thr Arg Leu Ser Val Ile
            115                 120                 125

Ala Asn Ile Gln Lys Pro Asp Pro Ala Val Tyr Gln Leu Arg Asp Ser
        130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
                180                 185                 190
```

```
Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser Gly Ser
            260                 265                 270

Arg Ala Lys Arg Ser Gly Ser Gly Ala Thr Asn Phe Ser Leu Leu Lys
        275                 280                 285

Gln Ala Gly Asp Val Glu Glu Asn Pro Gly Pro Arg Met Ser Asn Gln
    290                 295                 300

Val Leu Cys Cys Val Val Leu Cys Phe Leu Gly Ala Asn Thr Val Asp
305                 310                 315                 320

Gly Gly Ile Thr Gln Ser Pro Lys Tyr Leu Phe Arg Lys Glu Gly Gln
                325                 330                 335

Asn Val Thr Leu Ser Cys Glu Gln Asn Leu Asn His Asp Ala Met Tyr
            340                 345                 350

Trp Tyr Arg Gln Asp Pro Gly Gln Gly Leu Arg Leu Ile Tyr Tyr Ser
        355                 360                 365

Gln Ile Val Asn Asp Phe Gln Lys Gly Asp Ile Ala Glu Gly Tyr Ser
    370                 375                 380

Val Ser Arg Glu Lys Lys Glu Ser Phe Pro Leu Thr Val Thr Ser Ala
385                 390                 395                 400

Gln Lys Asn Pro Thr Ala Phe Tyr Leu Cys Ala Ser Ser Ile Gly Gly
                405                 410                 415

Pro Tyr Glu Gln Tyr Phe Gly Pro Gly Thr Arg Leu Thr Val Thr Glu
            420                 425                 430

Asp Leu Lys Asn Val Phe Pro Pro Glu Val Ala Val Phe Glu Pro Ser
        435                 440                 445

Glu Ala Glu Ile Ser His Thr Gln Lys Ala Thr Leu Val Cys Leu Ala
    450                 455                 460

Thr Gly Phe Tyr Pro Asp His Val Glu Leu Ser Trp Trp Val Asn Gly
465                 470                 475                 480

Lys Glu Val His Ser Gly Val Ser Thr Asp Pro Gln Pro Leu Lys Glu
                485                 490                 495

Gln Pro Ala Leu Asn Asp Ser Arg Tyr Cys Leu Ser Ser Arg Leu Arg
            500                 505                 510

Val Ser Ala Thr Phe Trp Gln Asn Pro Arg Asn His Phe Arg Cys Gln
        515                 520                 525

Val Gln Phe Tyr Gly Leu Ser Glu Asn Asp Glu Trp Thr Gln Asp Arg
    530                 535                 540

Ala Lys Pro Val Thr Gln Ile Val Ser Ala Glu Ala Trp Gly Arg Ala
545                 550                 555                 560

Asp Cys Gly Phe Thr Ser Glu Ser Tyr Gln Gln Gly Val Leu Ser Ala
                565                 570                 575

Thr Ile Leu Tyr Glu Ile Leu Leu Gly Lys Ala Thr Leu Tyr Ala Val
            580                 585                 590

Leu Val Ser Ala Leu Val Leu Met Ala Met Val Lys Arg Lys Asp Ser
        595                 600                 605

Arg Gly
    610
```

<210> SEQ ID NO 39
<211> LENGTH: 36
<212> TYPE: DNA
<213> ORGANISM: Artificial Sequence
<220> FEATURE:
<223> OTHER INFORMATION: PCR oligonucleotide

<400> SEQUENCE: 39
ggaattccat atgagtcaac aaggagaaga agatcc                              36

<210> SEQ ID NO 40
<211> LENGTH: 36
<212> TYPE: DNA
<213> ORGANISM: Artificial Sequence
<220> FEATURE:
<223> OTHER INFORMATION: PCR oligonucleotide

<400> SEQUENCE: 40
ttgtcagtcg acttagagtc tctcagctgg tacacg                              36

<210> SEQ ID NO 41
<211> LENGTH: 36
<212> TYPE: DNA
<213> ORGANISM: Artificial Sequence
<220> FEATURE:
<223> OTHER INFORMATION: PCR oligonucleotide

<400> SEQUENCE: 41
tctctcatat ggatggtgga attactcaat ccccaa                              36

<210> SEQ ID NO 42
<211> LENGTH: 32
<212> TYPE: DNA
<213> ORGANISM: Artificial Sequence
<220> FEATURE:
<223> OTHER INFORMATION: PCR oligonucleotide

<400> SEQUENCE: 42
tagaaaccgg tggccaggca caccagtgtg gc                                  32

<210> SEQ ID NO 43
<211> LENGTH: 10
<212> TYPE: PRT
<213> ORGANISM: Artificial Sequence
<220> FEATURE:
<223> OTHER INFORMATION: Irrelevant peptide used as a control

<400> SEQUENCE: 43

Glu Leu Ala Gly Ile Gly Ile Leu Thr Val
1               5                   10

<210> SEQ ID NO 44
<211> LENGTH: 29
<212> TYPE: PRT
<213> ORGANISM: Artificial Sequence
<220> FEATURE:
<223> OTHER INFORMATION: Artificial peptide linker

<400> SEQUENCE: 44

Arg Thr Ser Gly Pro Gly Asp Gly Gly Lys Gly Gly Pro Gly Lys Gly
1               5                   10                  15

Pro Gly Gly Glu Gly Thr Lys Gly Thr Gly Pro Gly Gly
            20                  25

<210> SEQ ID NO 45

```
<211> LENGTH: 203
<212> TYPE: PRT
<213> ORGANISM: Artificial Sequence
<220> FEATURE:
<223> OTHER INFORMATION: T cell receptor alpha chain

<400> SEQUENCE: 45

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Leu Leu Ile Thr Ala Ser Arg
65                  70                  75                  80

Ala Ala Asp Thr Ala Ser Tyr Phe Cys Ala Thr Asp Gly Asp Thr Pro
                85                  90                  95

Leu Val Phe Gly Lys Gly Thr Arg Leu Ser Val Ile Ala Asn Ile Gln
            100                 105                 110

Lys Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
    130                 135                 140

Gln Ser Lys Asp Ser Asp Val Tyr Ile Thr Asp Lys Cys Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser
        195                 200

<210> SEQ ID NO 46
<211> LENGTH: 242
<212> TYPE: PRT
<213> ORGANISM: Artificial Sequence
<220> FEATURE:
<223> OTHER INFORMATION: T cell receptor beta chain

<400> SEQUENCE: 46

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Gly
                85                  90                  95

Gly Pro Tyr Glu Gln Tyr Phe Gly Pro Gly Thr Arg Leu Thr Val Thr
            100                 105                 110

Glu Asp Leu Lys Asn Val Phe Pro Pro Glu Val Ala Val Phe Glu Pro
        115                 120                 125
```

```
Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 47
<211> LENGTH: 12
<212> TYPE: PRT
<213> ORGANISM: Artificial Sequence
<220> FEATURE:
<223> OTHER INFORMATION: Artificial peptide linker

<400> SEQUENCE: 47

Gly Gly Glu Gly Gly Gly Ser Glu Gly Gly Gly Ser
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Artificial peptide linker

<400> SEQUENCE: 48

Gly Gly Gly Gly Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Artificial peptide linker

<400> SEQUENCE: 49

Gly Gly Gly Ser Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Artificial peptide linker

<400> SEQUENCE: 50

Gly Gly Ser Gly Gly
1               5

<210> SEQ ID NO 51
<211> LENGTH: 5
<212> TYPE: PRT
```

```
<213> ORGANISM: Artificial Sequence
<220> FEATURE:
<223> OTHER INFORMATION: Artificial peptide linker

<400> SEQUENCE: 51

Gly Ser Gly Gly Gly
1               5
```